US009862944B2

(12) United States Patent
Burzio Eriz et al.

(10) Patent No.: US 9,862,944 B2
(45) Date of Patent: Jan. 9, 2018

(54) ANTISENSE OLIGONUCLEOTIDES FOR TREATMENT OF CANCER STEM CELLS

(71) Applicant: Andes Biotechnologies S.A., Ñuñoa, Santiago (CL)

(72) Inventors: Luis O. Burzio Eriz, Santiago (CL); Veronica A. Burzio Menendez, Santiago (CL); Jaime E. Villegas Olavarria, Santiago (CL)

(73) Assignee: ANDES BIOTECHNOLOGIES S.A., Santiago (CL)

( * ) Notice: Subject to any disclaimer, the term of this patent is extended or adjusted under 35 U.S.C. 154(b) by 0 days.

(21) Appl. No.: 14/775,654

(22) PCT Filed: Mar. 14, 2014

(86) PCT No.: PCT/US2014/029606
§ 371 (c)(1),
(2) Date: Sep. 11, 2015

(87) PCT Pub. No.: WO2014/153209
PCT Pub. Date: Sep. 25, 2014

(65) Prior Publication Data
US 2016/0138015 A1 May 19, 2016

Related U.S. Application Data

(60) Provisional application No. 61/937,438, filed on Feb. 7, 2014, provisional application No. 61/790,072, filed on Mar. 15, 2013, provisional application No. 61/785,269, filed on Mar. 14, 2013.

(51) Int. Cl.
| A61K 48/00 | (2006.01) |
| C07H 21/02 | (2006.01) |
| C07H 21/04 | (2006.01) |
| C12N 15/113 | (2010.01) |
| A61K 31/7088 | (2006.01) |
| A61K 45/06 | (2006.01) |
| A61K 31/7105 | (2006.01) |
| C12N 5/09 | (2010.01) |

(52) U.S. Cl.
CPC ........ *C12N 15/113* (2013.01); *A61K 31/7088* (2013.01); *A61K 31/7105* (2013.01); *A61K 45/06* (2013.01); *C12N 5/0693* (2013.01); *C12N 2310/113* (2013.01); *C12N 2320/30* (2013.01); *C12N 2320/31* (2013.01); *C12N 2501/65* (2013.01); *C12N 2501/999* (2013.01); *C12N 2510/00* (2013.01)

(58) Field of Classification Search
CPC .............................. A61K 48/00; C12N 15/113
See application file for complete search history.

(56) References Cited

U.S. PATENT DOCUMENTS

| 3,687,808 A | 8/1972 | Merigan, Jr. et al. |
| 5,093,246 A | 3/1992 | Cech et al. |
| 5,194,599 A | 3/1993 | Froehler et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,527,899 A | 6/1996 | Froehler |
| 5,539,082 A | 7/1996 | Nielsen et al. |
| 5,541,306 A | 7/1996 | Agrawal et al. |
| 5,550,111 A | 8/1996 | Suhadolnik et al. |
| 5,552,540 A | 9/1996 | Haralambidis |
| 5,563,253 A | 10/1996 | Agrawal et al. |
| 5,565,555 A | 10/1996 | Froehler et al. |
| 5,571,799 A | 11/1996 | Tkachuk et al. |
| 5,587,361 A | 12/1996 | Cook et al. |
| 5,587,469 A | 12/1996 | Cook et al. |
| 5,594,121 A | 1/1997 | Froehler et al. |
| 5,596,086 A | 1/1997 | Matteucci et al. |
| 5,596,091 A | 1/1997 | Switzer |
| 5,602,240 A | 2/1997 | Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,070 A | 4/1997 | Cook et al. |

(Continued)

FOREIGN PATENT DOCUMENTS

| WO | WO-98/55495 A2 | 12/1998 |
| WO | WO-98/55495 A3 | 12/1998 |

(Continued)

OTHER PUBLICATIONS

Ahmed, N. et al. (Sep. 25, 2013). "Getting to know ovarian cancer ascites: opportunities for targeted therapy-based translational research," *Front Oncol.* 3(Article 256):1-12.
Chen, K. et al. (Jun. 2013, e-pub. May 20, 2013). "Understanding and targeting cancer stem cells: therapeutic implications and challenges," *Acta. Pharmacol. Sin.* 34(6):732-740.
Clarke, M. F. et al. (Oct. 1, 2006, e-pub. Sep. 21, 2006). "Cancer stem cells-perspectives on current status and future directions: AACR Workshop on cancer stem cells," *Cancer Res.* 66(19):9339-9344.
De Sanjosé, S. et al. (Nov. 2013, e-pub. Jul. 22, 2013). "Worldwide human papillomavirus genotype attribution in over 2000 cases of intraepithelial and invasive lesions of the vulva," *Eur. J. Cancer* 49(16):3450-3461.

(Continued)

*Primary Examiner* — Amy Bowman
(74) *Attorney, Agent, or Firm* — Mintz Levin Cohn Ferris Glovsky and Popeo, P.C.

(57) ABSTRACT

The invention provides oligonucleotides complementary to a non-coding chimeric mitochondrial RNA as well as compositions and kits comprising the same, and their use in treating and preventing metastasis or relapse of a cancer in an individual previously treated for cancer with a therapy. The invention also provides oligonucleotides complementary to a non-coding chimeric mitochondrial RNA as well as compositions and kits comprising the same, and their use in treating a refractory cancer (e.g., a refractory HPV-associated cancer).

11 Claims, 15 Drawing Sheets

(56) References Cited

U.S. PATENT DOCUMENTS

| | | |
|---|---|---|
| 5,625,050 A | 4/1997 | Beaton et al. |
| 5,633,360 A | 5/1997 | Bischofberger et al. |
| 5,645,985 A | 7/1997 | Froehler et al. |
| 5,646,269 A | 7/1997 | Matteucci et al. |
| 5,663,312 A | 9/1997 | Chaturvedula |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,714,331 A | 2/1998 | Buchardt et al. |
| 5,719,262 A | 2/1998 | Buchardt et al. |
| 5,721,218 A | 2/1998 | Froehler |
| 5,763,588 A | 6/1998 | Matteucci et al. |
| 5,792,608 A | 8/1998 | Swaminathan et al. |
| 5,830,653 A | 11/1998 | Froehler et al. |
| 6,005,096 A | 12/1999 | Matteucci et al. |
| 7,399,845 B2 | 7/2008 | Seth et al. |
| 8,318,686 B2 | 11/2012 | Burzio et al. |
| 8,614,095 B2 | 12/2013 | Radovanovic et al. |
| 8,895,719 B2 | 11/2014 | Burzio et al. |
| 2004/0224389 A1 | 11/2004 | Bellgrau et al. |
| 2006/0241033 A1 | 10/2006 | Burzio et al. |
| 2010/0292099 A1 | 11/2010 | Dreyfus et al. |
| 2012/0325090 A1 | 12/2012 | Takahashi |
| 2015/0064700 A1 | 3/2015 | Burzio et al. |
| 2016/0138109 A1 | 5/2016 | Villota Arcos et al. |

FOREIGN PATENT DOCUMENTS

| | | |
|---|---|---|
| WO | WO-98/55495 C1 | 12/1998 |
| WO | WO-2005/001030 A2 | 1/2005 |
| WO | WO-2005/001030 A3 | 1/2005 |
| WO | WO-2007/046511 A1 | 4/2007 |
| WO | WO-2014/153206 A2 | 9/2014 |
| WO | WO-2014/153206 A3 | 9/2014 |

OTHER PUBLICATIONS

Ding, Z. et al. (Sep. 15, 2000). "Human papillomavirus type 16-immortalized endocervical cells selected for resistance to cisplatin are malignantly transformed and have a multidrug resistance phenotype," *Int. J. Cancer* 87(6):818-823.

Domingo-Domenech, J. et al. (Sep. 11, 2012). "Suppression of acquired docetaxel resistance in prostate cancer through depletion of notch- and hedgehog-dependent tumor-initiating cells," *Cancer Cell* 22(3):373-388.

Elbashir, S. M. et al. (May 24, 2001). "Duplexes of 21-nucleotide RNAs mediate RNA interference in cultured mammalian cells," *Nature* 411(6836):494-498.

Englisch, U. et al. (Jun. 1991). "Chemically Modified Oligonucleotides as Probes and Inhibitors," *Angewandte Chemie International Edition* 30(6):613-629.

Feng, D. et al. (Nov. 2009). "Identification and characterization of cancer stem-like cells from primary carcinoma of the cervix uteri," *Oncol. Rep.* 22(5):1129-1134.

Haseloff, J. et al. (Oct. 15, 1989). "Sequences required for self-catalysed cleavage of the satellite RNA of tobacco ringspot virus," *Gene* 82(1):43-52.

International Search Report dated Aug. 21, 2014, for PCT Patent Application No. PCT/US2014/029606 filed on Mar. 14, 2014, four pages.

Kroschwitz, J. I. ed. (1990). "Polynucleotides" *Concise Encyclopedia of Polymer Science and Engineering*, John Wiley & Sons, Inc.: NY, pp. 858-859.

Kyle, R. A. et al. (Mar. 15, 2008). "Multiple myeloma," *Blood* 111(6):2962-2972.

Lu, P. Y. et al. (Jun., 2003). "siRNA-mediated antitumorigenesis for drug target validation and therapeutics," *Curr. Opin. Mol. Ther.* 5(3):225-234.

Mani S. A. et al. (May 16, 2008). "The epithelial-mesenchymal transition generates cells with properties of stem cells," *Cell* 133(4):704-715.

McManus, M. T. et al. (Oct. 2002). "Gene silencing in mammals by small interfering RNAs," *Nat. Rev. Genet.* 3(10):737-747.

Mukhopadhyay, P. et al. (Nov. 12, 2013). "Heterogeneity of functional properties of Clone 66 murine breast cancer cells expressing various stem cell phenotypes," *PloS One* 8(11) (e78725) pp. 1-15.

Muñoz, N. et al. (Feb. 6, 2003). "Epidemiologic classification of human papillomavirus types associated with cervical cancer," *N. Engl. J. Med.* 348(6):518-527.

Nielsen, P. E. et al. (Dec. 6, 1991). "Sequence-selective recognition of DNA by strand displacement with thymine-substituted polyamide," *Science* 254(5037):1497-1500.

Ohata, H. et al. (Oct. 1, 2012, e-pub. Sep. 20, 2012). "Induction of the stem-like cell regulator CD44 by Rho kinase inhibition contributes to the maintenance of colon cancer-initiating cells," *Cancer Res.* 72(19):5101-5110.

Perantoni, A. O. (1998). "Carcinogenesis" Chapter 3 in *The Biological Basis of Cancer*, McKinnell, R. G. et al. eds., Cambridge University Press: Cambridge, UK., p. 79-114.

Ponti, D. et al. (Jul. 1, 2005). "Isolation and in vitro propagation of tumorigenic breast cancer cells with stem/progenitor cell properties," *Cancer Res.* 65(13):5506-5511.

Rossi, J. J. (May 1, 1994). "Practical ribozymes. Making ribozymes work in cells," *Curr. Biol.* 4(5):469-471.

Sanghvi, Y. S. (1993). "Heterocyclic Base Modifications in Nucleic Acids and Their Applications in Antisense Oligonucleotides" Chapter 15 in *Antisense Research and Applications*, Crooke, S. T. et al. eds., CRC Press, Inc.: Boca Raton, FL, pp. 273-288.

Singh, S. K. et al. (Sep. 15, 2003). "Identification of a cancer stem cell in human brain tumors," *Cancer Res.* 63(18):5821-5828.

Tjalma, W. A. et al. (Feb. 15, 2013, e-pub. Jul. 24, 2012). "Differences in human papillomavirus type distribution in high-grade cervical intraepithelial neoplasia and invasive cervical cancer in Europe," *Int. J. Cancer* 132(4):854-867.

Tjalma, W. A. et al. (Jan. 2012). "Don't forget HPV-45 in cervical cancer screening," *Am. J. Clin. Pathol.* 137(1):161-163.

Wacheck, V. et al. (2003). "Small interfering RNA targeting bcl-2 sensitizes malignant melanoma," *Oligonucleotides* 13(5):393-400.

Walboomers, M. et al. (Sep. 1999). "Human papillomavirus is a necessary cause of invasive cervical cancer worldwide," *J. Pathol.* 189(1):12-19.

Written Opinion dated Aug. 21, 2014, for PCT Patent Application No. PCT/US2014/029606 filed on Mar. 14, 2014, four pages.

Zaug, A. J. et al. (May 11, 1984). "A labile phosphodiester bond at the ligation junction in a circular intervening sequence RNA," *Science* 224(4649):574-578.

Zhang, S. et al. (Jun. 1, 2008). "Identification and characterization of ovarian cancer-initiating cells from primary human tumors," *Cancer Res.* 68(11):4311-4320.

U.S. Appl. No. 15/139,255, filed Apr. 26, 2016, by Burzio et al.

U.S. Appl. No. 14/776,260, filed Mar. 14, 2014 (int'l filing date), by Villota Arcos et al.

Fan, X. et al. (May-Jun. 2012, e-published Sep. 16, 2010). "Effective enrichment of prostate cancer stem cells from spheres in a suspension culture system," *Urol Oncol* 30(3):314-318. (abstract only).

Harousseau, J.L. (Aug. 5, 2009). Maintenance therapy in multiple myeloma, *Hematol. Rep.* 1(2) (e12):65-69.

Landerer, E. et al. (Aug. 2011, e-published Feb. 24, 2011). "Nuclear localization of the mitochondrial ncRNAs in normal and cancer cells," *Cell Oncol* 34(4):297-305.

Liao, J. et al. (Jan. 2014). "Ovarian cancer spheroid cells with stem cell-like properties contribute to tumor generation, metastasis and chemotherapy resistance through hypoxia-resistant metabolism," *PloS One* 9(1):e84941.

Liu, J. et al. (Feb. 2013, e-published Nov. 29, 2012). "Spheroid body-forming cells in the human gastric cancer cell line MKN-45 possess cancer stem cell properties," *Int J Oncol* 42(2):453-459.

International Search Report dated Nov. 17, 2014, for PCT Application No. PCT/US2014/029602, filed on Mar. 14, 2014, 6 pages.

Written Opinion dated Nov. 17, 2014, for PCT Application No. PCT/US2014/029602, filed on Mar. 14, 2014.

Chihara, N. et al. (2011). "Mitochondrial DNA alterations in colorectal cancer cell lines," *J Nippon Med Sch* 78(1):13-21.

(56) References Cited

OTHER PUBLICATIONS

Varas, M. et al. (Nov. 2011). "Abstract B181:A lentivirus-encoding shRNA targeting a noncoding mitochondrial RNA inhibits melanoma tumor growth and metastasis in a mouse model in vivo," *Molecular Cancer Therapeutics* 10:11 Supplement, Abstract B181.

SEQUENCE LISTING

<160> NUMBER OF SEQ ID NOS: 205

<210> SEQ ID NO 1
<211> LENGTH: 2374
<212> TYPE: DNA
<213> ORGANISM: Homo sapiens

<400> SEQUENCE: 1

```
tctaatactg gtgatgctag aggtgatgtt tttggtaaac aggcggggta agatttgccg      60
agttcctttt actttttta acctttcctt atgagcatgc ctgtgttggg ttgacagtga     120
gggtaataat gacttgttgg ttgattgtag atattgggct gttaattgtc agttcagtgt     180
tttaatctga cgcaggctta tgcggaggag aatgttttca tgttacttat actaacatta     240
gttcttctat agggtgatag attggtccaa ttgggtgtga ggagttcagt tatatgtttg     300 ggattttta ggtagtgggt gttgagcttg aacgctttct taattggtgg ctgcttttag     360
gcctactatg ggtgttaaat tttttactct ctctacaagg ttttttccta gtgtccaaag     420
```

```
agctgttcct ctttggacta acagttaaat ttacaagggg atttagaggg ttctgtgggc      480
aaatttaaag ttgaactaag attctatctt ggacaaccag ctatcaccag gctcggtagg      540
tttgtcgcct ctacctataa atcttcccac tattttgcta catagacggg tgtgctcttt      600
tagctgttct taggtagctc gtctggtttc gggggtcttg gctttggctc tccttgcaaa      660
gttatttcta gttaattcat tatgcagaag gtataggggt tagtccttgc tatattatgc      720
ttggttataa ttttcatct ttcccttgcg gtactatatc tattgcgcca ggtttcaatt       780
tctatcgcct atactttatt tgggtaaatg gtttggctaa acctagcccc aaacccactc      840
caccttacta ccagacaacc ttagccaaac catttcccca aataaagtat aggcgataga      900
aattgaaacc tggcgcaata gatatagtac cgcaagggaa agatgaaaaa ttataaccaa      960
gcataatata gcaaggacta acccctatac cttctgcata atgaattaac tagaaataac     1020
tttgcaagga gagccaaagc taagacccccc gaaaccagac gagctaccta agaacagcta     1080
aaagagcaca cccgtctatg tagcaaaata gtgggaagat ttataggtag aggcgacaaa     1140
cctaccgagc ctggtgatag ctggttgtcc aagatagaat cttagttcaa ctttaaattt     1200
gcccacagaa ccctctaaat ccccttgtaa atttaactgt tagtccaaag aggaacagct     1260
ctttggacac taggaaaaaa ccttgtagag agtaaaaaa atttaacacc catagtaggc     1320
ctaaaagcag ccaccaatta agaaagcgtt caagctcaac acccactacc taaaaaatcc     1380
caaacatata actgaactcc tcacacccaa ttggaccaat ctatcaccct atagaagaac     1440
taatgttagt ataagtaaca tgaaaacatt ctcctccgca taagcctgcg tcagattaaa     1500
acactgaact gacaattaac agcccaatat ctacaatcaa ccaacaagtc attattaccc     1560
tcactgtcaa cccaacacag gcatgctcat aaggaaaggt taaaaaagt aaaaggaact     1620 cggcaaatct taccccgcct gtttaccaaa aacatcacct ctagcatcac cagtattaga     1680
ggcaccgcct gcccagtgac acatgtttaa cggccgcggt accctaaccg tgcaaaggta     1740
gcataatcac ttgttcctta ataggggacc tgtatgaatg gctccacgag ggttcagctg     1800
tctcttactt ttaaccagtg aaattgacct gcccgtgaag aggcgggcat aacacagcaa     1860
gacgagaaga cccctatggag ctttaattta ttaatgcaaa cagtacctaa caaacccaca     1920
ggtcctaaac taccaaacct gcattaaaaa tttcggttgg ggcgacctcg gagcagaacc     1980
caacctccga gcagtacatg ctaagacttc accagtcaaa gcgaactact atactcaatt     2040
gatccaataa cttgaccaac ggaacaagtt accctaggga taacagcgca atcctattct     2100
agagtccata tcaacaatag ggtttacgac ctcgatgttg gatcaggaca tcccgatggt     2160
gcagccgcta ttaaaggttc gtttgttcaa cgattaaagt cctacgtgat ctgagttcag     2220
accggagtaa tccaggtcgg tttctatcta ccttcaaatt cctccctgta cgaaaggaca     2280
agagaaataa ggcctacttc acaaagcgcc ttccccgta aatgatatca tctcaactta     2340
gtattatacc cacacccacc caagaacagg gttt                                 2374
```

<210> SEQ ID NO 2
<211> LENGTH: 1679
<212> TYPE: DNA
<213> ORGANISM: Homo sapiens

<400> SEQUENCE: 2

```
ggggtcttag ctttggctct ccttgcaaag ttatttctag ttaattcatt atgcagaagg       60 tatagggggtt agtccttgct atattatgct tggttataat ttttcatctt tcccttgcgg     120
```

```
tgctaaacct agccccaaac ccactccacc ttactaccag acaaccttag ccaaaccatt      180
tacccaaata agtataggc gatagaaatt gaaacctggc gcaatagata tagtaccgca      240
agggaaagat gaaaaattat aaccaagcat aatatagcaa ggactaaccc ctataccttc      300
tgcataatga attaactaga ataactttg caaggagagc caaagctaag accccgaaa       360 ccagacgagc tacctaagaa cagctaaaag agcacaccg tctatgtagc aaaatagtgg      420
gaagatttat aggtagaggc gacaaaccta ccgagcctgg tgatagctgg ttgtccaaga    480
tagaatctta gttcaacttt aaatttgccc acagaaccct ctaaatcccc ttgtaaattt     540
aactgttagt ccaaagagga acagctcttt ggacactagg aaaaaacctt gtagagagag    600 taaaaattt aacacccata gtaggcctaa aagcagccac caattaagaa agcgttcaag     660
ctcaacaccc actacctaaa aatcccaaa catataactg aactcctcac acccaattgg     720
accaatctat caccctatag aagaactaat gttagtataa gtaacatgaa acattctcc     780 tccgcataag cctgcgtcag attaaaacac tgaactgaca attaacagcc caatatctac    840
aatcaaccaa caagtcatta ttaccctcac tgtcaaccca acacaggcat gctcataagg   900
aaaggttaaa aaagtaaaa ggaactcggc aaatcttacc ccgcctgttt accaaaaaca    960
tcacctctag catcaccagt attagaggca ccgcctgccc agtgacacat gtttaacggc   1020
cgcggtaccc taaccgtgca aaggtagcat aatcacttgt tccttaaata gggacctgta   1080
tgaatggctc cacgagggtt cagctgtctc ttacttttaa ccagtgaaat tgacctgccc    1140
gtgaagaggc gggcataaca cagcaagacg agaagaccct atggagcttt aatttattaa    1200
tgcaaacagt acctaacaaa cccacaggtc ctaaactacc aaacctgcat taaaaatttc    1260
ggttggggcg acctcggagc agaacccaac ctccgagcag tacatgctaa gacttcacca    1320
gtcaaagcga actactatac tcaattgatc caataacttg accaacggaa caagttaccc    1380
tagggataac agcgcaatcc tattctagag tccatatcaa cataggggtt tacgacctcg    1440
atgttggatc aggacatccc aatggtgcag ccgctattaa aggttcgttt gttcaacgat    1500
taaagtccta cgtgatctga gttcagaccg gagtaatcca ggtcggtttc tatctacttc    1560
aaattcctcc ctgtacgaaa ggacaagaga aataaggcct acttcacaaa gcgccttccc    1620
ccgtaaatga tatcatctca acttagtatt atacccacac ccacccaaga acagggtttt   1679
```

<210> SEQ ID NO 3
<211> LENGTH: 1635
<212> TYPE: DNA
<213> ORGANISM: Homo sapiens

<400> SEQUENCE: 3

```
ggggtcttag ctttggctct ccttgcaaag ttatttctag ttaattcatt atgcagaagg     60 tatagggggtt agtccttgct aaacctagcc ccaaacccac tccaccttac taccagacaa   120
ccttagccaa accatttacc caaataaagt ataggcgata gaaattgaaa cctggcgcaa    180
tagatatagt accgcaaggg aaagatgaaa aattataacc aagcataata tagcaaggac    240
taacccctat accttctgca taatgaatta actagaaata actttgcaag gagagccaaa    300
gctaagaccc ccgaaaccag acgagctacc taagaacagc taaaagagca cacccgtcta    360
tgtagcaaaa tagtgggaag atttataggt agaggcgaca aacctaccga gcctggtgat    420
agctggttgt ccaagataga atcttagttc aactttaaat ttgcccacag aaccctctaa    480
atccccttgt aaatttaact gttagtccaa agaggaacag ctctttggac actaggaaaa    540
aaccttgtag agagtaaaa aaatttaaca cccatagtag gcctaaaagc agccaccaat    600
```

```
taagaaagcg ttcaagctca acacccacta cctaaaaaat cccaaacata taactgaact      660
cctcacaccc aattggacca atctatcacc ctatagaaga actaatgtta gtataagtaa      720
catgaaaaca ttctcctccg cataagcctg cgtcagatta aaacactgaa ctgacaatta      780
acagcccaat atctacaatc aaccaacaag tcattattac cctcactgtc aacccaacac      840
aggcatgctc ataaggaaag gttaaaaaaa gtaaaggaa ctcggcaaat cttaccccgc       900
ctgtttacca aaaacatcac ctctagcatc accagtatta gaggcaccgc ctgcccagtg      960
acacatgttt aacggccgcg gtaccctaac cgtgcaaagg tagcataatc acttgttcct     1020 taaatagga cctgtatgaa tggctccacg agggttcagc tgtctcttac ttttaaccag      1080
tgaaattgac ctgcccgtga agaggcgggc ataacacagc aagacgagaa gaccctatgg    1140
agctttaatt tattaatgca aacagtacct aacaaaccca caggtcctaa actaccaaac    1200
ctgcattaaa aatttcggtt ggggcgacct cggagcagaa cccaacctcc gagcagtaca    1260
tgctaagact tcaccagtca aagcgaacta ctatactcaa ttgatccaat aacttgacca    1320
acggaacaag ttaccctagg ataacagcg caatcctatt ctagagtcca tatcaacaat    1380
agggtttacg acctcgatgt tggatcagga catcccaatg gtgcagccgc tattaaaggt    1440
tcgtttgttc aacgattaaa gtcctacgtg atctgagttc agaccggagt aatccaggtc    1500
ggtttctatc tacttcaaat tcctcccgt acgaaaggac aagagaaata aggcctactt    1560
cacaaagcgc cttccccgt aaatgatatc atctcaactt agtattatac ccacacccac    1620
ccaagaacag ggttt                                                      1635

<210> SEQ ID NO 4
<211> LENGTH: 1921
<212> TYPE: DNA
<213> ORGANISM: Homo sapiens

<400> SEQUENCE: 4
aacctccgag cagtacatgc taagacttca ccagtcaaag cgaactacta tactcaattg       60
atccaataac ttgaccaacg gaacaagtta ccctagggat aacagcgcaa tcctattcta     120
gagtccatat caacaatagg gtttacgacc tcgatgttgg atcaggacat cccaatggtg    180
cagccgctat taaaggttcg tttgttcaac gattaaagtc ctacgtgatc tgagttcaga    240
ccggagtaat ccaggtcggt ttctatctac ttcaaattcc tccctgtacg aaaggacaag    300
agaaataagg cctacttcac aaagcgcctt cccccgtaaa tgatatcatc tcaacttagt    360
attataccct gttcttgggt gggtgtgggt ataatactaa gttgagatga tatcatttac    420
gggggaaggc gctttgtgaa gtaggcctta tttctcttgt cctttcgtac agggaggaat    480
ttgaagtaga tagaaaccga cctggattac tccggtctga actcagatca cgtaggactt    540
taatcgttga acaaacgaac ctttaatagc ggctgcacca tcgggatgtc ctgatccaac    600
atcgaggtcg taaaccctat tgttgatatg gactctagaa taggattgcg ctgttatccc    660
tagggtaact tgttccgttg gtcaagttat tggatcaatt gagtatagta gttcgctttg    720
actggtgaag tcttagcatg tactgctcgg aggttgggtt ctgctccgag gtcgccccaa    780
ccgaaatttt taatgcaggt ttggtagttt aggacctgtg ggtttgttag gtactgtttg    840
cattaataaa ttaaagctcc ataggtcttt ctcgtcttgc tgtgttatgc ccgcctcttc    900
acgggcaggt caatttcact ggttaaaagt aagagacagc tgaaccctcg tggagccatt    960
catacaggtc cctatttaag gaacaagtga ttatgctacc tttgcacggt tagggtaccg   1020
```

| | |
|---|---|
| cggccgttaa acatgtgtca ctgggcaggc ggtgcctcta atactggtga tgctagaggt | 1080 |
| gatgttttg gtaaacaggc ggggtaagat ttgccgagtt cctttactt ttttaacct | 1140 |
| ttccttatga gcatgcctgt gttgggttga cagtgagggt aataatgact tgttggttga | 1200 |
| ttgtagatat tgggctgtta attgtcagtt cagtgtttta atctgacgca ggcttatgcg | 1260 |
| gaggagaatg ttttcatgtt acttatacta acattagttc ttctataggg tgatagattg | 1320 |
| gtccaattgg gtgtgaggag ttcagttata tgtttgggat tttttaggta gtgggtgttg | 1380 |
| agcttgaacg cttctttaat tggtggctgc ttttaggcct actatgggtg ttaaattttt | 1440 |
| tactctctct acaaggtttt ttcctagtgt ccaagagagct gttcctcttt ggactaacag | 1500 |
| ttaaattac aaggggatt agagggttct gtgggcaaat ttaaagttga actaagattc | 1560 |
| tatcttggac aaccagctat caccaggctc ggtaggtttg tcgcctctac ctataaatct | 1620 |
| tcccactatt ttgctacata gacgggtgtg ctctttttagc tgttcttagg tagctcgtct | 1680 |
| ggtttcgggg gtcttagctt tggctctcct tgcaaagtta tttctagtta attcattatg | 1740 |
| cagaaggtat aggggttagt ccttgctata ttatgcttgg ttataatttt tcatctttcc | 1800 |
| cttgcggtac tatatctatt gcgccaggtt tcaatttcta tcgcctatac tttatttggg | 1860 |
| taaatggttt ggctaaggtt gtctggtagt aaggtggagt gggtttgggg ctaggtttag | 1920 |
| c | 1921 |

```
<210> SEQ ID NO 5
<211> LENGTH: 1744
<212> TYPE: DNA
<213> ORGANISM: Homo sapiens

<400> SEQUENCE: 5
```

| | |
|---|---|
| tagggataac agcgcaatcc tattctagag tccatatcaa caatagggtt tacgacctcg | 60 |
| atgttggatc aggacatccc gatggtgcag ccgctattaa aggttcgttt gttcaacgat | 120 |
| taaagtccta cgtgatctga gttcagaccg gagtaatcca ggtcggtttc tatctacctt | 180 |
| caaattcctc cctgttcttg ggtgggtgtg gtataatac taagttgaga tgatatcatt | 240 |
| tacgggggaa ggcgctttgt gaagtaggcc ttatttctct tgtccttttcg tacagggagg | 300 |
| aatttgaagt agatagaaac cgacctggat tactccggtc tgaactcaga tcacgtagga | 360 |
| ctttaatcgt tgaacaaacg aacctttaat agcggctgca ccatcgggat gtcctgatcc | 420 |
| aacatcgagg tcgtaaaccc tattgttgat atggactcta gaataggatt gcgctgttat | 480 |
| ccctagggta acttgttccg ttggtcaagt tattggatca attgagtata gtagttcgct | 540 |
| ttgactggtg aagtcttagc atgtactgct cggaggttgg gttctgctcc gaggtcgccc | 600 |
| caaccgaaat ttttaatgca ggtttggtag tttaggacct gtgggtttgt taggtactgt | 660 |
| ttgcattaat aaattaaagc tccataggt cttctcgtct tgctgtgtta tgcccgcctc | 720 |
| ttcacgggca ggtcaatttc actggttaaa agtaagagac agctgaaccc tcgtggagcc | 780 |
| attcatacag gtccctattt aaggaacaag tgattatgct acctttgcac ggttagggta | 840 |
| ccgcggccgt taaacatgtg tcactgggca ggcggtgcct ctaatactgg tgatgctaga | 900 |
| ggtgatgttt ttggtaaaca ggcggggtaa gatttgccga gttccttttta ctttttttaa | 960 |
| cctttcctta tgagcatgcc tgtgttgggt tgacagtgag ggtaataatg acttgttggt | 1020 |
| tgattgtaga tattgggctg ttaattgtca gttcagtgtt ttaatctgac gcaggcttat | 1080 |
| gcggaggaga atgttttcat gttacttata ctaacattag ttcttctata gggtgataga | 1140 |
| ttggtccaat tggggtgtgag gagttcagtt atatgtttgg gatttttttag gtagtgggtg | 1200 |

```
ttgagcttga acgctttctt aattggtggc tgcttttagg cctactatgg gtgttaaatt     1260
ttttactctc tctacaaggt ttttccctag tgtccaaaga gctgttcctc tttggactaa     1320
cagttaaatt tacaagggga tttagagggt tctgtgggca aatttaaagt tgaactaaga     1380
ttctatcttg gacaaccagc tatcaccagg ctcggtaggt tgtcgcctc tacctataaa      1440 tcttcccact attttgctac atagacgggt gtgctctttt agctgttctt aggtagctcg     1500
tctggtttcg ggggtcttag ctttggctct ccttgcaaag ttatttctag ttaattcatt     1560
atgcagaagg tataggggtt agtccttgct atattatgct tggttataat ttttcatctt     1620
tcccttgcgg tactatatct attgcgccag gtttcaattt ctatcgccta tactttattt     1680
gggtaaatgg tttggctaag gttgtctggt agtaaggtgg agtgggtttg gggctaggtt     1740
tagc                                                                   1744

<210> SEQ ID NO 6
<211> LENGTH: 1854
<212> TYPE: DNA
<213> ORGANISM: Homo sapiens

<400> SEQUENCE: 6
gaactcggca atcttaccc cgcctgttta ccaaaaacat cacctctagc atcaccagta       60
ttagaggcac cgcctgccca gtgacacatg tttaacggcc gcggtaccct aaccgtgcaa     120
aggtagcata atcacttgtt ccttaaatag ggacctgtat gaatggctcc acgagggttc     180
agctgtctct tactttaac cagtgaaatt gacctgcccg tgaagaggcg ggcatgacac      240
agcaagacga gaagacccta tggagcttta atttattaat gcaaacagta cctaacaaac     300
cctgttcttg ggtgggtgtg gtataaatac taagttgaga tgatatcatt tacggggaa      360 ggcgctttgt gaagtaggcc ttatttctct tgtcctttcg tacagggagg aatttgaagt     420
agatagaaac cgacctggat tactccggtc tgaactcaga tcacgtagga ctttaatcgt     480
tgaacaaacg aaccttttaat agcggctgca ccatcgggat gtcctgatcc aacatcgagg    540
tcgtaaaccc tattgttgat atggactcta gaataggatt gcgctgttat ccctagggta    600
acttgttccg ttggtcaagt tattggatca attgagtata gtagttcgct ttgactggtg    660
aagtcttagc atgtactgct cggaggttgg gttctgctcc gaggtcgccc caaccgaaat    720
ttttaatgca ggtttggtag tttaggacct gtgggtttgt taggtactgt ttgcattaat    780
aaattaaagc tccatagggt cttctcgtct tgctgtgtta tgcccgcctc ttcacgggca    840
ggtcaatttc actggttaaa agtaagagac agctgaaccc tcgtggagcc attcatacag    900
gtccctattt aaggaacaag tgattatgct acctttgcac ggttaggta ccgcggccgt     960 taaacatgtg tcactgggca ggcggtgcct ctaatactgg tgatgctaga ggtgatgttt    1020
ttggtaaaca ggcggggtaa gatttgccga gttcctttta cttttttaa cctttccttta   1080 tgagcatgcc tgtgttgggt tgacagtgag ggtaataatg acttgttggt tgattgtaga    1140
tattgggctg ttaattgtca gttcagtgtt ttaatctgac gcaggcttat gcggaggaga    1200
atgttttcat gttacttata ctaacattag ttcttctata gggtgataga ttggtccaat    1260
tgggtgtgag gagttcagtt atatgtttgg gattttttag gtagtgggtg ttgagcttga    1320
acgctttctt aattggtggc tgcttttagg cctactatgg gtgttaaatt ttttactctc    1380
tctacaaggt ttttcctag tgtccaaaga gctgttcctc tttggactaa cagttaaatt    1440
tacaagggga tttagagggt tctgtgggca aatttaaagt tgaactaaga ttctatcttg    1500
```

-continued

```
gacaaccagc tatcaccagg ctcggtaggt tgtcgcctc tacctataaa tcttcccact    1560
attttgctac atagacgggt gtgctctttt agctgttctt aggtagctcg tctggtttcg    1620
ggggtcttag ctttggctct ccttgcaaag ttatttctag ttaattcatt atgcagaagg    1680
tataggggtt agtccttgct atattatgct tggttataat ttttcatctt tcccttgcgg    1740
tactatatct attgcgccag gtttcaattt ctatcgccta tactttattt gggtaaatgg    1800
tttggctaag gttgtctggt agtaaggtgg agtgggtttg gggctaggtt tagc           1854
```

<210> SEQ ID NO 7
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 7
taggtttagc accgcaaggg                    20

<210> SEQ ID NO 8
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 8
taggtttagc aaggactaac                    20

<210> SEQ ID NO 9
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 9
ggggtaagat ttgccgag                      18

<210> SEQ ID NO 10
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 10
atgctagagg tgatgttttt gg                 22

<210> SEQ ID NO 11
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 11
cggtgcctct aatactgg                      18

<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 12
gttaaacatg tgtcactggg                                               20

<210> SEQ ID NO 13
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 13
ttgcacggtt agggtacc                                                 18

<210> SEQ ID NO 14
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 14
ggaacaagtg attatgctac c                                             21

<210> SEQ ID NO 15
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 15
ggagccattc atacaggtcc c                                             21

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
agtaagagac agctgaaccc                                               20

<210> SEQ ID NO 17
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 17
ggcaggtcaa tttcactgg                                                19

<210> SEQ ID NO 18
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 18
gctgtgttat gcccgcctc                                                19

<210> SEQ ID NO 19
```

```
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 19
agctccatag ggtcttctc                                                    19

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
gttaggtact gtttgcatta                                                   20

<210> SEQ ID NO 21
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 21
aagtcttagc atgtactg                                                     18

<210> SEQ ID NO 22
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 22
tagtagttcg ctttgactg                                                    19

<210> SEQ ID NO 23
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 23
caagttattg gatcaattg                                                    19

<210> SEQ ID NO 24
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 24
gggtaacttg ttccgttg                                                     18

<210> SEQ ID NO 25
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 25
```

| | |
|---|---|
| aataggattg cgctgtta | 18 |

```
<210> SEQ ID NO 26
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 26
```

| | |
|---|---|
| cctattgttg atatggac | 18 |

```
<210> SEQ ID NO 27
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 27
```

| | |
|---|---|
| ctgatccaac atcgagg | 17 |

```
<210> SEQ ID NO 28
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 28
```

| | |
|---|---|
| tagcggctgc accattgg | 18 |

```
<210> SEQ ID NO 29
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 29
```

| | |
|---|---|
| gttgaacaaa cgaaccttt | 19 |

```
<210> SEQ ID NO 30
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 30
```

| | |
|---|---|
| aactcagatc acgtaggac | 19 |

```
<210> SEQ ID NO 31
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 31
```

| | |
|---|---|
| cgacctggat tactccgg | 18 |

```
<210> SEQ ID NO 32
<211> LENGTH: 18
<212> TYPE: DNA
```

```
<213> ORGANISM: Artificial Sequence
<220> FEATURE:
<223> OTHER INFORMATION: Antisense Oligonucleotide

<400> SEQUENCE: 32
ggaatttgaa gtagatag                                                 18

<210> SEQ ID NO 33
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 33
ctcttgtcct ttcgtacag                                                19

<210> SEQ ID NO 34
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 34
ggcgctttgt gaagtagg                                                 18

<210> SEQ ID NO 35
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 35
gttgagatga tatcatttac gg                                            22

<210> SEQ ID NO 36
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 36
cacccaccca agaacagg                                                 18

<210> SEQ ID NO 37
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 37
caacttagta ttatacccac accca                                         25

<210> SEQ ID NO 38
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 38
tcccccgtaa atgattacat ct                                            22
```

<210> SEQ ID NO 39
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 39
gagaaataag gcctacttca caaag                                         25

<210> SEQ ID NO 40
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 40
caaattcctc cctgtacgaa ag                                            22

<210> SEQ ID NO 41
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 41
agtaatccag gtcggtttct atct                                          24

<210> SEQ ID NO 42
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 42
aagtcctagc tgatctgagt tcag                                          24

<210> SEQ ID NO 43
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 43
gctattaaag gttcgtttgt tcaac                                         25

<210> SEQ ID NO 44
<211> LENGTH: 16
<212> TYPE: DNA
<213> ORGANISM: Artificial Sequence
<220> FEATURE:
<223> OTHER INFORMATION: Antisense Oligonucleotide

<400> SEQUENCE: 44
tcccgatggt gcagcc                                                   16

<210> SEQ ID NO 45
<211> LENGTH: 22
<212> TYPE: DNA
<213> ORGANISM: Artificial Sequence
<220> FEATURE:

<223> OTHER INFORMATION: Antisense Oligonucleotide

<400> SEQUENCE: 45
ttacgacctc gatgttggat ca                                    22

<210> SEQ ID NO 46
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 46
atcctattct agagtccata tcaac                                 25

<210> SEQ ID NO 47
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 47
aataggattg cgctgttatc ccta                                  24

<210> SEQ ID NO 48
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 48
tagggataac agcgcatacc tatt                                  24

<210> SEQ ID NO 49
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 49
ggaacaagtt accctaggga taa                                   23

<210> SEQ ID NO 50
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 50
ttgatccaat aacttgacca acg                                   23

<210> SEQ ID NO 51
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 51
acttcaccag tcaaagcgaa c                                     21

```
<210> SEQ ID NO 52
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 52
aacccaacct ccgagcag                                                 18

<210> SEQ ID NO 53
<211> LENGTH: 16
<212> TYPE: DNA
<213> ORGANISM: Artificial Sequence
<220> FEATURE:
<223> OTHER INFORMATION: Antisense Oligonucleotide

<400> SEQUENCE: 53
gttggggcga cctcgg                                                   16

<210> SEQ ID NO 54
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 54
aaactaccaa acctgcttaa aa                                            22

<210> SEQ ID NO 55
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 55
aaacagtacc taacaaaccc acag                                          24

<210> SEQ ID NO 56
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 56
gaccctatgg agctttaatt tatta                                         25

<210> SEQ ID NO 57
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 57
cataacacag caagacgaga aga                                           23

<210> SEQ ID NO 58
<211> LENGTH: 18
<212> TYPE: DNA
<213> ORGANISM: Artificial Sequence
<220> FEATURE:
<223> OTHER INFORMATION: Antisense Oligonucleotide
```

<400> SEQUENCE: 58
tgacctgccc gtgaagag                                          18

<210> SEQ ID NO 59
<211> LENGTH: 26
<212> TYPE: DNA
<213> ORGANISM: Artificial Sequence
<220> FEATURE:
<223> OTHER INFORMATION: Antisense Oligonucleotide

<400> SEQUENCE: 59
cagctgtctc ttacttttaa ccagtg                                 26

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
ctgtatgaat ggctccacga                                        20

<210> SEQ ID NO 61
<211> LENGTH: 26
<212> TYPE: DNA
<213> ORGANISM: Artificial Sequence
<220> FEATURE:
<223> OTHER INFORMATION: Antisense Oligonucleotide

<400> SEQUENCE: 61
agcataatca cttgttcctt aaatag                                 26

<210> SEQ ID NO 62
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 62
accgtgcaaa ggtagcataa tca                                    23

<210> SEQ ID NO 63
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 63
tgattatgct acctttgcac ggt                                    23

<210> SEQ ID NO 64
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 64
gtaccctaac cgtgcaaag                                         19

<210> SEQ ID NO 65
<211> LENGTH: 21

```
<212> TYPE: DNA
<213> ORGANISM: Artificial Sequence
<220> FEATURE:
<223> OTHER INFORMATION: Antisense Oligonucleotide

<400> SEQUENCE: 65
cctgcccagt gacacatgtt t                                              21

<210> SEQ ID NO 66
<211> LENGTH: 25
<212> TYPE: DNA
<213> ORGANISM: Artificial Sequence
<220> FEATURE:
<223> OTHER INFORMATION: Antisense Oligonucleotide

<400> SEQUENCE: 66
cacctctagc atcaccagta ttaga                                          25

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
cttaccccgc ctgtttacca                                                20

<210> SEQ ID NO 68
<211> LENGTH: 26
<212> TYPE: DNA
<213> ORGANISM: Artificial Sequence
<220> FEATURE:
<223> OTHER INFORMATION: Antisense Oligonucleotide

<400> SEQUENCE: 68
aggttaaaaa aagtaaaagg aactcg                                         26

<210> SEQ ID NO 69
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 69
cccaacacag gcatgctca                                                 19

<210> SEQ ID NO 70
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 70
accaacaagt cattattacc ctca                                           24

<210> SEQ ID NO 71
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 71
```

```
tgacaattaa cagcccaata tcta                                              24

<210> SEQ ID NO 72
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 72
gcctgcgtca gattaaaaca c                                                 21

<210> SEQ ID NO 73
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 73
gtaacatgaa aacattctcc tccg                                              24

<210> SEQ ID NO 74
<211> LENGTH: 28
<212> TYPE: DNA
<213> ORGANISM: Artificial Sequence
<220> FEATURE:
<223> OTHER INFORMATION: Antisense Oligonucleotide

<400> SEQUENCE: 74
tatcacccta tagaagaact aatgttag                                          28

<210> SEQ ID NO 75
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 75
ctgaactcct cacacccaat t                                                 21

<210> SEQ ID NO 76
<211> LENGTH: 23
<212> TYPE: DNA
<213> ORGANISM: Artificial Sequence
<220> FEATURE:
<223> OTHER INFORMATION: Antisense Oligonucleotide

<400> SEQUENCE: 76
cactacctaa aaatcccaa aca                                                23

<210> SEQ ID NO 77
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 77
ttaagaaagc gttcaagctc a                                                 21

<210> SEQ ID NO 78
<211> LENGTH: 21
<212> TYPE: DNA
<213> ORGANISM: Artificial Sequence
```

```
<220> FEATURE:
<223> OTHER INFORMATION: Antisense Oligonucleotide

<400> SEQUENCE: 78
catagtaggc ctaaaagcag c                                              21

<210> SEQ ID NO 79
<211> LENGTH: 26
<212> TYPE: DNA
<213> ORGANISM: Artificial Sequence
<220> FEATURE:
<223> OTHER INFORMATION: Antisense Oligonucleotide

<400> SEQUENCE: 79
aaaccttgta gagagagtaa aaaatt                                         26

<210> SEQ ID NO 80
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 80
aaagaggaac agctctttgg acac                                           24

<210> SEQ ID NO 81
<211> LENGTH: 24
<212> TYPE: DNA
<213> ORGANISM: Artificial Sequence
<220> FEATURE:
<223> OTHER INFORMATION: Antisense Oligonucleotide

<400> SEQUENCE: 81
aatccccttg taaatttaac tgtt                                           24

<210> SEQ ID NO 82
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 82
ctttaaattt gcccacagaa c                                              21

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
ggttgtccaa gatagaatct                                                20

<210> SEQ ID NO 84
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 84
acaaacctac cgagcctgg                                                 19
```

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
aagatttata ggtagaggcg                                              20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
cccgtctatg tagcaaaata                                              20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
acctaagaac agctaaaaga                                              20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 88 taagacccccc gaaaccagac                                             20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
ataactttgc aaggagagcc                                              20

<210> SEQ ID NO 90
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 90
cttctgcata atgaattaac                                              20

<210> SEQ ID NO 91
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 91
atatagcaag gactaacccc                                              20

<210> SEQ ID NO 92
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 92
agatgaaaaa ttataaccaa                                              20

<210> SEQ ID NO 93
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 93
caatagatat agtaccgcaa                                              20

<210> SEQ ID NO 94
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 94
aggcgataga aattgaaacc                                              20

<210> SEQ ID NO 95
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 95
tagccaaacc atttacccaa                                              20

<210> SEQ ID NO 96
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 96
caccttacta ccagacaacc                                              20

<210> SEQ ID NO 97
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 97
ctaaacctag ccccaaacc                                               19

<210> SEQ ID NO 98
```

```
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 98
ctagcatcac cagtattaga                                                   20

<210> SEQ ID NO 99
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 99
ttaccaaaaa catcacctct                                                   20

<210> SEQ ID NO 100
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 100
gaactcggca aatcttaccc                                                   20

<210> SEQ ID NO 101
<211> LENGTH: 20
<212> TYPE: DNA
<213> ORGANISM: Artificial Sequence
<220> FEATURE:
<223> OTHER INFORMATION: Sense Oligonucleotide

<400> SEQUENCE: 101
gggtaagatt tgccgagttc                                                   20

<210> SEQ ID NO 102
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 102
gctcataagg aaaggttaaa a                                                 21

<210> SEQ ID NO 103
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 103
gtcaacccaa cacaggc                                                      17

<210> SEQ ID NO 104
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 104
```

-continued

```
accaacaagt cattattacc c                                           21

<210> SEQ ID NO 105
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 105
ggttgattgt agatattggg ct                                          22

<210> SEQ ID NO 106
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 106
attaacagcc caatatctac                                             20

<210> SEQ ID NO 107
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 107
tgcgtcagat taaaacactg                                             20

<210> SEQ ID NO 108
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 108
aaaacattct cctccgcata                                             20

<210> SEQ ID NO 109
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 109
gttagtataa gtaacatg                                               18

<210> SEQ ID NO 110
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 110
tggaccaatc tatcaccct                                              19

<210> SEQ ID NO 111
<211> LENGTH: 20
<212> TYPE: DNA
```

```
<213> ORGANISM: Artificial Sequence
<220> FEATURE:
<223> OTHER INFORMATION: Antisense Oligonucleotide

<400> SEQUENCE: 111
acatataact gaactcctca                                                   20

<210> SEQ ID NO 112
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 112
cacccactac ctaaaaaatc                                                   20

<210> SEQ ID NO 113
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 113
caccaattaa gaaagcgttg                                                   20

<210> SEQ ID NO 114
<211> LENGTH: 22
<212> TYPE: DNA
<213> ORGANISM: Artificial Sequence
<220> FEATURE:
<223> OTHER INFORMATION: Antisense Oligonucleotide

<400> SEQUENCE: 114
taggcctaaa agcagccacc aa                                                22

<210> SEQ ID NO 115
<211> LENGTH: 22
<212> TYPE: DNA
<213> ORGANISM: Artificial Sequence
<220> FEATURE:
<223> OTHER INFORMATION: Sense Oligonucleotide

<400> SEQUENCE: 115
ttggtggctg cttttaggcc ta                                                22

<210> SEQ ID NO 116
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 116
taacacccat agtaggcct                                                    19

<210> SEQ ID NO 117
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 117
aaccttgtag agagagtaaa                                                   20
```

<210> SEQ ID NO 118
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 118
aacagctctt tggacactag                                               20

<210> SEQ ID NO 119
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 119
aactgttagt ccaaagag                                                 18

<210> SEQ ID NO 120
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 120
ctctaaatcc ccttgtaaa                                                19

<210> SEQ ID NO 121
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 121
actttaaatt tgcccacag                                                19

<210> SEQ ID NO 122
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 122
ggttgtccaa gatagaatc                                                19

<210> SEQ ID NO 123
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 123
acaaacctac cgagcctcc                                                19

<210> SEQ ID NO 124
<211> LENGTH: 18
<212> TYPE: DNA
<213> ORGANISM: Artificial Sequence
<220> FEATURE:

```
<223> OTHER INFORMATION: Antisense Oligonucleotide

<400> SEQUENCE: 124
atttataggt tagaggcg                                                 18

<210> SEQ ID NO 125
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 125
atgtagcaaa atagtgggaa                                               20

<210> SEQ ID NO 126
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 126
taagaacagc taaaagagca c                                             21

<210> SEQ ID NO 127
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 127
cgaaaccaga cgagctac                                                 18

<210> SEQ ID NO 128
<211> LENGTH: 22
<212> TYPE: DNA
<213> ORGANISM: Artificial Sequence
<220> FEATURE:
<223> OTHER INFORMATION: Sense Oligonucleotide

<400> SEQUENCE: 128
ggggtcttag ctttggctct cc                                            22

<210> SEQ ID NO 129
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 129
taactttgca aggagagcca                                               20

<210> SEQ ID NO 130
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 130
accttctgca taatgaat                                                 18
```

```
<210> SEQ ID NO 131
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 131
atatagcaag gactaaccc                                                    19

<210> SEQ ID NO 132
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 132
gatgaaaaat tataaccaag                                                   20

<210> SEQ ID NO 133
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 133
aatagatata gtaccgcaag                                                   20

<210> SEQ ID NO 134
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 134
cgatagaaat tgaaacc                                                      17

<210> SEQ ID NO 135
<211> LENGTH: 20
<212> TYPE: DNA
<213> ORGANISM: Artificial Sequence
<220> FEATURE:
<223> OTHER INFORMATION: Sense Oligonucleotide

<400> SEQUENCE: 135
tactttattt gggtaaatgg                                                   20

<210> SEQ ID NO 136
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 136
ccatttaccc aaataaagta                                                   20

<210> SEQ ID NO 137
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 137
ttagccaaac catttaccca                                            20

<210> SEQ ID NO 138
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 138
aaggtggagt gggtttgggg c                                          21

<210> SEQ ID NO 139
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 139
gctaaggttg tctggta                                               17

<210> SEQ ID NO 140
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 140
atcgcctata ctttatttgg                                            20

<210> SEQ ID NO 141
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 141
atctattgcg ccaggtttca                                            20

<210> SEQ ID NO 142
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 142
ttttcatctt tcccttgcg                                             19

<210> SEQ ID NO 143
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 143
tccttgctat attatgcttg                                            20

<210> SEQ ID NO 144
<211> LENGTH: 20
```

```
<212> TYPE: DNA
<213> ORGANISM: Artificial Sequence
<220> FEATURE:
<223> OTHER INFORMATION: Antisense Oligonucleotide

<400> SEQUENCE: 144
cattatgcag aaggtatagg                                               20

<210> SEQ ID NO 145
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 145
tctccttgca aagttatt                                                 18

<210> SEQ ID NO 146
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 146
tttcgggggt cttagctttg                                               20

<210> SEQ ID NO 147
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 147
ctgttcttag gtagctcg                                                 18

<210> SEQ ID NO 148
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 148
tgctacatag acgggtgtg                                                19

<210> SEQ ID NO 149
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 149
cctctaccta taaatcttcc                                               20

<210> SEQ ID NO 150
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 150
```

```
gctatcacca ggctcgg                                                  17

<210> SEQ ID NO 151
<211> LENGTH: 17
<212> TYPE: DNA
<213> ORGANISM: Artificial Sequence
<220> FEATURE:
<223> OTHER INFORMATION: Antisense Oligonucleotide

<400> SEQUENCE: 151
aagttgaact aagattc                                                  17

<210> SEQ ID NO 152
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 152
gagggttctg tgggcaaatt                                               20

<210> SEQ ID NO 153
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 153
acagttaaat ttacaaggg                                                19

<210> SEQ ID NO 154
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 154
gtgtccaaag agctgttcc                                                19

<210> SEQ ID NO 155
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 155
tactctctct acaaggtttt                                               20

<210> SEQ ID NO 156
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 156
taggcctact atgggtgtta                                               20

<210> SEQ ID NO 157
<211> LENGTH: 21
<212> TYPE: DNA
<213> ORGANISM: Artificial Sequence
```

```
<220> FEATURE:
<223> OTHER INFORMATION: Antisense Oligonucleotide

<400> SEQUENCE: 157
aacgctttct taattggtgg c                                              21

<210> SEQ ID NO 158
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 158
ttttaggtag tgggtgttga                                                20

<210> SEQ ID NO 159
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 159
ggagttcagt tatatgtttg                                                20

<210> SEQ ID NO 160
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 160
tgatagattg gtccaattgg                                                20

<210> SEQ ID NO 161
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 161
ctaacattag ttcttctata g                                              21

<210> SEQ ID NO 162
<211> LENGTH: 18
<212> TYPE: DNA
<213> ORGANISM: Artificial Sequence
<220> FEATURE:
<223> OTHER INFORMATION: Antisense Oligonucleotide

<400> SEQUENCE: 162
atgcggagga gaatgttt                                                  18

<210> SEQ ID NO 163
<211> LENGTH: 19
<212> TYPE: DNA
<213> ORGANISM: Artificial Sequence
<220> FEATURE:
<223> OTHER INFORMATION: Antisense Oligonucleotide

<400> SEQUENCE: 163
tcagtgtttt aatctgacg                                                 19
```

```
<210> SEQ ID NO 164
<211> LENGTH: 21
<212> TYPE: DNA
<213> ORGANISM: Artificial Sequence
<220> FEATURE:
<223> OTHER INFORMATION: Antisense Oligonucleotide

<400> SEQUENCE: 164
gtagatattg ggctgttaat t                                             21

<210> SEQ ID NO 165
<211> LENGTH: 20
<212> TYPE: DNA
<213> ORGANISM: Artificial Sequence
<220> FEATURE:
<223> OTHER INFORMATION: Oligonucleotide

<400> SEQUENCE: 165
gtgagggtaa taatgacttg                                               20

<210> SEQ ID NO 166
<211> LENGTH: 20
<212> TYPE: DNA
<213> ORGANISM: Artificial Sequence
<220> FEATURE:
<223> OTHER INFORMATION: Oligonucleotide

<400> SEQUENCE: 166
atgagcatgc ctgtgttggt                                               20

<210> SEQ ID NO 167
<211> LENGTH: 19
<212> TYPE: DNA
<213> ORGANISM: Artificial Sequence
<220> FEATURE:
<223> OTHER INFORMATION: Oligonucleotide

<400> SEQUENCE: 167
ggtaagattt gccgagttc                                                19

<210> SEQ ID NO 168
<211> LENGTH: 20
<212> TYPE: DNA
<213> ORGANISM: Artificial Sequence
<220> FEATURE:
<223> OTHER INFORMATION: Oligonucleotide

<400> SEQUENCE: 168
tggtgatgct agaggtgatg                                               20

<210> SEQ ID NO 169
<211> LENGTH: 15
<212> TYPE: DNA
<213> ORGANISM: Artificial Sequence
<220> FEATURE:
<223> OTHER INFORMATION: Oligonucleotide

<400> SEQUENCE: 169
gcggtgcctc taata                                                    15

<210> SEQ ID NO 170
<211> LENGTH: 20
<212> TYPE: DNA
<213> ORGANISM: Artificial Sequence
<220> FEATURE:
<223> OTHER INFORMATION: Oligonucleotide
```

```
<400> SEQUENCE: 170
ggccgttaaa catgtgtcac                                                    20

<210> SEQ ID NO 171
<211> LENGTH: 20
<212> TYPE: DNA
<213> ORGANISM: Artificial Sequence
<220> FEATURE:
<223> OTHER INFORMATION: Oligonucleotide

<400> SEQUENCE: 171
tgattatgct acctttgcac                                                    20

<210> SEQ ID NO 172
<211> LENGTH: 20
<212> TYPE: DNA
<213> ORGANISM: Artificial Sequence
<220> FEATURE:
<223> OTHER INFORMATION: Oligonucleotide

<400> SEQUENCE: 172
ttaaggaaca agtgattatg                                                    20

<210> SEQ ID NO 173
<211> LENGTH: 20
<212> TYPE: DNA
<213> ORGANISM: Artificial Sequence
<220> FEATURE:
<223> OTHER INFORMATION: Oligonucleotide

<400> SEQUENCE: 173
tggagccatt catacaggtc                                                    20

<210> SEQ ID NO 174
<211> LENGTH: 20
<212> TYPE: DNA
<213> ORGANISM: Artificial Sequence
<220> FEATURE:
<223> OTHER INFORMATION: Oligonucleotide

<400> SEQUENCE: 174
aaaagtaaga gacagctgaa                                                    20

<210> SEQ ID NO 175
<211> LENGTH: 20
<212> TYPE: DNA
<213> ORGANISM: Artificial Sequence
<220> FEATURE:
<223> OTHER INFORMATION: Oligonucleotide

<400> SEQUENCE: 175
cacgggcagg tcaatttcac                                                    20

<210> SEQ ID NO 176
<211> LENGTH: 20
<212> TYPE: DNA
<213> ORGANISM: Artificial Sequence
<220> FEATURE:
<223> OTHER INFORMATION: Oligonucleotide

<400> SEQUENCE: 176
gtcttgctgt gttatgcccg                                                    20

<210> SEQ ID NO 177
```

```
<211> LENGTH: 19
<212> TYPE: DNA
<213> ORGANISM: Artificial Sequence
<220> FEATURE:
<223> OTHER INFORMATION: Oligonucleotide

<400> SEQUENCE: 177
aattaaagct ccatagggt                                                  19

<210> SEQ ID NO 178
<211> LENGTH: 21
<212> TYPE: DNA
<213> ORGANISM: Artificial Sequence
<220> FEATURE:
<223> OTHER INFORMATION: Oligonucleotide

<400> SEQUENCE: 178
gtttgttagg tactgtttgc a                                               21

<210> SEQ ID NO 179
<211> LENGTH: 19
<212> TYPE: DNA
<213> ORGANISM: Artificial Sequence
<220> FEATURE:
<223> OTHER INFORMATION: Oligonucleotide

<400> SEQUENCE: 179
aggtttggta gtttaggac                                                  19

<210> SEQ ID NO 180
<211> LENGTH: 20
<212> TYPE: DNA
<213> ORGANISM: Artificial Sequence
<220> FEATURE:
<223> OTHER INFORMATION: Oligonucleotide

<400> SEQUENCE: 180
gccccaaccg aaattttaa                                                  20

<210> SEQ ID NO 181
<211> LENGTH: 20
<212> TYPE: DNA
<213> ORGANISM: Artificial Sequence
<220> FEATURE:
<223> OTHER INFORMATION: Oligonucleotide

<400> SEQUENCE: 181
ctcggaggtt gggttctgct                                                 20

<210> SEQ ID NO 182
<211> LENGTH: 20
<212> TYPE: DNA
<213> ORGANISM: Artificial Sequence
<220> FEATURE:
<223> OTHER INFORMATION: Oligonucleotide

<400> SEQUENCE: 182
ctggtgaagt cttagcatgt                                                 20

<210> SEQ ID NO 183
<211> LENGTH: 20
<212> TYPE: DNA
<213> ORGANISM: Artificial Sequence
<220> FEATURE:
<223> OTHER INFORMATION: Oligonucleotide

<400> SEQUENCE: 183
```
caattgagta tagtagttcg                                          20

<210> SEQ ID NO 184
<211> LENGTH: 19
<212> TYPE: DNA
<213> ORGANISM: Artificial Sequence
<220> FEATURE:
<223> OTHER INFORMATION: Oligonucleotide

<400> SEQUENCE: 184
tgttccgttg gtcaagtta                                           19

<210> SEQ ID NO 185
<211> LENGTH: 20
<212> TYPE: DNA
<213> ORGANISM: Artificial Sequence
<220> FEATURE:
<223> OTHER INFORMATION: Oligonucleotide

<400> SEQUENCE: 185
aataggattg cgctgttatc                                          20

<210> SEQ ID NO 186
<211> LENGTH: 20
<212> TYPE: DNA
<213> ORGANISM: Artificial Sequence
<220> FEATURE:
<223> OTHER INFORMATION: Oligonucleotide

<400> SEQUENCE: 186
attgttgata tggactctag                                          20

<210> SEQ ID NO 187
<211> LENGTH: 20
<212> TYPE: DNA
<213> ORGANISM: Artificial Sequence
<220> FEATURE:
<223> OTHER INFORMATION: Oligonucleotide

<400> SEQUENCE: 187
atccaacatc gaggtcgtaa                                          20

<210> SEQ ID NO 188
<211> LENGTH: 19
<212> TYPE: DNA
<213> ORGANISM: Artificial Sequence
<220> FEATURE:
<223> OTHER INFORMATION: Oligonucleotide

<400> SEQUENCE: 188
gcggctgcac catcgggat                                           19

<210> SEQ ID NO 189
<211> LENGTH: 19
<212> TYPE: DNA
<213> ORGANISM: Artificial Sequence
<220> FEATURE:
<223> OTHER INFORMATION: Oligonucleotide

<400> SEQUENCE: 189
ttgaacaaac gaaccttta                                           19

<210> SEQ ID NO 190
<211> LENGTH: 20
<212> TYPE: DNA

```
<213> ORGANISM: Artificial Sequence
<220> FEATURE:
<223> OTHER INFORMATION: Oligonucleotide

<400> SEQUENCE: 190
aactcagatc acgtaggact                                              20

<210> SEQ ID NO 191
<211> LENGTH: 19
<212> TYPE: DNA
<213> ORGANISM: Artificial Sequence
<220> FEATURE:
<223> OTHER INFORMATION: Oligonucleotide

<400> SEQUENCE: 191
aaaccgacct ggattactc                                               19

<210> SEQ ID NO 192
<211> LENGTH: 20
<212> TYPE: DNA
<213> ORGANISM: Artificial Sequence
<220> FEATURE:
<223> OTHER INFORMATION: Oligonucleotide

<400> SEQUENCE: 192
agggaggaat ttgaaggtag                                              20

<210> SEQ ID NO 193
<211> LENGTH: 20
<212> TYPE: DNA
<213> ORGANISM: Artificial Sequence
<220> FEATURE:
<223> OTHER INFORMATION: Oligonucleotide

<400> SEQUENCE: 193
ggccttattt ctcttgtcct                                              20

<210> SEQ ID NO 194
<211> LENGTH: 20
<212> TYPE: DNA
<213> ORGANISM: Artificial Sequence
<220> FEATURE:
<223> OTHER INFORMATION: Oligonucleotide

<400> SEQUENCE: 194
ggaaggcgct ttgtgaagta                                              20

<210> SEQ ID NO 195
<211> LENGTH: 20
<212> TYPE: DNA
<213> ORGANISM: Artificial Sequence
<220> FEATURE:
<223> OTHER INFORMATION: Oligonucleotide

<400> SEQUENCE: 195
aagttgagat gatatcattt                                              20

<210> SEQ ID NO 196
<211> LENGTH: 17
<212> TYPE: DNA
<213> ORGANISM: Artificial Sequence
<220> FEATURE:
<223> OTHER INFORMATION: Oligonucleotide

<400> SEQUENCE: 196
cctgttcttg ggtgggt                                                 17
```

<210> SEQ ID NO 197
<211> LENGTH: 18
<212> TYPE: DNA
<213> ORGANISM: Artificial Sequence
<220> FEATURE:
<223> OTHER INFORMATION: Oligonucleotide

<400> SEQUENCE: 197
gtcctaaact accaaacc                                                     18

<210> SEQ ID NO 198
<211> LENGTH: 20
<212> TYPE: DNA
<213> ORGANISM: Artificial Sequence
<220> FEATURE:
<223> OTHER INFORMATION: Oligonucleotide

<400> SEQUENCE: 198
caccctctaa cctagagaag                                                   20

<210> SEQ ID NO 199
<211> LENGTH: 18
<212> TYPE: DNA
<213> ORGANISM: Artificial Sequence
<220> FEATURE:
<223> OTHER INFORMATION: Oligonucleotide

<400> SEQUENCE: 199
aggtggagtg gattgggg                                                     18

<210> SEQ ID NO 200
<211> LENGTH: 2374
<212> TYPE: RNA
<213> ORGANISM: Homo sapiens

<400> SEQUENCE: 200
ucuaauacug gugaugcuag aggugauguu uuugguaaac aggcggggua agauuugccg        60
aguuccuuuu acuuuuuuua accuuuccuu augagcaugc cuguguuggg uugacaguga      120
ggguaauaau gacuuguugg uugauuguag auauugggcu guuaauuguc aguucagugu      180
uuuaaucuga cgcaggcuua ugcggaggag aauguuuuca guuacuuuau acuaacauua      240
guucuucuau agggugauag auuggcccaa ugggguguga ggaguucagu uauauguuuu      300
ggauuuuuua gguaguggu guugagcuug aacgcuuucu uaauuggugg cugcuuuuag       360
gccuacuaug ggguuuaaau uuuuuacucu cucuacaagg uuuuuuccua uguccaaag       420 agcuguuccu cuuuggacua acaguuaaau uuacaagggg auuuagaggg uucuguggc       480 aaauuuaaag uugaacuaag auucuaucuu ggacaaccag cuaucaccag cucgguagg       540 uuugucgccu cuaccuauaa aucuucccac uauuuugcua cauagacggg ugugcucuuu      600
uagcuguucu uagguagcuc gucugguuuc gggggucuua gcuuggcuc uccuugcaaa       660 guuauuucua guuaauucau uaugcagaag guauaggggu uagccuugc uauauuaugc       720 uugguuauaa uuuuucaucu uucccuugcg guacuauauc uauugcgcca gguucaauu       780 ucuaucgccu auacuuuauu ugggguaaaug guuuggcuaa accuagcccc aaacccacuc     840
caccuuacua ccagacaacc uuagccaaac cauuuaccca aauaaaguau aggcgauaga      900
aauugaaacc uggcgcaaua gauauagu cgcaagggaa agaugaaaaa uuauaaccaa        960
gcauaauaua gcaaggacua accccuauac cuucugcaua augaauuaac uagaaauaac     1020

| | |
|---|---|
| uuugcaagga gagccaaagc uaagacccc gaaaccagac gagcuaccua agaacagcua | 1080 |
| aaagagcaca cccgucuaug uagcaaaaua gugggaagau uuauaggua aggcgacaaa | 1140 |
| ccuaccgagc cuggugauag cugguugucc aagauagaau cuuaguucaa cuuuaaauuu | 1200 |
| gcccacagaa cccucuaaau ccccuuguaa auuuaacugu uaguccaaag aggaacagcu | 1260 |
| cuuuggacac uaggaaaaaa ccuuguagag agaguaaaaa auuuacaccc cauaguaggc | 1320 |
| cuaaaagcag ccaccaauua agaaagcguu caagcucaac acccacuacc uaaaaaaucc | 1380 |
| caaacauaua acugaacucc ucacacccaa uuggaccaau cuaucacccu auagaagaac | 1440 |
| uaauguuagu auaaguaaca ugaaaacauu uccuccgca uaagccugcg ucagauuaaa | 1500 |
| acacugaacu gacaauuaac agcccaauau cuacaaucaa ccaacaaguc auuauuaccc | 1560 |
| ucacugucaa cccaacacag gcaugcucau aaggaaaggu uaaaaaagu aaaaggaacu | 1620 |
| cggcaaaucu uaccccgccu guuuaccaaa aacaucaccu cuagcaucac caguauuaga | 1680 |
| ggcaccgccu gcccagugac acauguuuaa cggccgcggu acccuaaccg ugcaaaggua | 1740 |
| gcauaaucac uuguuccuua auagggacc uguaugaaug cuccacgag gguucagcug | 1800 |
| ucucuuacuu uuaaccagug aaauugaccu gcccgugaag aggcgggcau aacacagcaa | 1860 |
| gacgagaaga cccuauggag cuuuaauuua uuaaugcaaa caguaccuaa caaacccaca | 1920 |
| gguccuaaac uaccaaaccu gcauaaaaaa uuucgguugg ggcgaccucg gagcagaacc | 1980 |
| caaccuccga gcaguacaug cuaagacuuc accagcaaaa gcgaacuacu auacucaauu | 2040 |
| gauccaauaa cuugaccaac ggaacaaguu acccaggga uaacagcgca auccuauucu | 2100 |
| agaguccaua ucaacaauag gguuuacgac cucgauguug gaucaggaca ucccgauggu | 2160 |
| gcagccgcua uuaaagguuc guuuguucaa cgauuaaagu ccuacgugau cugaguucag | 2220 |
| accggaguaa uccaggucgg uuucuaucua ccuucaaauu cucccuugua cgaaaggaca | 2280 |
| agagaaauaa ggccuacuuc acaaagcgcc uuccccgua aaugauauca ucucaacuua | 2340 |
| guauuuauacc cacacccacc caagaacagg guuu | 2374 |

<210> SEQ ID NO 201
<211> LENGTH: 1679
<212> TYPE: RNA
<213> ORGANISM: Homo sapiens

<400> SEQUENCE: 201

| | |
|---|---|
| ggggucuuag cuuuggcucu ccuugcaaag uuauuucuag uuaauucauu augcagaagg | 60 |
| uauaggguu aguccuugcu auauuaugcu ugguuauaau uuuucaucuu ucccuugcgg | 120 |
| ugcuaaaccu agcccaaac ccacuccacc uuacuaccag acaaccuuag ccaaaccauu | 180 |
| uacccaaaua aaguauaggc gauagaaauu gaaccuggc gcaauagaua uaguaccgca | 240 |
| agggaaagau gaaaaauuau aaccaagcau aauauagcaa ggacuacccc uauaccuuc | 300 |
| ugcauauga auuaacuaga auaacuuuug caaggagagc caaagcuaag accccgaaa | 360 |
| ccagacgagc uaccuaagaa cagcuaaaag agcacacccg ucuaugaugc aaauagugg | 420 |
| gaagauuuau aggauagagc gacaaaccua ccgagccugg ugauagcugg uuguccaaga | 480 |
| uagaaucuua guucaacuuu aaauuugccc acagaacccu cuaaucccc uuguaaauuu | 540 |
| aacuguuagu ccaaagagga acagcucuuu ggacacuagg aaaaaaccuu guagagagag | 600 |
| uaaaaauuu aacacccaua guaggccuaa agcagccac caauuaagaa agcguucaag | 660 |
| cucaacaccc acuaccuaaa aauccccaaa cauauaacug aacuccucac acccaauugg | 720 |
| accaaucuau cacccuauag aagaacuaau guuaguauaa guaacaugaa aacauucccc | 780 |

| | |
|---|---|
| uccgcauaag ccugcgucag auuaaaacac ugaacugaca auuaacagcc caauaucuac | 840 |
| aaucaaccaa caagucauua uuacccucac ugucaaccca acacaggcau gcucauaagg | 900 |
| aaagguuaaa aaaaguaaaa ggaacucggc aaaucuuacc ccgccuguuu accaaaaaca | 960 |
| ucaccucuag cauccaccagu auuagaggca ccgccugccc agugacacau guuuaacggc | 1020 |
| cgcgguaccc uaaccgugca aagguagcau aaucacuugu ccuuaaaua gggaccugua | 1080 |
| ugaauggcuc cacgagggu cagcugucuc uuacuuuuaa ccagugaaau ugaccugccc | 1140 |
| gugaagaggc gggcauaaca cagcaagacg agaagacccu uggagcuuu aauuuauuaa | 1200 |
| ugcaaacagu accuaacaaa cccacaggguc cuaaacuacc aaaccugcau uaaaaauuuc | 1260 |
| gguuggggcg accucggagc agaacccaac cuccgagcag uacaugcuaa gacuucacca | 1320 |
| gucaaagcga acuacuauac ucaauugauc caauaacuug accaacggaa caaguuaccc | 1380 |
| uagggauaac agcgcaaucc uauucuagag uccauaucaa caauaggguu uacgaccucg | 1440 |
| auguuggauc aggacauccc aauggugcag ccgcuauuaa agguucguuu guucaacgau | 1500 |
| uaaaguccua cgugaucuga uucagaccg gaguaaucca ggucgguuuc uaucuacuuc | 1560 |
| aaauuccucc cuguacgaaa ggacaagaga auuaaggccu acuucacaaa gcgccuuccc | 1620 |
| ccguaaauga uaucaucuca acuuaguauu auacccacac ccacccaaga acaggguuu | 1679 |

<210> SEQ ID NO 202
<211> LENGTH: 1635
<212> TYPE: RNA
<213> ORGANISM: Homo sapiens

<400> SEQUENCE: 202

| | |
|---|---|
| ggggucuuag cuuuggcucu ccuugcaaag uuauuucuag uuaauucauu augcagaagg | 60 |
| uauaggggu aguccuugcu aaaccuagcc ccaaacccac uccaccuuac uaccagacaa | 120 |
| ccuuagccaa accauuuacc caaauaaagu uaggcgaua gaaauugaaa ccuggcgcaa | 180 |
| uagauauagu accgcaaggg aaagaugaaa aauuauaacc aagcauaaua uagcaaggac | 240 |
| uaaccccuau accuucugca uaugaauua acuagaaaua acuuugcaag gagagccaaa | 300 |
| gcuaagaccc ccgaaaccag acgagcuacc uaagaacagc uaaaagagca cacccgucua | 360 |
| uguagcaaaa uagugggaag auuuauaggu agaggcgaca aaccuaccga gccuggugau | 420 |
| agcugguugu ccaagauaga aucuuaguuc aacuuuaaau uugcccacag aacccucuaa | 480 |
| auccccuugu aaauuuaacu guuaguccaa agaggaacag cucuuuggac acuaggaaaa | 540 |
| aaccuuguag agaguauaaa aaauuuaaca cccauaguag gccuaaaagc agccaccaau | 600 |
| uaagaaagcg uucaagcuca acacccacua ccuaaaaaau cccaaacaua uaacugaacu | 660 |
| ccucacaccc aauuggacca aucuaucacc uauagaagca acuaauguua guauaaguaa | 720 |
| caugaaaaca uucuccuccg cauaagccug cgucagauua aaacacugaa cugacaauua | 780 |
| acagcccaau aucuacaauc aaccaacaag ucauuauuac ccucacuguc aacccaacac | 840 |
| aggcaugcuc auaaggaaag guuaaaaaaa guaaaaggaa cucggcaaau cuuaccccgc | 900 |
| cuguuuacca aaaacaucac cucuagcauc accaguauua gaggaccgc cugcccagug | 960 |
| acacauguuu aacggccgcg guacccuaac cgugcaaagg uagcauaauc acuuguuccu | 1020 |
| uaaauaggga ccuguaugaa uggcucacg agggguucagc ugucucuuac uuuuaaccag | 1080 |
| ugaaauugac cugcccguga agaggcgggc auaacacagc aagacgagaa gacccuaugg | 1140 |
| agcuuuaauu uauuaaugca aacaguaccu aacaaaccca ggguccuaa acuaccaaac | 1200 |

| | |
|---|---|
| cugcauuaaa aauuucgguu ggggcgaccu cggagcagaa cccaaccucc gagcaguaca | 1260 |
| ugcuaagacu ucaccaguca aagcgaacua cuauacucaa uugauccaau aacuugacca | 1320 |
| acggaacaag uuacccuagg gauaacagcg caauccuauu cuagagucca uaucaacaau | 1380 |
| aggguuuacg accucgaugu uggaucagga caucccaaug gugcagccgc uauuaaaggu | 1440 |
| ucguuuguuc aacgauuaaa guccuacgug aucgaguuc agaccggagu aauccagguc | 1500 |
| gguuucuauc uacuucaaau uccucccugu acgaaaggac aagagaaaua aggccuacuu | 1560 |
| cacaaagcgc cuuccccgu aaaugauauc aucuccaacuu aguauuauac ccacacccac | 1620 |
| ccaagaacag gguuu | 1635 |

<210> SEQ ID NO 203
<211> LENGTH: 1921
<212> TYPE: RNA
<213> ORGANISM: Homo sapiens

<400> SEQUENCE: 203

| | |
|---|---|
| aaccuccgag caguacaugc uaagacuuca ccagucaaag cgaacuacua uacucaauug | 60 |
| auccauaac uugaccaacg gaacaaguua cccuagggau aacagcgcaa uccuauucua | 120 |
| gaguccauau caacaauagg guuuacgacc ucgauguugg aucaggacau cccaauggug | 180 |
| cagccgcuau uaaagguucg uuuguucaac gauuaaaguc cuacgugauc ugaguucaga | 240 |
| ccggaguauu ccaggucggu uucuaucuac uucaaauucc ucccgaucg aaaggacaag | 300 |
| agaaauaagg ccuacuucac aaagcgccuu cccccguaaa ugauaucauc aacuuagu | 360 |
| auuaucccu gucuuggggu ggugugggu auaauacuaa guugagauga uaucauuuac | 420 |
| ggggaaggc gcuuugugaa guaggccuua uuucucuugu ccuucguac agggaggaau | 480 |
| uugaaguaga uagaaaccga ccuggauuac uccggucuga acucagauca cguaggacuu | 540 |
| uaaucguuga acaaacgaac cuuuaauagc ggcugcacca ucgggaugu cugauccaac | 600 |
| aucgaggucg uaaacccuau uguugauaug gacucuagaa uaggauugcg cuguuauccc | 660 |
| uaggguaacu uguuccguug gucaaguuau uggaucaauu gaguauagua guucgcuuug | 720 |
| acuggugaag ucuuagcaug uacugcucgg agguuggguu cugcuccgag ucgccccaa | 780 |
| ccgaaauuu uaaugcaggu uugguaguuu aggaccugug gguuguuag guacuguuug | 840 |
| cauuaauaaa uuaaagcucc uaggguucu cucgucuugc uguguuaugc ccgcccuuc | 900 |
| acgggcaggu caauuucacu gguuaaaagu aagagacagc ugaacccucg uggagccauu | 960 |
| cauacagguc ccuauuuaag gaacaaguga uuaugcuacc uuugcacggu uaggguaccg | 1020 |
| cggccguuaa acaugugca cugggcaggc ggugccucua auacuggug ugcuagaggu | 1080 |
| gauguuuug guaaacaggc ggggaagau ugccgaguu ccuuuacuu uuuuuaaccu | 1140 |
| uuccuuauga gcaugccugu guugguuga cagugagggu aauaaugacu uguugguuga | 1200 |
| uuguagauau uggcuguua auugucaguu cagugugua aucgacgca ggcuuaugcg | 1260 |
| gaggagaaug uuucaugguu acuuauacua acauuaguuc uucauagggu gauagauug | 1320 |
| guccaauugg gugugaggag uucaguuaua uguuggau uuuuaggua gugggugug | 1380 |
| agcuugaacg cuucuuaau ugguggcugc uuuuaggccu acauggggu uuaaauuuu | 1440 |
| uacucucucu acaagguuuu uuccuagugu ccaaagagcu guuccucuuu ggacuaacag | 1500 |
| uuaaauuuac aaggggauuu agaggguucu gugggcaaau uuaaguuga acuaagauuc | 1560 |
| uaucuuggac aaccagcuau caccaggcuc gguagguuuu ucgccucuac cuauaaaucu | 1620 |
| ucccacuauu uugcuacaua gacggugug cucuuuuagc uguucuuagg uagcucgucu | 1680 |

-continued

```
gguuucgggg gucuuagcuu uggcucuccu ugcaaaguua uuucuaguua auucauuaug    1740
cagaagguau agggguuagu ccuugcuaua uuaugcuugg uuauaauuuu ucaucuuucc    1800
cuugcgguac uauaucuauu gcgccagguu ucaauuucua ucgccuauac uuuauuuggg    1860
uaaaugguuu ggcuaagguu gucugguagu aagguggagu ggguugggg cuagguuag     1920 c                                                                    1921
```

<210> SEQ ID NO 204
<211> LENGTH: 1744
<212> TYPE: RNA
<213> ORGANISM: Homo sapiens

<400> SEQUENCE: 204

```
uagggauaac agcgcaaucc uauucuagag uccauaucaa caauagggu uacgaccucg     60 auguuggauc aggacauccc gauggugcag ccgcuauuaa agguucguuu guucaacgau    120
uaaaguccua cgugaucuga guucagaccg aguaaaucca ggucguuuc uaucuaccuu    180 caaauuccuc ccguucuug ggugguguguggauaaauac uaaguugaga ugauaucauu    240
uacgggggaa ggcgcuuugu gaaguaggcc uuauuucucu uguccuuucg uacagggagg    300
aauuugaagu agauagaaac cgaccuggau uacuccgguc ugaaucaga ucacguagga    360 cuuuaaucgu ugaacaaacg aaccuuuaau agcggcugca ccaucgggau guccugaucc    420
aacaucgagg ucguaaaccc uauuguugau auggacucua gaauaggauu gcgcuguuau    480
cccuagggua acuguuccg uuggucaagu uauuggauca auugaguaua guaguucgcu    540
uugacuggug aagcuuagc auguacugcu cggaggguugg guucugcucc gaggucgccc    600
caaccgaaau uuuuaaugca gguugguag uuuaggaccu gugggguuugu uagguacugu    660 uugcauuaau aaauuaaagc uccauagggu cuucucgucu ugcuguguua ugcccgccuc    720
uucacgggca ggucaauuuc acugguuaaa aguaagagac agcugaaccc ucgggagcc    780 auucauacag gucccuauuu aaggaacaag ugauuaugcu accuuugcac gguaggggua    840
ccgcggccgu uaaacaugug ucacgggca ggcggugccu cuaauacugg ugaugcuaga    900
ggugauguuu uugguaaaca ggcgggguaa gauuugccga guuccuuuua cuuuuuuaa    960 ccuuuccuua ugagcaugcc ugguguggu ugacagugag gguaauaaug acuguuggu    1020 ugauguaga uauugggcug uuaauugca guucaguguu uuaaucugac gcaggcuuau    1080
gcggaggaga auguuuucau guuacuuaua cuaacauuag uucuucuaua gggugauaga    1140 uuggucccaau ugggugugag gaguucaguu auauguuugg gauuuuuag guaguggggg    1200 uugagcuuga acgcuuucuu aauggguggc ugcuuuagg ccuacuaugg uguuaaauu     1260 uuuuacucuc ucuacaaggu uuuuuccuag uguccaaaga gcuguccuc uuggacuaa    1320 caguuaaauu uacaagggga uuuagaggu ucugggggca aauuaaagu ugaacuaaga    1380 uucuaucuug acaaccagc uaucaccagg cucgguaggu uugucgccuc uaccauaaa    1440 ucuucccacu auuuugcuac auagacgggu gugcucuuuu agcuguucuu agguagcucg    1500
ucugguuucg ggggcuuag cuuuggcucu ccuugcaaag uuauuucuag uuaauucauu    1560
augcagaagg uauagggguu agccuugcu auauuaugcu ugguuauaau uuucaucuu    1620 ucccuugcgg uacuauaucu auugcgccag guucaauuu cuaucgccua acuuuauuu    1680 ggguaaaugg uuuggcuaag guuguucuggu aguaaggugg aguggguuug gggcuagguu    1740
uagc                                                                 1744
```

<210> SEQ ID NO 205
<211> LENGTH: 1854
<212> TYPE: RNA
<213> ORGANISM: Homo sapiens

<400> SEQUENCE: 205

```
gaacucggca aaucuuaccc cgccuguuua ccaaaaacau caccucuagc aucaccagua      60
uuagaggcac cgccugccca gugacacaug uuuaacggcc gcgguacccu aaccgugcaa     120
agguagcaua aucacuuguu ccuuaaauag ggaccuguau gaauggcucc acgaggguuc     180
agcugucucu acuuuuaac cagugaaauu gaccugcccg ugaagaggcg ggcaugacac       240
agcaagacga gaagacccua uggagcuuua auuuauuaau gcaaacagua ccuaacaaac     300
ccuguucuug gguggugug gguauaaauac uaaguugaga ugauaucauu uacggggaa       360
ggcgcuuugu gaaguaggcc uuauuucucu uguccuuucg uacagggagg aauuugaagu     420
agauagaaac cgaccuggau uacuccgguc ugaaucaga ucacguagga cuuuaaucgu      480
ugaacaaacg aaccuuuaau agcggcugca ccaucgggau guccugaucc aacaucgagg     540
ucguaaaccc uauuguugau auggacucua gaauaggauu gcgcuguuau cccuagggua     600
acuuguuccg uuggucaagu uauuggauca auugaguaua guagguucgcu uugacugguug   660
aagucuuagc auguacugcu cggagguugg guucugcucc gaggucgccc caaccgaaau     720
uuuuaaugca gguuugguag uuuuaggaccu gugggguuugu uagguacugu uugcauuaau   780
aaauuaaagc uccauagggu cuucucgucu ugcuguguua ugcccgccuc uucacgggca     840
ggucaauuuc acugguuaaa aguaagagac agcugaaccc ucguggagcc auucauacag     900
gucccuauuu aaggaacaag ugauuaugcu accuuugcac gguuagggua ccgcggccgu     960
uaaacaugug ucacugggca ggcggugccu cuaauacugg ugaugcuaga ggugauguuu    1020
uugguaaaca ggcgggguaa gauuugccga guuccuuuua cuuuuuuaa ccuuuccuua     1080
ugagcaugcc uguguuggu ugacagugag gguaauaaug acuuguuggu ugauuguaga     1140
uauugggcug uuaauuguca guucagguu uuaaucugac gcaggcuuau gcggaggaga     1200
auguuucau guuacuuaua cuaacauuag uucuucuaua gggugauaga uugguccaau      1260
uggguguag gaguucaguu auauguuugg gauuuuuag guagugggug uugagcuuga       1320
acgcuuucuu aauggugggc ugcuuuuagg ccuacauggg guguuaaauu uuuuacucuc    1380
ucuacaaggu uuuuuccuag uguccaaaga gcuguuccuc uuuggacuaa caguuaaauu     1440
uacaaggga uuuagagggu ucuguggca aauuuaaagu ugaacuaaga uucuaucuug      1500
gacaaccagc uaucaccagg cucgguaggu uugucgccuc uaccauaaaa ucuucccacu    1560
auuuugcuac auagacgggu gugcucuuuu agcuguucuu agguagcucg ucugguuucg    1620
ggggucuuag cuuuggcucu ccuugcaaag uuauuucuag uuaauucauu augcagaagg    1680
uauaggggguu aguccuugcu auauuaugcu ugguuauaau uuucaucuu ucccuugcgg    1740
uacuauaucu auucgccag guuucaauuu cuaucgccua acuuuauuu ggguaaaugg      1800
uuuggcuaag guugucuggu aguaaggugg aguggguuug gggcuagguu uagc           1854
```

ANTISENSE OLIGONUCLEOTIDES FOR TREATMENT OF CANCER STEM CELLS

CROSS-REFERENCE TO RELATED APPLICATIONS

This application is a National Phase filing under 35 U.S.C. §371 of International Application No. PCT/US2014/029606, filed Mar. 14, 2014, which claims the priority benefit of U.S. Provisional Patent Application Ser. No. 61/785,269, filed Mar. 14, 2013, U.S. Provisional Patent Application Ser. No. 61/790,072, filed Mar. 15, 2013, and U.S. Provisional Patent Application Ser. No. 61/937,438, filed Feb. 7, 2014, the entire contents of each of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 70740200300SeqList.txt, date recorded: Dec. 18, 2015, size: 63 KB).

FIELD OF THE INVENTION

This invention relates to oligonucleotides complementary to a non-coding chimeric mitochondrial RNA and their use in methods of treating and preventing metastasis or relapse of a cancer in an individual previously treated for cancer. The invention also relates to oligonucleotides complementary to a non-coding chimeric mitochondrial RNA and their use in treating a refractory cancer (e.g., a refractory HPV-associated cancer) in an individual.

BACKGROUND OF THE INVENTION

Cancer is a cellular malignancy whose unique trait, loss of normal control of cell cycle, results in unregulated growth, lack of differentiation, and ability to invade other tissues and metastasize. Carcinogenesis is a multi-step process by which a normal cell is transformed in a malignant cell (McKinnell et al., "The Biology Basis of Cancer", Ch. 3, 1998). The etiology of cancer is complex and includes alteration of the cell cycle regulation, chromosomal abnormalities and chromosomes breakage. Infectious agents (e.g., oncogenic viruses), chemicals, radiation (e.g., ultraviolet or ionizing radiation) and immunological disorders are thought to be the major causes of carcinogenesis (McKinnell et al., "The Biological Basis of Cancer, Ch. 3, 1998).

Recent evidence supports the view that tumors are organized in a hierarchy of heterogeneous cell populations with different biological properties. Two models have been proposed to account for this heterogeneity within tumors and for tumor growth. One such model is based on cancer stem cells (CSCs) which are thought to be responsible for aspects of cancer such as initiation, progression, metastasis, and recurrence. See Chen et al., *Acta Pharmacol Sin.*, 34(6):732-740, 2013; Ponti et al., *Cancer Res*, 65(13):5506-11, 2005; Singh et al., *Cancer Res*, 63:5821-5828, 2003; and Feng et al., *Oncology Reports*, 22:1129-1134, 2009. Although CSCs generally represent a very small population of the overall tumor population, they are generally regarded as a self-renewing initiation subpopulation of tumor cells or a small population of cancer cells that are capable of giving rise to new tumors. CSCs have been identified in a number of cancers including, but not limited to, breast, brain, blood, liver, kidney, cervical ovarian, colon, and lung cancers among others. See Ponti et al., *Cancer Res*, 65(13):5506-11, 2005; Feng et al., *Oncology Reports*, 22:1129-1134, 2009; Zhang et al., *Cancer Res*, 68(11):4311:4320, 2008: Singh et al., *Cancer Res*, 63:5821-5828, 2003; Clarke et al., *Cancer Res*, 66:9339, 2006; Sendurai et al., *Cell*, 133:704, 2008; Ohata et al., *Cancer Res*, 72:5101, 2012; and Mukhopapadhyay et al., *Plos One*, 8(11):e78725, 2013).

Surgical resection of tumor(s) or metastases arising from a primary tumor(s) followed by systemic administration of anti-cancer therapy is the established clinical protocol for treatment of several cancers. Although successful for treatment of some cancer types, a well-known complication of cancer treatment is the survival of residual tumor cells or CSCs that are not effectively removed which can result in relapse after remission, with the cancer returning at the primary site of tumor formation or at distant sites due to metastasis. Recently, it was found that CSCs may also contribute to relapse after remission due to resistance to chemotherapy. See Domingo-Domenech et al., *Cancer Cell*, 22(3):373, 2012. Therefore, there is a need for development of therapeutic agents that can target cells which contribute to relapse and metastasis (e.g., CSCs). Discovery of such therapeutic agents may allow for the development of treatment useful for preventing recurrence of cancer after remission (i.e., relapse) or preventing the spread of the primary tumour to secondary sites (i.e., metastasis). See Clarke et al., *Cancer Res*, 66:9339, 2006.

All references cited herein, including patent applications, patent publications, and scientific literature, are herein incorporated by reference as if each individual reference were specifically and individually indicated to be incorporated by reference.

SUMMARY OF THE INVENTION

The invention provided herein discloses, inter alia, methods for suppressing metastasis of a cancer in an individual comprising administering to the individual an effective amount of one or more oligonucleotide complementary to an antisense non-coding chimeric mitochondrial RNA (ASncmtRNA) molecule or a sense non-coding chimeric mitochondrial RNA (SncmtRNA) molecule, wherein the oligonucleotide is able to hybridize with the chimeric mitochondrial RNA molecules to form a stable duplex, and wherein the individual has been previously treated for cancer with a therapy. In some embodiments, the oligonucleotide is sufficiently complementary to a human non-coding chimeric mitochondrial RNA molecule comprising: an antisense 16S mitochondrial ribosomal RNA covalently linked at its 5' end to the 3' end of a polynucleotide with an inverted repeat sequence or a sense 16S mitochondrial ribosomal RNA covalently linked at its 5' end to the 3' end of a polynucleotide with an inverted repeat sequence. In any of the embodiments herein, the oligonucleotide can be complementary to the ASncmtRNA molecule encoded by a nucleotide sequence selected from the group consisting of SEQ ID NO:4, SEQ ID NO:5, and SEQ ID NO:6. In any of the embodiments herein, the oligonucleotide can be at least 85% complementary to the ASncmtRNA molecule encoded by a nucleotide sequence selected from the group consisting of SEQ ID NO:4, SEQ ID NO:5, and SEQ ID NO:6. In any of the embodiments herein, the one or more oligonucleotide can comprise a nucleotide sequence selected from the group consisting of SEQ ID NOs:7-198. In some embodiments, the one or more oligonucleotide comprises a nucleic acid sequence selected from the group consisting of SEQ ID NOs:36, 197 and 198. In any of the embodiments herein, the oligonucleotide can be administered in combination with at least one anti-cancer agent. In a further embodiment, the at least one anti-cancer agent is selected from the group consisting of remicade, docetaxel, celecoxib, melphalan, dexamethasone, steroids, gemcitabine, cisplatinum, temozolomide, etoposide, cyclophosphamide, temodar, carboplatin, procarbazine, gliadel, tamoxifen, topotecan, methotrexate, gefitinib, taxol, taxotere, fluorouracil, leucovorin, irinotecan, xeloda, CPT-11, interferon alpha, pegylated interferon alpha, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib, bisphosphonate, arsenic trioxide, vincristine, doxorubicin, paclitaxel, ganciclovir, adriamycin, estrainustine sodium phosphate, sulindac, and etoposide. In some embodiments, the oligonucleotide and the at least one anti-cancer agent is administered sequentially. In some embodiments, the oligonucleotide and the at least one anti-cancer agent is administered simultaneously. In any of the embodiments herein, the oligonucleotide can be administered in combination with a radiation therapy. In any of the embodiments herein, the oligonucleotide can be administered in combination with surgery. In any of the embodiments herein, the oligonucleotide can be administered in combination with an allogenic stem cell transplant therapy. In any of the embodiments herein, the oligonucleotide can be administered in combination with an autologous stem cell transplant therapy. In any of the embodiments herein, the individual may have been previously treated for cancer with a therapy comprising chemotherapy, radiation therapy, surgery, or combinations thereof. In any of the embodiments herein, the cancer in the individual may have relapsed after treatment with one or more of bortezomib, cyclophosphamide, dexamethasone, doxorubicin, interferon-alpha, lenalidomide, melphalan, pegylated interferon-alpha, prednisone, thalidomide, and vincristine. In any of the embodiments herein, wherein the cancer can be a solid cancer. In a further embodiment, the solid cancer is bladder cancer, brain cancer, breast cancer, cervical cancer, colon cancer, endometrial cancer, esophageal cancer, gastric cancer, liver and bile duct cancer, lung cancer, melanoma, oral cancer, ovarian cancer, pancreatic cancer, pharynx cancer, prostate cancer, renal cancer, testicular cancer, or thyroid cancer. In any of the embodiments herein, wherein the cancer can be a non-solid cancer. In a further embodiment, the non-solid cancer is multiple myeloma, leukemia, or lymphoma. In any of the embodiments herein, the oligonucleotide can reduce the number of cancer stem cells in the individual as compared to an individual not administered the oligonucleotide. In any of the embodiments herein, the oligonucleotide can inhibit tumor growth and/or metastasis in the individual as compared to an individual not administered the oligonucleotide.

In one aspect, the invention provided herein discloses, methods for preventing relapse of cancer in an individual comprising administering to the individual an effective amount of one or more oligonucleotide complementary to an antisense non-coding chimeric mitochondrial RNA (ASncmtRNA) molecule or a sense non-coding chimeric mitochondrial RNA (SncmtRNA) molecule, wherein the oligonucleotide is able to hybridize with the chimeric mitochondrial RNA molecules to form a stable duplex, and wherein the individual has been previously treated for cancer with a therapy. In a further embodiment, the oligonucleotide is sufficiently complementary to a human non-coding chimeric mitochondrial RNA molecule comprising: an antisense 16S mitochondrial ribosomal RNA covalently linked at its 5' end to the 3' end of a polynucleotide with an inverted repeat sequence or a sense 16S mitochondrial ribosomal RNA covalently linked at its 5' end to the 3' end of a polynucleotide with an inverted repeat sequence. In any of the embodiments herein, the oligonucleotide can be complementary to the ASncmtRNA molecule encoded by a nucleotide sequence selected from the group consisting of SEQ ID NO:4, SEQ ID NO:5, and SEQ ID NO:6. In any of the embodiments herein, the oligonucleotide can be at least 85% complementary to the ASncmtRNA molecule encoded by a nucleotide sequence selected from the group consisting of SEQ ID NO:4, SEQ ID NO:5, and SEQ ID NO:6. In any of the embodiments herein, the one or more oligonucleotide can comprise a nucleotide sequence selected from the group consisting of SEQ ID NOs:7-198. In some embodiments, the one or more oligonucleotide comprises a nucleic acid sequence selected from the group consisting of SEQ ID NOs:36, 197 and 198. In any of the embodiments herein, the oligonucleotide can be administered in combination with at least one anti-cancer agent. In a further embodiment, the at least one anti-cancer agent is selected from the group consisting of remicade, docetaxel, celecoxib, melphalan, dexamethasone, steroids, gemcitabine, cisplatinum, temozolomide, etoposide, cyclophosphamide, temodar, carboplatin, procarbazine, gliadel, tamoxifen, topotecan, methotrexate, gefitinib, taxol, taxotere, fluorouracil, leucovorin, irinotecan, xeloda. CPT-11, interferon alpha, pegylated interferon alpha, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib, bisphosphonate, arsenic trioxide, vincristine, doxorubicin, paclitaxel, ganciclovir, adriamycin, estrainustine sodium phosphate, sulindac, and etoposide. In some embodiments, the oligonucleotide and the at least one anti-cancer agent is administered sequentially. In some embodiments, the oligonucleotide and the at least one anti-cancer agent is administered simultaneously. In any of the embodiments herein, the oligonucleotide can be administered in combination with a radiation therapy. In any of the embodiments herein, the oligonucleotide can be administered in combination with surgery. In any of the embodiments herein, the oligonucleotide can be administered in combination with an allogenic stem cell transplant therapy. In any of the embodiments herein, the oligonucleotide can be administered in combination with an autologous stem cell transplant therapy. In any of the embodiments herein, the individual may have been previously treated for cancer with a therapy comprising chemotherapy, radiation therapy, surgery, or combinations thereof. In any of the embodiments herein, the cancer in the individual may have relapsed after treatment with one or more of bortezomib, cyclophosphamide, dexamethasone, doxorubicin, interferon-alpha, lenalidomide, melphalan, pegylated interferon-alpha, prednisone, thalidomide, and vincristine. In any of the embodiments herein, wherein the cancer can be a solid cancer. In a further embodiment, the solid cancer is bladder cancer, brain cancer, breast cancer, cervical cancer, colon cancer, endometrial cancer, esophageal cancer, gastric cancer, liver and bile duct cancer, lung cancer, melanoma, oral cancer, ovarian cancer, pancreatic cancer, pharynx cancer, prostate cancer, renal cancer, testicular cancer, or thyroid cancer. In any of the embodiments herein, wherein the cancer can be a non-solid cancer. In a further embodiment, the non-solid cancer is multiple myeloma, leukemia, or lymphoma. In any of the embodiments herein, the oligonucleotide can reduce the number of cancer stem cells in the individual as compared to an individual not administered the oligonucleotide. In any of the embodiments herein, the oligonucleotide can inhibit tumor growth and/or metastasis in the individual as compared to an individual not administered the oligonucleotide.

In yet another aspect, the invention provided herein discloses, methods for the treatment of metastatic cancer in an individual comprising administering to the individual an effective amount of one or more oligonucleotide complementary to an antisense non-coding chimeric mitochondrial RNA (ASncmtRNA) molecule or a sense non-coding chimeric mitochondrial RNA (SncmtRNA) molecule, wherein the oligonucleotide is able to hybridize with the chimeric mitochondrial RNA molecules to form a stable duplex, and wherein the individual has been previously treated for cancer with a therapy. In a further embodiment, the oligonucleotide is sufficiently complementary to a human non-coding chimeric mitochondrial RNA molecule comprising: an antisense 16S mitochondrial ribosomal RNA covalently linked at its 5' end to the 3' end of a polynucleotide with an inverted repeat sequence or a sense 16S mitochondrial ribosomal RNA covalently linked at its 5' end to the 3' end of a polynucleotide with an inverted repeat sequence. In any of the embodiments herein, the oligonucleotide can be complementary to the ASncmtRNA molecule encoded by a nucleotide sequence selected from the group consisting of SEQ ID NO:4. SEQ ID NO:5, and SEQ ID NO:6. In any of the embodiments herein, the oligonucleotide can be at least 85% complementary to the ASncmtRNA molecule encoded by a nucleotide sequence selected from the group consisting of SEQ ID NO:4, SEQ ID NO:5, and SEQ ID NO:6. In any of the embodiments herein, the one or more oligonucleotide can comprise a nucleotide sequence selected from the group consisting of SEQ ID NOs:7-198. In some embodiments, the one or more oligonucleotide comprises a nucleic acid sequence selected from the group consisting of SEQ ID NOs:36, 197 and 198. In any of the embodiments herein, the oligonucleotide can be administered in combination with at least one anti-cancer agent. In a further embodiment, the at least one anti-cancer agent is selected from the group consisting of remicade, docetaxel, celecoxib, melphalan, dexamethasone, steroids, gemcitabine, cisplatinum, temozolomide, etoposide, cyclophosphamide, temodar, carboplatin, procarbazine, gliadel, tamoxifen, topotecan, methotrexate, gefitinib, taxol, taxotere, fluorouracil, leucovorin, irinotecan, xeloda, CPT-11, interferon alpha, pegylated interferon alpha, capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib, bisphosphonate, arsenic trioxide, vincristine, doxorubicin, paclitaxel, ganciclovir, adriamycin, estrainustine sodium phosphate, sulindac, and etoposide. In some embodiments, the oligonucleotide and the at least one anti-cancer agent is administered sequentially. In some embodiments, the oligonucleotide and the at least one anti-cancer agent is administered simultaneously. In any of the embodiments herein, the oligonucleotide can be administered in combination with a radiation therapy. In any of the embodiments herein, the oligonucleotide can be administered in combination with surgery. In any of the embodiments herein, the oligonucleotide can be administered in combination with an allogenic stem cell transplant therapy. In any of the embodiments herein, the oligonucleotide can be administered in combination with an autologous stem cell transplant therapy. In any of the embodiments herein, the individual may have been previously treated for cancer with a therapy comprising chemotherapy, radiation therapy, surgery, or combinations thereof. In any of the embodiments herein, the metastatic cancer in the individual may have relapsed after treatment with one or more of bortezomib, cyclophosphamide, dexamethasone, doxorubicin, interferon-alpha, lenalidomide, melphalan, pegylated interferon-alpha, prednisone, thalidomide, and vincristine. In any of the embodiments herein, wherein the cancer can be a solid cancer. In a further embodiment, the solid cancer is bladder cancer, brain cancer, breast cancer, cervical cancer, colon cancer, endometrial cancer, esophageal cancer, gastric cancer, liver and bile duct cancer, lung cancer, melanoma, oral cancer, ovarian cancer, pancreatic cancer, pharynx cancer, prostate cancer, renal cancer, testicular cancer, or thyroid cancer. In any of the embodiments herein, wherein the cancer can be a non-solid cancer. In a further embodiment, the non-solid cancer is multiple myeloma, leukemia, or lymphoma. In any of the embodiments herein, the oligonucleotide can reduce the number of cancer stem cells in the individual as compared to an individual not administered the oligonucleotide. In any of the embodiments herein, the oligonucleotide can inhibit tumor growth and/or metastasis in the individual as compared to an individual not administered the oligonucleotide.

In yet another aspect, the invention provided herein discloses, methods for the treatment of a refractory cancer (e.g., a refractory HPV-associated cancer) in an individual comprising administering to the individual an effective amount of one or more oligonucleotide complementary to an antisense non-coding chimeric mitochondrial RNA (ASncmtRNA) molecule or a sense non-coding chimeric mitochondrial RNA (SncmtRNA) molecule, wherein the oligonucleotide is able to hybridize with the chimeric mitochondrial RNA molecules to form a stable duplex. In a further embodiment, the oligonucleotide is sufficiently complementary to a human non-coding chimeric mitochondrial RNA molecule comprising: an antisense 16S mitochondrial ribosomal RNA covalently linked at its 5' end to the 3' end of a polynucleotide with an inverted repeat sequence or a sense 16S mitochondrial ribosomal RNA covalently linked at its 5' end to the 3' end of a polynucleotide with an inverted repeat sequence. In any of the embodiments herein, the oligonucleotide can be complementary to the ASncmtRNA molecule encoded by a nucleotide sequence selected from the group consisting of SEQ ID NO:4, SEQ ID NO:5, and SEQ ID NO:6. In any of the embodiments herein, the oligonucleotide can be at least 85% complementary to the ASncmtRNA molecule encoded by a nucleotide sequence selected from the group consisting of SEQ ID NO:4, SEQ ID NO:5, and SEQ ID NO:6. In any of the embodiments herein, the one or more oligonucleotide can comprise a nucleotide sequence selected from the group consisting of SEQ ID NOs:7-198. In some embodiments, the one or more oligonucleotide comprises a nucleic acid sequence selected from the group consisting of SEQ ID NOs:36, 197 and 198. In any of the embodiments herein, the oligonucleotide can be administered in combination with at least one anti-cancer agent. In some embodiments, the oligonucleotide and the at least one anti-cancer agent is administered sequentially. In some embodiments, the oligonucleotide and the at least one anti-cancer agent is administered simultaneously. In any of the embodiments herein, the oligonucleotide can be administered in combination with a radiation therapy. In any of the embodiments herein, the oligonucleotide can be administered in combination with surgery. In any of the embodiments herein, the oligonucleotide can reduce the number of cancer stem cells in the individual as compared to an individual not administered the oligonucleotide. In any of the embodiments herein, the oligonucleotide can inhibit tumor growth and/or metastasis in the individual as compared to an individual not administered the oligonucleotide.

In another aspect, the invention herein provides kits comprising one or more oligonucleotide complementary to an antisense non-coding chimeric mitochondrial RNA (ASncmtRNA) molecule or a sense non-coding chimeric mitochondrial RNA (SncmtRNA) molecule and instructions for practicing any method disclosed herein.

DETAILED DESCRIPTION

Figure 1:
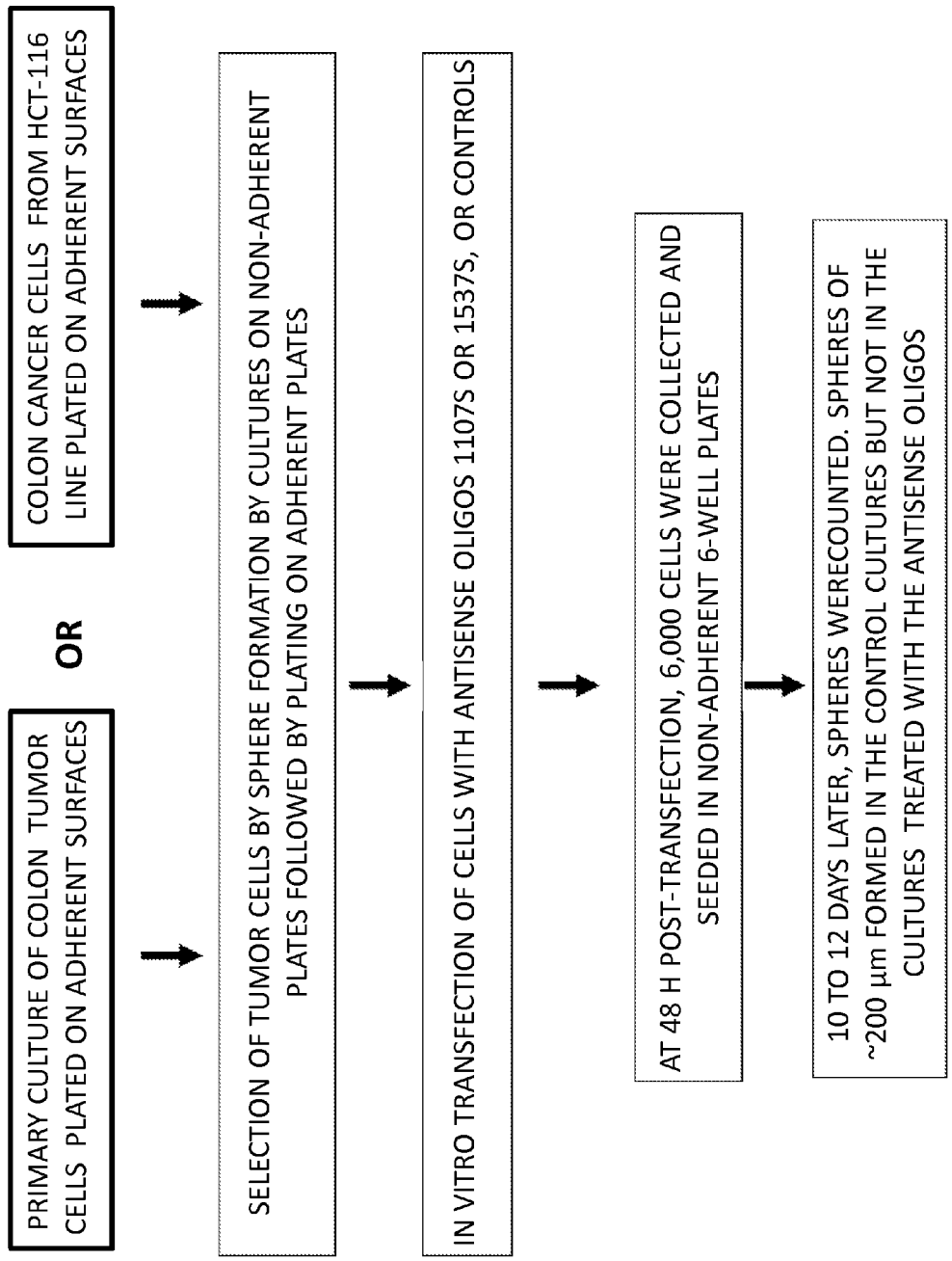
FIG. 1 depicts a general scheme of the experimental procedure and the assay utilized herein to measure the effect of antisense oligonucleotides targeted to ASncmtRNA on the number of spheres formed in colon cancer cells, based on the specific ability of cancer stem cells to form these spheroid bodies.

The invention provided herein discloses, inter alia, compositions comprising one or more oligonucleotide complementary to an antisense non-coding chimeric mitochondrial RNA (ASncmtRNA) molecule or a sense non-coding chimeric mitochondrial RNA (SncmtRNA) molecule and uses thereof for suppressing metastasis of a cancer in an individual. In certain embodiments, the invention provides compositions comprising one or more oligonucleotide complementary to an ASncmtRNA molecule or a SncmtRNA molecule and uses thereof for treating or preventing relapse of a cancer in an individual. In certain embodiments, the invention provides compositions comprising one or more oligonucleotide complementary to an ASncmtRNA molecule or a SncmtRNA molecule and uses thereof for treating metastatic cancer in an individual. In certain embodiments, the invention provides compositions comprising one or more oligonucleotide complementary to an ASncmtRNA molecule or a SncmtRNA molecule and uses thereof for treating a refractory cancer (e.g., a refractory HPV-associated cancer) in an individual. In some of the embodiments herein, the individual has been previously treated for cancer with a therapy (e.g., chemotherapy, radiation therapy, surgery or combinations thereof).

I. General Techniques

The practice of the present invention will employ, unless otherwise indicated, conventional techniques of molecular biology, microbiology, cell biology, biochemistry, nucleic acid chemistry, and immunology, which are well known to those skilled in the art. Such techniques are explained fully in the literature, such as, *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); *Current Protocols in Molecular Biology* (F. M. Ausubel et al., eds., 1987, including supplements through 2001); PCR: The Polymerase Chain Reaction, (Mullis et al., eds., 1994); Harlow and Lane (1988) *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry* John Wiley & Sons. Inc., New York, 2000), *Handbook of Experimental Immunology*, 4th edition (D. M. Weir & C. C. Blackwell, eds., Blackwell Science Inc., 1987); and *Gene Transfer Vectors for Mammalian Cells* (J. M. Miller & M. P. Calos. eds., 1987). Other useful references include Harrison's *Principles of Internal Medicine* (McGraw Hill; J. Isseleacher et al., eds.), Dubois' Lupus Erythematosus (5th ed.; D. J. Wallace and B. H. Hahn, eds.

II. Definitions

Before describing the present invention in detail, it is to be understood that this invention is not limited to particular compositions or biological systems, which can, of course, vary. It is also to be understood that the terminology used herein is for the purpose of describing particular embodiments only, and is not intended to be limiting.

As used herein, the singular form "a", "an", and "the" includes plural references unless indicated otherwise. Thus, for example, reference to "an oligonucleotide" optionally includes a combination of two or more such oligonucleotides, and the like.

It is understood that aspects and embodiments of the invention described herein include "comprising," "consisting," and "consisting essentially of" aspects and embodiments.

An "isolated" nucleic acid molecule (e.g., "isolated oligonucleotide") is a nucleic acid molecule that is identified and separated from at least one contaminant nucleic acid molecule with which it is ordinarily associated in the natural source of the nucleic acid. An isolated nucleic acid molecule is other than in the form or setting in which it is found in nature. Isolated nucleic acid molecules therefore are distinguished from the nucleic acid molecule as it exists in natural cells.

As used herein, the term "oligonucleotide complementary to an antisense non-coding chimeric mitochondrial RNA" or "oligonucleotide complementary to a sense non-coding chimeric mitochondrial RNA" refers to a nucleic acid having sufficient sequence complementarity to a target antisense non-coding chimeric mitochondrial RNA or a target sense non-coding chimeric mitochondrial RNA, respectively. An oligonucleotide "sufficiently complementary" to a target antisense non-coding chimeric mitochondrial RNA or a target sense non-coding chimeric mitochondrial RNA means that the oligonucleotide has a sequence sufficient to hybridize with the chimeric mitochondrial RNA molecules to form a stable duplex.

The term "oligonucleotide" refers to a short polymer of nucleotides and/or nucleotide analogs. An "oligonucleotide composition" of the invention includes any agent, compound or composition that contains one or more oligonucleotides, and includes, e.g., compositions comprising both single stranded and/or double stranded (ds) oligonucleotides, including, e.g., single stranded RNA, single stranded DNA, DNA/DNA and RNA/DNA hybrid oligonucleotides, as well as derivatized/modified oligonucleotides thereof. Such "oligonucleotide compositions" may also include amplified oligonucleotide products, e.g., polymerase chain reaction (PCR) products. An "oligonucleotide compositions" of the invention may also include art-recognized compositions designed to mimic the activity of oligonucleotides, such as peptide nucleic acid (PNA) molecules.

The phrase "corresponds to" or "sequence corresponding to" as it relates to RNA described herein (e.g., ASncmtRNA), indicates that the RNA has a sequence that is identical to or substantially the same as an RNA, or an RNA encoded by an analogous DNA, described herein. For example, an ASncmtRNA that corresponds to SEQ ID NO:4 indicates that the ASncmtRNA has a sequence that is identical to or substantially the same as the RNA of SEQ ID NO:203 or the RNA encoded by the analogous DNA of SEQ ID NO:4.

"Percent (%) nucleic acid sequence identity" or "percent (%) complementary" with respect to a reference nucleotide sequence (e.g., SncmtRNA sequence or ASncmtRNA sequence) is defined as the percentage of nucleic acid residues in a candidate sequence (e.g., oligonucleotide sequence) that are identical with the nucleic acid residues in the reference nucleotide sequence, after aligning the sequences and introducing gaps, if necessary, to achieve the maximum percent sequence identity, and not considering any conservative substitutions as part of the sequence identity. Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For example, the % nucleic acid sequence identity of a given nucleic acid sequence A to, with, or against a given nucleic acid sequence B (which can alternatively be phrased as a given nucleic acid sequence A that has or comprises a certain % nucleic acid sequence identity to, with, or against a given nucleic acid sequence B) is calculated as follows:

$$100 \text{ times the fraction } X/Y$$

where X is the number of nucleic acid residues scored as identical matches by the sequence in that program's alignment of A and B, and where Y is the total number of nucleic acid residues in B. It will be appreciated that where the length of nucleic acid sequence A is not equal to the length of nucleic acid sequence B, the % nucleic acid sequence identity of A to B will not equal the % nucleic acid sequence identity of B to A.

A "disorder" or "disease" is any condition that would benefit from treatment with a substance/molecule or method of the invention. This includes chronic and acute disorders or diseases including those pathological conditions which predispose the mammal to the disorder in question. In one embodiment, the disorder or disease is cancer. In another embodiment, the disorder or disease is metastatic cancer.

The term "cancer" refers to or describes the physiological condition in mammals that is typically characterized by unregulated cell growth/proliferation. Examples of cancer include but are not limited to, lymphoma, blastoma, sarcoma, and leukemia.

The terms "metastatic cancer" or "cancer metastasis" refer to a primary cancer capable of metastasis or cancer which has spread (i.e., metastasized) from a primary cancer, primary cancerous tissue or primary cancerous cells (e.g., cancer stem cells) from one part of of the body to one or more other parts of the body to form a secondary cancer or secondary cancers. Metastatic cancer or cancer metastasis also refer to locally advanced cancer that has spread from a primary cancer to nearby tissue(s) or lymph node(s). Metastatic cancer includes tumors that are defined as being high grade and/or high stage, for example tumors with a Gleason score of 6 or higher in prostate cancer are more likely to metastasize. Metastatic cancer also refers to tumors defined by one or more molecular markers that correlate with the metastasis.

The terms "relapsed cancer", "relapse of a cancer", "cancer relapse", or "tumor relapse" refer to the return or reappearance of cancer after a period of improvement. Typically the period of improvement is after administration of a therapy that resulted in the decrease of or disappearance of signs and symptoms of cancer. The period of improvement can be the decrease or disappearance of all signs and symptoms of cancer. The period of improvement can also be the decrease or disappearance of some, but not all, signs and symptoms of cancer. In some embodiments, the relapsed cancer is a cancer that has become unresponsive or partially unresponsive to a drug or a therapy. For example and without limitation, relapsed cancer includes cancer in patients whose first progression occurs in the absence of any treatment following successful treatment with a drug or a therapy; cancer in patients who progress on a treatment, or within 60 days of the treatment; and cancer in patients who progress while receiving treatment.

The terms "cancer stem cell". "cancer stem cells" or "CSCs" as used herein refer to a subpopulation of tumor cells or cancer cells. Cancer stem cells possess characteristics associated with normal stem cells, such as the ability to give rise to different cell types found in a particular cancer or tumor. Cancer stem cells have the capacity to drive the production or formation of a tumor or tumors through self-renewal and/or differentiation. Cancer stem cells have been identified in a number of cancers including, but not limited to, breast, brain, blood, liver, kidney, cervical, ovarian, colon, and lung cancers among others.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing or suppressing metastasis, decreasing the rate of disease progression, amelioration or palliation of the disease state, and remission or improved prognosis. In some embodiments, oligonucleotides described herein are used to prevent or suppress metastasis. An individual is successfully "treated", for example, using an oligonucleotide of the invention if the individual shows observable and/or measurable reduction in or absence of one or more of the following: reduction in the number of cancer cells or absence of the cancer cells; reduction in the tumor size: inhibition (i.e., slow to some extent and preferably stop) of cancer cell infiltration into peripheral organs including the spread of cancer into soft tissue and bone; inhibition (i.e., slow to some extent and preferably stop) of tumor metastasis; inhibition, to some extent, of tumor growth or tumor relapse; and/or relief to some extent, one or more of the symptoms associated with the specific cancer; reduced morbidity and mortality, and improvement in quality of life issues.

As used herein, the term "prevention" includes providing prophylaxis with respect to occurrence or recurrence of a disease in an individual. An individual may be predisposed to, susceptible to a disorder, or at risk of developing a disorder, but has not yet been diagnosed with the disorder. In some embodiments, oligonucleotides described herein are used to prevent or suppress metastasis.

As used herein, an individual "at risk" of developing a disorder may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of cancer (e.g., metastatic cancer), as known in the art. An individual having one or more of these risk factors has a higher probability of developing the disorder than an individual without one or more of these risk factors.

An "individual" or "subject" can be a vertebrate, a mammal, or a human. Mammals include, but are not limited to, farm animals (such as cows), sport animals, pets (such as horses), primates, mice and rats. Individuals also include companion animals including, but not limited to, dogs and cats. In one aspect, an individual is a human.

A "healthcare professional," as used herein, can include, without limitation, doctors, nurses, physician assistants, lab technicians, research scientists, clerical workers employed by the same, or any person involved in determining, diagnosing, aiding in the diagnosis or influencing the course of treatment for the individual.

An "effective amount" refers to an amount of therapeutic compound, such as an oligonucleotide or other anticancer therapy, administered to an individual, either as a single dose or as part of a series of doses, which is effective to produce a desired therapeutic or prophylactic result.

A "therapeutically effective amount" is at least the minimum concentration required to effect a measurable improvement of a particular disorder. A therapeutically effective amount herein may vary according to factors such as the disease state, age, sex, and weight of the patient, and the ability of the oligonucleotide to elicit a desired response in the individual. A therapeutically effective amount may also be one in which any toxic or detrimental effects of the oligonucleotide are outweighed by the therapeutically beneficial effects. In the case of cancer, the therapeutically effective amount of the oligonucleotide may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis: inhibit, to some extent, tumor growth; and/or relieve to some extent one or more of the symptoms associated with the cancer. To the extent the oligonucleotide may prevent growth and/or kill existing cancer cells, it may be cytostatic and/or cytotoxic.

A "prophylactically effective amount" refers to an amount effective, at the dosages and for periods of time necessary, to achieve the desired prophylactic result. For example, a prophylactically effective amount of the oligonucleotides of the present invention is at least the minimum concentration that prevents or attenuates the development of at least one symptom of metastatic cancer.

Administration "in combination with" one or more further therapeutic agents includes simultaneous (concurrent) and consecutive administration in any order.

The term "pharmaceutical formulation" refers to a preparation that is in such form as to permit the biological activity of the active ingredient to be effective, and that contains no additional components that are unacceptably toxic to a subject to which the formulation would be administered. Such formulations are sterile.

A "sterile" formulation is aseptic or free from all living microorganisms and their spores.

The term "package insert" is used to refer to instructions customarily included in commercial packages of therapeutic products, that contain information about the indications, usage, dosage, administration, contraindications and/or warnings concerning the use of such therapeutic products.

The term "about" as used herein refers to the usual error range for the respective value readily known to the skilled person in this technical field.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

III. Oligonucleotides and other Anti-Cancer Therapies

Human cells express a number of unique chimeric mitochondrial RNA molecules. These molecules are non-coding (i.e., they are not known to serve as a template for the translation of a protein) and comprise the 16S mitochondrial ribosomal RNA covalently linked at the 5' end to an inverted repeat sequence. Chimeric mitochondrial RNA molecules are found in two forms: sense and antisense.

The sense chimeric non-coding mitochondrial RNA (SncmtRNA) molecule corresponds to the 16S mitochondrial ribosomal RNA transcribed from the "H-strand" of the circular mitochondrial genome. Covalently linked to the 5' end of this RNA molecule is a nucleotide sequence or inverted repeat sequence corresponding to an RNA transcribed from the "L-strand" of the mitochondrial 16S gene. The size of the inverted repeat sequence in the SncmtRNA can vary from about 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, or 800 nucleotides or more to between about 100-200, 150-250, 200-300, 250-350, 400-500, 450-550, 500-600, 550-650, 600-700, 650-750, or 700-800 nucleotides or more, including any number in between these values. In one embodiment, the inverted repeat sequence in the SncmtRNA corresponds to a fragment of 815 nucleotides of the RNA transcribed from the L-strand of the 16S gene of the mitochondrial genome. In another embodiment, the inverted repeat sequence in the SncmtRNA corresponds to a fragment of 754 nucleotides of the RNA transcribed from the L-strand of the 16S gene of the mitochondrial genome. In still another embodiment, the inverted repeat sequence in the SncmtRNA corresponds to a fragment of 694 nucleotides of the RNA transcribed from the L-strand of the 16S gene of the mitochondrial genome. In another embodiment, the SncmtRNA corresponds to SEQ ID NO:1, SEQ ID NO:2, or SEQ ID NO:3. In another embodiment, the SncmtRNA comprises a sequence selected from the group consisting of SEQ ID NO:200, SEQ ID NO:201, and SEQ ID NO:202.

The antisense chimeric non-coding mitochondrial RNA (ASncmtRNA) molecule corresponds to the 16S mitochondrial ribosomal RNA transcribed from the "L-strand" of the circular mitochondrial genome. Covalently linked to the 5' end of this RNA molecule is a nucleotide sequence or the inverted repeat sequence corresponding to an RNA transcribed from the "H-strand" of the mitochondrial 16S gene. The size of the inverted repeat sequence in the ASncmtRNA can vary from about 25, 50, 75, 100, 125, 150, 175, 200, 225, 250, 275, 300, 325, 350, 375, 400, 425, 450, 475, 500, 525, 550, 575, 600, 625, 650, 675, 700, 725, 750, 775, 800 nucleotides or more to between about 100-200, 150-250, 200-300, 250-350, 400-500, 450-550, 500-600, 550-650, 600-700, 650-750, or 700-800 or more, including any number in between these values. In another embodiment, the ASncmtRNA corresponds to SEQ ID NO:4, SEQ ID NO:5, or SEQ ID NO:6. In another embodiment, the ASncmtRNA comprises a sequence selected from the group consisting of SEQ ID NO:203, SEQ ID NO:204, and SEQ ID NO:205.

Further information related to chimeric mitochondrial RNA molecules can be found in U.S. Pat. No. 8,318,686, the disclosure of which is incorporated by reference herein in its entirety.

In one aspect, the invention provides one or more oligonucleotide complementary to an ASncmtRNA molecule or a SncmtRNA molecule, wherein the oligonucleotide is able to hybridize with the chimeric mitochondrial RNA molecules to form a stable duplex for use in a method disclosed herein. In some aspects, provided herein are methods for suppressing metastasis of a cancer in an individual using one or more oligonucleotides described herein. In some aspects, provided herein are methods for treating or preventing relapse of a cancer in an individual. In some aspects, provided herein are methods for treating metastatic cancer in an individual. In some embodiments herein, the individual has been previously treated for cancer with a therapy (e.g., chemotherapy, radiation therapy, surgery or combinations thereof). In some embodiments, the one or more oligonucleotide complementary to an ASncmtRNA molecule or a SncmtRNA molecule described herein has or more of the following characteristics when used in a method disclosed herein: (1) hybridizes with the chimeric mitochondrial RNA molecules (i.e., an ASncmtRNA molecule or a SncmtRNA molecule) to form a stable duplex; (2) hybridizes with the chimeric mitochondrial RNA molecules expressed by tumor cells and inhibits, arrests, kills or abolishes tumor cells; (3) hybridizes with the chimeric mitochondrial RNA molecules expressed by cancer stem cells (CSCs) and inhibits, arrests, kills or abolishes CSCs; (4) suppresses metastasis of a cancer in an individual (e.g., an individual previously treated for cancer with a therapy); (5) treats or prevents relapse of a cancer in an individual (e.g., an individual previously treated for cancer with a therapy); (6) treats metastatic cancer in an individual (e.g., an individual previously treated for cancer with a therapy); and (7) prolongs overall survival in an individual previously treated for cancer with a therapy (e.g., chemotherapy, radiation therapy, surgery or combinations thereof).

In one aspect, the oligonucleotides for use in any of the methods described herein can be complementary to a SncmtRNA molecule and/or to an ASncmtRNA molecule disclosed herein. Without being bound to theory, it is believed that the complementary oligonucleotides bind to the ncmtRNAs and interfere with their cellular functions. As used herein, an oligonucleotide sequence is "complementary" to a portion of an ncmtRNA, as referred to herein, if the oligonucleotide possesses a sequence having sufficient complementarity to be able to hybridize with the ncmtRNA to form a stable duplex. The ability to hybridize will depend on both the degree of complementarity and the length of the oligonucleotide. Generally, the longer the hybridizing oligonucleotide, the more base mismatches with an ncmtRNA it may contain and still form a stable duplex. In some aspects, the one or more oligonucleotide used according to the methods disclosed herein is at least 8 (such as at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more) base pairs in length. Those skilled in the art can ascertain a tolerable degree of mismatch by use of standard procedures to determine the melting point of the hybridized complex. In some embodiments, the one or more oligonucleotide is at least 85% (such as at least 86%, 87%, 88%, 89%, 90%, 91%, 92%, 93%, 94%, 95%, 96%, 97%, 98%, 99%, or 100%) complementary to a SncmtRNA molecule and/or to a ASnc-mtRNA molecule disclosed herein. In some embodiments, the complementary oligonucleotide is an antisense oligonucleotide. In one embodiment, the one or more oligonucleotide is complementary to one or more ncmtRNA encoded by a nucleic acid sequence selected from the group consisting of SEQ ID NOs: 1-6. In some embodiments, the one or more oligonucleotide comprises a nucleic acid sequence selected from the group consisting of SEQ ID NOs:7-198. In some embodiments, the one or more oligonucleotide comprises a nucleic acid sequence selected from the group consisting of SEQ ID NOs:36, 197 and 198. In some embodiments, the one or more oligonucleotide comprises a nucleic acid sequence selected from the group consisting of SEQ ID NOs:36, 197 and 198.

a. Oligonucleotide Modifications

The naturally occurring internucleoside linkage of RNA and DNA is a 3' to 5 phosphodiester linkage. The oligonucleotides (e.g., an antisense oligonucleotide) used for suppressing metastasis of a cancer, treating or preventing relapse of a cancer, or treating metastatic cancer according to any of the methods disclosed herein can have one or more modified, i.e. non-naturally occurring, internucleoside linkages. With respect to therapeutics, modified internucleoside linkages are often selected over oligonucleotides having naturally occurring internucleoside linkages because of desirable properties such as, for example, enhanced cellular uptake, enhanced affinity for target nucleic acids, and increased stability in the presence of nucleases present in bodily fluids.

Oligonucleotides (e.g., an antisense oligonucleotide) having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known in the art.

In one embodiment, oligonucleotides (e.g., an antisense oligonucleotide) targeted to a SncmtRNA molecule and/or to an ASncmtRNA molecule disclosed herein comprise one or more modified internucleoside linkages. In some embodiments, the modified internucleoside linkages are phosphorothioate linkages.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific, though nonlimiting, examples of oligonucleotides (e.g., an antisense oligonucleotide) useful in the methods of the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

In some embodiments, modified oligonucleotide backbones include, for example, phosphorothioates, chiral phosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thiono-phosphoramidates, thionoalkylphosphonates, thionoalkylphospho-triesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof) can also be employed. Various salts, mixed salts and free acid forms are also included. Oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones: amide backbones; and others having mixed N, O, S and $CH_2$ component parts.

In other embodiments, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 254:1497-1500, 1991.

Representative United States patents that teach the preparation of the above phosphorus-containing and non-phosphorus-containing linkages include, but are not limited to, U.S. Pat. Nos. 5,541,306; 5,550,111; 5,563,253; 5,571,799; 5,587,361; 5,194,599; 5,565,555; 5,527,899; 5,721,218; 5,672,697 and 5,625,050, 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, each of which is herein incorporated by reference.

Modified oligonucleotides (e.g., antisense oligonucleotides) complementary to SncmtRNA and/or ASncmtRNA used as anticancer therapies in combination with any of the methods disclosed herein (e.g., method of suppressing metastasis of a cancer) may also contain one or more substituted sugar moieties. For example, the furanosyl sugar ring can be modified in a number of ways including substitution with a substituent group, bridging to form a bicyclic nucleic acid "BNA" and substitution of the 4'-O with a heteroatom such as S or N(R) as described in U.S. Pat. No. 7,399,845, hereby incorporated by reference herein in its entirety. Other examples of BNAs are described in published International Patent Application No. WO 2007/146511, hereby incorporated by reference herein in its entirety.

The oligonucleotides (e.g., antisense oligonucleotides) for use in the methods disclosed herein (e.g., method of suppressing metastasis of a cancer) can optionally contain one or more nucleotides having modified sugar moieties. Sugar modifications may impart nuclease stability, binding affinity or some other beneficial biological property to the antisense compounds. The furanosyl sugar ring of a nucleoside can be modified in a number of ways including, but not limited to: addition of a substituent group, particularly at the 2' position; bridging of two non-geminal ring atoms to form a bicyclic nucleic acid (BNA); and substitution of an atom or group such as —S—, —N(R)— or —C(R1)(R2) for the ring oxygen at the 4'-position. Modified sugars include, but are not limited to: substituted sugars, especially 2'-substituted sugars having a 2'-F, 2'-OCH2 (2'-OMe) or a 2'-O (CH$_2$)$_2$—OCH$_3$ (2'-O-methoxyethyl or 2'-MOE) substituent group; and bicyclic modified sugars (BNAs), having a 4'-(CH$_2$)n-O-2' bridge, where n=1 or n=2. Methods for the preparations of modified sugars are well known to those skilled in the art.

In certain embodiments, a 2'-modified nucleoside has a bicyclic sugar moiety. In certain such embodiments, the bicyclic sugar moiety is a D sugar in the alpha configuration. In certain such embodiments, the bicyclic sugar moiety is a D sugar in the beta configuration. In certain such embodiments, the bicyclic sugar moiety is an L sugar in the alpha configuration. In certain such embodiments, the bicyclic sugar moiety is an L sugar in the beta configuration.

In other embodiments, the bicyclic sugar moiety comprises a bridge group between the 2' and the 4'-carbon atoms. In certain such embodiments, the bridge group comprises from 1 to linked biradical groups. In certain embodiments, the bicyclic sugar moiety comprises from 1 to 4 linked biradical groups. In certain embodiments, the bicyclic sugar moiety comprises 2 or 3 linked biradical groups. In certain embodiments, the bicyclic sugar moiety comprises 2 linked biradical groups. In certain embodiments, a linked biradical group is selected from —O—, —S—, —N(R1)-, —C(R1)(R2)-, —C(R1)=C(R1)-, —C(R1)=N—, —C(=NR1)-, —Si(R1)(R2)-, —S(=O)2-, —S(=O)—, —C(=O)— and —C(=S)—; where each R1 and R2 is, independently, H, hydroxyl, C1-C12 alkyl, substituted C1-C12 alkyl, C2-C12 alkenyl, substituted C2-C12 alkenyl, C2-C12 alkynyl, substituted C2-C12 alkynyl, C5-C20 aryl, substituted C5-C20 aryl, a heterocycle radical, a substituted hetero-cycle radical, heteroaryl, substituted heteroaryl, C5-C7 alicyclic radical, substituted C5-C7 alicyclic radical halogen, substituted oxy (—O—), amino, substituted amino, azido, carboxyl, substituted carboxyl, acyl, substituted acyl, CN, thiol, substituted thiol, sulfonyl (S(=O)2-H), substituted sulfonyl, sulfoxyl (S(=O)—H) or substituted sulfoxyl; and each substituent group is, independently, halogen, C1-C12 alkyl, substituted C1-C12 alkyl, C2-C12 alkenyl, substituted C2-C12 alkenyl, C2-C12 alkynyl, substituted C2-C12 alkynyl, amino, substituted amino, acyl, substituted acyl, C1-C12 aminoalkyl, C1-C12 aminoalkoxy, substituted C1-C12 aminoalkyl, substituted C1-C12 aminoalkoxy or a protecting group.

Oligonucleotides (e.g., antisense oligonucleotides) for use in any of the methods disclosed herein (e.g., method of suppressing metastasis of a cancer) may also include nucleobase (often referred to in the art simply as "base") modifications or substitutions. Nucleobase modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to oligonucleotide compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an oligonucleotide compound (such as an antisense oligonucleotide compound) for a target nucleic acid (such as an ncmtRNA).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

As used herein, "unmodified" or "natural" nucleobases include the purine bases adenine (A) and guanine (G), and the pyrimidine bases thymine (T), cytosine (C) and uracil (U).

Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), O-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4.5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, pages 858-859. Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289-302. Crooke, S. T. and Lebleu, B. ed., CRC Press, 1993.

Representative United States patents that teach the preparation of certain of the above noted modified nucleobases as well as other modified nucleobases include, but are not limited to, U.S. Pat. Nos. 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, each of which is herein incorporated by reference.

b. Ribozymes

In another embodiment of the invention, ribozymes can be used to interfere with the ncmtRNA molecules described herein to induce cell death in proliferative cells associated with mestastasis (e.g., CSCs). The sequence of the ribozyme can be designed according to the sequence of the ASncmtRNA (for example, a sequence corresponding to SEQ ID NO:4, SEQ ID NO:5, or SEQ ID NO:6, or a sequence comprising SEQ ID NO:203, SEQ ID NO:204, or SEQ ID NO:205) or the SncmtRNA (for example, a sequence corresponding to SEQ ID NO: 1, SEQ ID NO:2, or SEQ ID NO:3, or a sequence comprising SEQ ID NO:200, SEQ ID NO:202, or SEQ ID NO:203) to cleave specific regions of the transcript. Ribozymes are enzymatic RNA molecules capable of catalyzing the specific cleavage of RNA (Rossi, *Curr. Biology* 4:469-471, 1994). The mechanism of ribozyme action involves sequence specific hybridization of the ribozyme molecule to complementary target RNA, followed by an endonucleolytic cleavage. The composition of ribozyme molecules must include one or more sequences complementary to the RNA, and must include the well-known catalytic sequence responsible for RNA cleavage, and described in U.S. Pat. No. 5,093,246, the disclosure of which is incorporated by reference herein in its entirety. As such, within the scope of the invention, hammerhead ribozyme molecules can be engineered that specifically and efficiently catalyze endonucleolytic cleavage of the ASncmtRNA or SncmtRNA molecules disclosed herein. The construction and production of hammerhead ribozymes is well known in the art and it was described (Haseloff et al., *Gene*, 82:43-52, 1989). Ribozymes of the present invention can also include RNA endoribonucleases (Zaug et al., *Science*, 224:574-578, 1984). In some embodiments, a ribozyme described herein can be used in any method described herein. In some embodiments, a method of suppressing metastasis of a cancer in an individual comprises administering to the individual an effective amount of one or more ribozyme described herein. In some embodiments, a method for treating or preventing relapse of cancer in an individual comprises administering to the individual an effective amount of one or more ribozyme described herein. In some embodiments, a method for treating metastatic cancer in an individual comprises administering to the individual an effective amount of one or more ribozyme described herein. In some embodiments, a method for treating a refractory cancer (e.g., a refractory HPV-associated cancer) in an individual comprises administering to the individual an effective amount of one or more ribozyme described herein. In some embodiments, the individual has been previously treated for cancer with a therapy (e.g., chemotherapy, radiation therapy, surgery or combinations thereof).

c. RNA Interference

In another aspect, interference with the function of the ASncmtRNA and/or SncmtRNA molecules disclosed herein for use in any of the methods disclosed herein (e.g., method of suppressing metastasis of a cancer) can be achieved by RNA interference or RNA silencing. RNA interference (RNAi) has emerged as a novel and promising approach for gene silencing in mammalian cells (Elbashir et al., *Nature* 411:494-498, 2001; McManus et al., *Nature Rev. Genet.* 3:737-747, 2002). Synthetically synthesized double stranded RNA molecules of about 8 to 40 (such as about 10 to 36, 14 to 32, 18-28, or 22-24) base pairs (bp) or at least about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bp in length hybridize specifically to their complementary target RNA, leading to degradation of the RNA. Several different genes have been silenced successfully by small interfering RNA or siRNA (Lu et al., *Curr. Opin. Mol. Ther.* 5:225-234, 2003; Wacheck et al., *Oligonucleotides* 13:393-400, 2003). Therefore, synthetic double stranded RNA targeted to the ASncmtRNA and/or SncmtRNA molecules disclosed herein can be used to degrade these transcripts and induce cancer cell death (e.g., CSC death). Those familiar in the art will understand that the sequence of the siRNA has to be complementary to any region of the ASncmtRNA and/or SncmtRNA molecules (such as complementary to any one of a sequence corresponding to SEQ ID NO:1. SEQ ID NO:2, SEQ ID NO:3, SEQ ID NO:4, SEQ ID NO:5, and/or SEQ ID NO:6, or complementary to any one of a sequence comprising SEQ ID NO:200, SEQ ID NO:201, SEQ ID NO:202, SEQ ID NO:203, SEQ ID NO:204, and/or SEQ ID NO:205). In some embodiments, an RNA described herein can be used in any method described herein. In some embodiments, a method of suppressing metastasis of a cancer in an individual comprises administering to the individual an effective amount of one or more RNA described herein. In some embodiments, a method for treating or preventing relapse of cancer in an individual comprises administering to the individual an effective amount of one or more RNA described herein. In some embodiments, a method for treating metastatic cancer in an individual comprises administering to the individual an effective amount of one or more RNA described herein. In some embodiments, a method for treating a refractory cancer (e.g., a refractory HPV-associated cancer) in an individual comprises administering to the individual an effective amount of one or more RNA described herein. In some embodiments, the individual has been previously treated for cancer with a therapy (e.g., chemotherapy, radiation therapy, surgery or combinations thereof).

d. Oligonucleotide Delivery

In one embodiment, a recombinant vector can be used for delivering one or more oligonucleotides (such as any of the oligonucleotides disclosed herein) complementary to a sense and/or antisense chimeric non-coding mitochondrial RNA molecule to the individual. This can include both systemic delivery and delivery localized to a particular region of the body (such as, the bone marrow). Any vector capable of enabling recombinant production of one or more oligonucleotides complementary to a sense or antisense chimeric ncmtRNA molecule and/or which can deliver one or more oligonucleotides complementary to a sense or antisense chimeric ncmtRNA molecule into a host cell is contemplated herein. The vector can be either RNA or DNA, either prokaryotic or eukaryotic, and typically is a virus or a plasmid. The vector can be part of a DNA vaccine or used as part of any other method for delivering a heterologous gene for expression in a host cell that is known to one having skill in the art. Recombinant vectors are capable of replicating when transformed into a suitable host cell. Viral vectors infect a wide range of non-dividing human cells and have been used extensively in live vaccines without adverse side effects. A viral vector (such as, but not limited to, an adenoviral vector or an adeno-associated viral (AAV) vector (e.g. AAV-1. AAV-2, AAV-3, AAV-4, AAV-5, AAV-6, etc. or hybrid AAV vectors comprising the same) is an example of a vector for use in the present methods for delivering one or more oligonucleotides complementary to a sense or antisense chimeric ncmtRNA molecule to cancer cells (such as a plasmocyte; see, e.g. U.S. Patent Application Publication No. 2004/0224389, the disclosure of which is incorporated by reference herein, or a CSC). In some embodiments, a recombinant vector (e.g., a viral vector) described herein can be used in any method described herein. In some embodiments, a method of suppressing metastasis of a cancer in an individual comprises administering to the individual an effective amount of a recombinant vector (e.g., a viral vector) comprising one or more oligonucleotide described herein. In some embodiments, a method for treating or preventing relapse of cancer in an individual comprises administering to the individual an effective amount of a recombinant vector (e.g., a viral vector) comprising one or more oligonucleotide described herein. In some embodiments, a method for treating metastatic cancer in an individual comprises administering to the individual an effective amount of a recombinant vector (e.g., a viral vector) comprising one or more oligonucleotide described herein. In some embodiments, a method for treating a refractory cancer (e.g., a refractory HPV-associated cancer) in an individual comprises administering to the individual an effective amount of a recombinant vector (e.g., a viral vector) comprising one or more oligonucleotide described herein. In some embodiments, the individual has been previously treated for cancer with a therapy (e.g., chemotherapy, radiation therapy, surgery or combinations thereof).

In another aspect, one or more oligonucleotides (such as any of the oligonucleotides disclosed herein) complementary to a sense and/or antisense chimeric non-coding mitochondrial RNA molecule is encapsulated within a microcarrier for deliver to an individual. In certain embodiments, a mixture of different oligonucleotides (such as any of the oligonucleotides disclosed herein) complementary to a sense and/or antisense chimeric non-coding mitochondrial RNA molecule may be encapsulated with a microcarrier, such that the microcarrier encapsulates more than one oligonucleotide species. In some embodiments, the one or more oligonucleotides (such as any of the oligonucleotides disclosed herein) complementary to a sense and/or antisense chimeric non-coding mitochondrial RNA molecule encapsulated within the microcarrier comprises a nucleic acid sequence selected from the group consisting of SEQ ID NOs:7-198. In some embodiments, the one or more oligonucleotides (such as any of the oligonucleotides disclosed herein) complementary to a sense and/or antisense chimeric non-coding mitochondrial RNA molecule encapsulated within the microcarrier comprises a nucleic acid sequence selected from the group consisting of SEQ ID NOs:36, 197 and 198.

Methods of encapsulating oligonucleotides in microcarriers are well known in the art, and described, for example, International application WO98/55495. Colloidal dispersion systems, such as microspheres, beads, macromolecular complexes, nanocapsules and lipid-based system, such as oil-in-water emulsions, micelles, mixed micelles and liposomes can provide effective encapsulation of oligonocelotides within microcarrier compositions. The encapsulation composition may further comprise any of a wide variety of components. These include, but are not limited to, alum, lipids, phospholipids, lipid membrane structures (LMS), polyethylene glycol (PEG) and other polymers, such as polypeptides, glycopeptides, and polysaccharides.

Other Anti-Cancer Therapies

In some aspects, any of the methods of treatment described herein can comprise administering one or more additional anti-cancer therapies to the individual. In some embodiments, the one or more anti-cancer therapy is selected from the group consisting of chemotherapy, radiation therapy, and surgery. Chemotherapy and anti-cancer agents are used interchangeably herein. Various classes of anti-cancer agents can be used. Non-limiting examples include: alkylating agents, antimetabolites, anthracyclines, plant alkaloids, topoisomerase inhibitors, podophyllotoxin, antibodies (e.g., monoclonal or polyclonal), tyrosine kinase inhibitors (e.g., imatinib mesylate (Gleevec® or Glivec®)), hormone treatments, soluble receptors and other antineoplastics.

Topoisomerase inhibitors are also another class of anti-cancer agents that can be used herein. Topoisomerases are essential enzymes that maintain the topology of DNA. Inhibition of type I or type II topoisomerases interferes with both transcription and replication of DNA by upsetting proper DNA supercoiling. Some type I topoisomerase inhibitors include camptothecins: irinotecan and topotecan. Examples of type II inhibitors include amsacrine, etoposide, etoposide phosphate, and teniposide. These are semisynthetic derivatives of epipodophyllotoxins, alkaloids naturally occurring in the root of American Mayapple (*Podophyllum peltatum*).

Antineoplastics include the immunosuppressant dactinomycin, doxorubicin, epirubicin, bleomycin, mechlorethamine, cyclophosphamide, chlorambucil, ifosfamide. The antineoplastic compounds generally work by chemically modifying a cell's DNA.

Alkylating agents can alkylate many nucleophilic functional groups under conditions present in cells. Cisplatin and carboplatin, and oxaliplatin are alkylating agents. They impair cell function by forming covalent bonds with the amino, carboxyl, sulfhydryl, and phosphate groups in biologically important molecules.

Vinca alkaloids bind to specific sites on tubulin, inhibiting the assembly of tubulin into microtubules (M phase of the cell cycle). The vinca alkaloids include: vincristine, vinblastine, vinorelbine, and vindesine.

Anti-metabolites resemble purines (azathioprine, mercaptopurine) or pyrimidine and prevent these substances from becoming incorporated in to DNA during the "S" phase of the cell cycle, stopping normal development and division. Anti-metabolites also affect RNA synthesis.

Plant alkaloids and terpenoids are derived from plants and block cell division by preventing microtubule function. Since microtubules are vital for cell division, without them, cell division cannot occur. The main examples are vinca alkaloids and taxanes.

Podophyllotoxin is a plant-derived compound which has been reported to help with digestion as well as used to produce two other cytostatic drugs, etoposide and teniposide. They prevent the cell from entering the G1 phase (the start of DNA replication) and the replication of DNA (the S phase).

Taxanes as a group includes paclitaxel and docetaxel. Paclitaxel is a natural product, originally known as Taxol and first derived from the bark of the Pacific Yew tree. Docetaxel is a semi-synthetic analogue of paclitaxel. Taxanes enhance stability of microtubules, preventing the separation of chromosomes during anaphase.

In some aspects, the anti-cancer agent can be selected from remicade, docetaxel, celecoxib, melphalan, dexamethasone (Decadron®), steroids, gemcitabine, cisplatinum, temozolomide, etoposide, cyclophosphamide, temodar, carboplatin, procarbazine, gliadel, tamoxifen, topotecan, methotrexate, gefitinib (Iressa®), taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, pacilitaxel, vinblastine, IL-2, GM-CSF, dacarbazine, vinorelbine, zoledronic acid, palmitronate, biaxin, busulphan, prednisone, bortezomib (Velcade®), bisphosphonate, arsenic trioxide, vincristine, doxorubicin (Doxil®), paclitaxel, ganciclovir, adriamycin, estrainustine sodium phosphate (Emcyt®), sulindac, or etoposide.

In other embodiments, the anti-cancer agent can be selected from bortezomib, cyclophosphamide, dexamethasone, doxorubicin, interferon-alpha, lenalidomide, melphalan, pegylated interferon-alpha, prednisone, thalidomide, or vincristine.

In some aspects, the one or more anti-cancer therapy is radiation therapy. As used herein, the term "radiation therapy" refers to the administration of radiation to kill cancerous cells. Radiation interacts with molecules in the cell such as DNA to induce cell death. Radiation can also damage the cellular and nuclear membranes and other organelles. Depending on the radiation type, the mechanism of DNA damage may vary as does the relative biologic effectiveness. For example, heavy particles (i.e. protons, neutrons) damage DNA directly and have a greater relative biologic effectiveness. Electromagnetic radiation results in indirect ionization acting through short-lived, hydroxyl free radicals produced primarily by the ionization of cellular water. Clinical applications of radiation consist of external beam radiation (from an outside source) and brachytherapy (using a source of radiation implanted or inserted into the patient). External beam radiation consists of X-rays and/or gamma rays, while brachytherapy employs radioactive nuclei that decay and emit alpha particles, or beta particles along with a gamma ray. Radiation also contemplated herein includes, for example, the directed delivery of radioisotopes to cancer cells. Other forms of DNA damaging factors are also contemplated herein such as microwaves and UV irradiation.

Radiation may be given in a single dose or in a series of small doses in a dose-fractionated schedule. The amount of radiation contemplated herein ranges from about 1 to about 100 Gy, including, for example, about 5 to about 80, about 10 to about 50 Gy, or about 10 Gy. The total dose may be applied in a fractioned regime. For example, the regime may comprise fractionated individual doses of 2 Gy. Dosage ranges for radioisotopes vary widely, and depends on the half-life of the isotope and the strength and type of radiation emitted. When the radiation comprises use of radioactive isotopes, the isotope may be conjugated to a targeting agent, such as a therapeutic antibody, which carries the radionucleotide to the target tissue (e.g., tumor tissue). Suitable radioactive isotopes include, but are not limited to, $^{211}$astatine, $^{14}$carbon, $^{51}$chromium, $^{36}$chlorine, $^{s7}$iron, $^{58}$cobalt, $^{67}$copper, $^{152}$Eu, $^{67}$gallium, ^hydrogen, $^{123}$iodine, $^{131}$iodine, $^{111}$indium, $^{59}$ion, $^{32}$phosphorus, $^{186}$rhenium, $^{75}$selenium, $^{35}$sulphur, $^{99m}$technicium, and/or $^{o}$yttrium.

Surgery described herein includes resection in which all or part of a cancerous tissue is physically removed, exercised, and/or destroyed. Tumor resection refers to physical removal of at least part of a tumor. In addition to tumor resection, treatment by surgery includes laser surgery, cryosurgery, electrosurgery, and micropically controlled surgery (Mohs surgery). Removal of precancers or normal tissues is also contemplated herein.

Stem Cell Transplantation and Ex Vivo Treatment of Autologous Hematopoietic Stem Cells In other aspects, any of the methods of treatment described herein can include either autologous or allogenic stem cell transplantation therapy. In recent years, high-dose chemotherapy with autologous hematopoietic stem-cell transplantation has become the preferred treatment for certain cancers such as multiple myeloma, non-Hodgkin lymphoma, Hodgkin lymphoma, and leukemia. While not curative, this procedure does prolong overall survival and complete remission. Prior to stem-cell transplantation, patients receive an initial course of induction chemotherapy. The most common induction regimens used today are thalidomide-dexamethasone, bortezomib based regimens, and lenalidomide-dexamethasone (Kyle & Rajkumar, *Blood*, 111 (6): 2962-72, 2008). For example, autologous peripheral stem cell transplantation is useful for up to 50% of multiple myeloma patients. Despite a low mortality rate, problems with such transplant therapy include the inability to eradicate the tumor and the difficulty in the removal of myeloma cells and their precursors from the stem cell collection used for transplantation.

Allogenic transplant (the transplantation of a healthy person's stem cells into the affected individual), is another therapy option for treating certain cancers such as multiple myeloma, non-Hodgkin lymphoma. Hodgkin lymphoma, and leukemia but is less frequently used as it may not provide a cure. For example, most studies evaluating its use in multiple myeloma patients demonstrate long-term disease-free survival of 10-20%, with a significant fraction of patients developing relapse.

When included as a treatment for suppressing or preventing metastasis according to any of the methods disclosed herein, autologous stem cell transplantation can also include the step of treating the hematopoietic stem-cells and/or bone marrow to be transplanted into the affected individual with any of the anti-cancer agents disclosed herein, prior to transplantation into the affected individual. In one embodiment, hematopoietic stem-cells and/or bone marrow for use in autologous stem cell transplantation can be treated with an effective amount of one or more oligonucleotides (e.g., antisense oligonucleotides) sufficiently complementary to an ASncmtRNA or SncmtRNA molecule (e.g., any of the ASncmtRNA and/or SncmtRNA molecules disclosed herein) to form a stable duplex prior to transplantation into the affected individual. In another embodiment, the one or more oligonucleotide is sufficiently complementary to one or more ncmtRNA encoded by a nucleic acid sequence selected from the group consisting of SEQ ID NOs: 1-6, to form a stable duplex. In other embodiments, the one or more oligonucleotide comprises a nucleic acid sequence selected from the group consisting of SEQ ID NOs:7-198. In some embodiments, the one or more oligonucleotide comprises a nucleic acid sequence selected from the group consisting of SEQ ID NOs:36, 197 and 198.

It has been shown that autologous transplantation of bone marrow or hematological stem cells can also be used to treat several forms of hematological cancers (such as, but not limited to, multiple myeloma, leukemia and lymphoma). Accordingly, in some aspects, when included as a treatment for a hematological cancer, provided herein is a method of performing autologous stem cell transplantation which includes the step of treating the hematopoietic stem-cells and/or bone marrow to be transplanted into the affected individual with any of the anti-cancer agent disclosed herein, prior to transplantation into the affected individual. In one embodiment, hematopoietic stem-cells and/or bone marrow for use in autologous stem cell transplantation in an individual with a hematological cancer can be treated with an effective amount of one or more oligonucleotides (e.g., antisense oligonucleotides) sufficiently complementary to an ASncmtRNA molecule or SncmtRNA molecule (e.g., any of the ASncmtRNA and/or SncmtRNA molecules disclosed herein) to form a stable duplex prior to transplantation into the affected individual. In another embodiment, the one or more oligonucleotide is sufficiently complementary to one or more ncmtRNA encoded by a nucleic acid sequence selected from the group consisting of SEQ ID NOs: 1-6, to form a stable duplex. In other embodiments, the one or more oligonucleotide comprises a nucleic acid sequence selected from the group consisting of SEQ ID NOs:7-198. In some embodiments, the one or more oligonucleotide comprises a nucleic acid sequence selected from the group consisting of SEQ ID NOs:36, 197 and 198.

IV. Compositions

Any of the anti-cancer agents (such as oligonucleotide-based agents) disclosed herein can be administered in the form of compositions (e.g., pharmaceutical compositions). These compounds can be administered by systemic administration or local administration through various routes. The route(s) of administration useful in a particular application are apparent to one of skill in the art. Routes of administration include but are not limited to oral, rectal, cerebrospinal, transdermal, subcutaneous, topical, transmucosal, nasopharangeal, pulmonary, intravenous, intramuscular, and intranasal. In some embodiments, the administration is a local administration. In some embodiments, the local administration is selected from the group consisting of administration into an organ, into a cavity, into a tissue, and subcutaneous administration. In some embodiments, the administration is systemic administration. In some embodiments, the systemic administration is intravenous or intraperitoneal administration. These compounds are effective as both injectable and oral compositions. Such compositions are prepared in a manner well known in the pharmaceutical art and comprise at least one active compound. The compositions herein may also contain more than once active compound as necessary for the particular indication being treated, preferably those with complementary activities that do not adversely affect each other. When employed as oral compositions, the oligonucleotides, and other anti-cancer agents disclosed herein, are protected from acid digestion in the stomach by a pharmaceutically acceptable protectant.

This invention also includes pharmaceutical compositions which contain, as the active ingredient, one or more of the anti-cancer agents disclosed herein associated with one or more pharmaceutically acceptable excipients or carriers. In making the compositions of this invention, the active ingredient is usually mixed with an excipient or carrier, diluted by an excipient or carrier or enclosed within such an excipient or carrier which can be in the form of a capsule, sachet, paper or other container. When the excipient or carrier serves as a diluent, it can be a solid, semi-solid, or liquid material which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In some embodiments, in preparing a formulation, it may be necessary to mill the active lyophilized compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 mg to about 100 mg or more, such as any one of about 1 mg to about 5 mg, 1 mg to about 10 mg, about 1 mg to about 20 mg, about 1 mg to about 30 mg, about 1 mg to about 40 mg, about 1 mg to about 50 mg, about 1 mg to about 60 mg, about 1 mg to about 70 mg, about 1 mg to about 80 mg, or about 1 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier.

The anti-cancer agents (such as oligonucleotide-based agents) disclosed herein are effective over a wide dosage range and are generally administered in a therapeutically effective amount. It will be understood, however, that the amount of the anti-cancer agents actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient anticancer therapy is mixed with a pharmaceutical excipient or carrier to form a solid preformulation composition containing a homogeneous mixture of a compound of the present invention. When referring to these preformulation compositions as homogeneous, it is meant that the active ingredient is dispersed evenly throughout the composition so that the composition can be readily subdivided into equally effective unit dosage forms such as tablets, pills and capsules.

The tablets or pills of the present invention can be coated or otherwise compounded to provide a dosage form affording the advantage of prolonged action and to protect the anticancer therapies (such as an oligonucleotide) from acid hydrolysis in the stomach. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compositions of the present invention can be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Parenteral routes of administration include but are not limited to direct injection into a central venous line, intravenous, intramuscular, intraperitoneal, intradermal, or subcutaneous injection. Oligonucleotide (e.g., an oliconucleotide and microcarrier formulation) formulations suitable for parenteral administration are generally formulated in USP water or water for injection and may further comprise pH buffers, salts bulking agents, preservatives, and other pharmaceutically acceptable excipients. Oligonucleotide(s), for example as oligonucleotide microcarrier complexes or encapsulates, for parenteral injection may be formulated in pharmaceutically acceptable sterile isotonic solutions such as saline and phosphate buffered saline for injection.

Compositions for inhalation or insufflation include solutions and suspensions in pharmaceutically acceptable, aqueous or organic solvents, or mixtures thereof, and powders. The liquid or solid compositions can contain suitable pharmaceutically acceptable excipients as described herein. The compositions can be administered by the oral or nasal respiratory route for local or systemic effect. Compositions in pharmaceutically acceptable solvents can be nebulized by use of inert gases. Nebulized solutions can be inhaled directly from the nebulizing device or the nebulizing device can be attached to a face mask tent, or intermittent positive pressure breathing machine. Solution, suspension, or powder compositions can also be administered, orally or nasally, from devices which deliver the formulation in an appropriate manner.

V. Methods of Treatment

A. Methods for Suppressing or Preventing Metastasis of a Cancer

In one aspect, provided herein is one or more oligonucleotide (or composition thereof) for use in suppressing or preventing metastasis of a cancer in an individual. In another aspect, provided herein is one or more oligonucleotide (or compositions thereof) for use in combination with at least one therapy for suppressing or preventing metastasis of a cancer in an individual. In any of the aspects, herein, the individual may have been previously treated for cancer with a therapy.

In some aspects, the invention provides a method for suppressing metastasis of a cancer in an individual comprising administering to the individual an effective amount of one or more oligonucleotide described herein, wherein the oligonucleotide is able to hybridize with the chimeric mitochondrial RNA molecules to form a stable duplex, and wherein the individual has been previously treated for cancer with a therapy. In a further embodiment, the method for suppressing metastasis of a cancer in an individual comprises administering the one or more oligonucleotide in combination with at least one therapy disclosed herein. In some embodiments, the at least one therapy is selected from the group consisting of an anti-cancer agent, a radiation therapy, surgery, an allogenic stem cell transplant therapy, and an autologous stem cell transplant therapy. In some of the embodiments herein, the individual has been previously treated for cancer with a therapy comprising chemotherapy, radiation therapy, surgery, or combinations thereof. In some embodiments, the individual has been previously treated with one or more of bortezomib, cyclophosphamide, dexamethasone, doxorubicin, interferon-alpha, lenalidomide, melphalan, pegylated interferon-alpha, prednisone, thalidomide, and vincristine. In any of the embodiments herein, the oligonucleotide and the at least one therapy is administered sequentially. For example, one or more oligonucleotide described herein can be administered to an individual before or after a tumor(s) has been surgically resected from the individual. In some embodiments, the oligonucleotide and the at least one therapy is administered simulatenously. For example, one or more oligonucleotide described herein can be administered to an individual during surgical resection of a tumor(s) from the individual.

In some aspects, the invention provides a method for preventing metastasis of a cancer in an individual comprising administering to the individual an effective amount of one or more oligonucleotide described herein, wherein the oligonucleotide is able to hybridize with the chimeric mitochondrial RNA molecules to form a stable duplex, and wherein the individual has been previously treated for cancer with a therapy. In a further embodiment, the method for suppressing or preventing metastasis of a cancer in an individual comprises administering the one or more oligonucleotide in combination with at least one therapy disclosed herein. In some embodiments, the at least one therapy is selected from the group consisting of an anti-cancer agent, a radiation therapy, surgery, an allogenic stem cell transplant therapy, and an autologous stem cell transplant therapy. In some of the embodiments herein, the individual has been previously treated for cancer with a therapy comprising chemotherapy, radiation therapy, surgery, or combinations thereof. In some embodiments, the individual has been previously treated with one or more of bortezomib, cyclophosphamide, dexamethasone, doxorubicin, interferon-alpha, lenalidomide, melphalan, pegylated interferon-alpha, prednisone, thalidomide, and vincristine. In any of the embodiments herein, the oligonucleotide and the at least one therapy is administered sequentially. For example, one or more oligonucleotide described herein can be administered to an individual before or after a tumor(s) has been surgically resected from the individual. In some embodiments, the oligonucleotide and the at least one therapy is administered simulatenously. For example, one or more oligonucleotide described herein can be administered to an individual during surgical resection of a tumor(s) from the individual.

As non-limiting examples, a method for suppressing or preventing metastasis of cancer according to the present invention may be by administration of one or more oligonucleotide (or a composition thereof) described herein provided as a daily dosage in an amount of about 0.1 to about 100 mg/kg, such as about 0.5, about 0.9, about 1.0, about 1.1, about 1.5, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 40, about 45, about 50, about 60, about 70, about 80, about 90 or about 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses at every 24, 12, 8, 6, 4, or 2 hours, or any combination thereof.

In some embodiments, the one or more oligonucleotide (or a composition thereof) may be administered in combination with at least one therapy (e.g., an anti-cancer agent, a radiation therapy, surgery, an allogenic stem cell transplant therapy, or an autologous stem cell transplant therapy). In some embodiments, the combination is administered sequentially. For example, a one or more oligonucleotide described herein may be administered about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or alternatively, about 1, 2, 3, 4, 5, 6, 7, 8, 9, 10, 11, 12, 13, 14, 15, 16, 17, 18, 19 or 20 weeks apart from the asministration of the at least one therapy during combination treatment. In some embodiments, the combination is administered simultaneously. For example, a one or more oligonucleotide described herein may be administered about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes, or alternatively, about 1, 2, 3, 4, 5, 6, 7, 8, 9, 10, 11, 12, 13, 14, 15, 16, 17, 18, 19, 20, 21, 22, 23, or 24 hours apart from the administration of the at least one therapy during combination treatment.

B. Methods for Treating or Preventing Relapse of a Cancer

In other aspects, provided herein is one or more oligonucleotide (or compositions thereof) for use in treating or preventing relapse of a cancer in an individual. In some embodiments, the individual has responded to initial treatment and is in remission.

In some aspects, the invention provides a method for treating or preventing relapse of cancer in an individual comprising administering to the individual an effective amount of one or more oligonucleotide described herein, wherein the oligonucleotide is able to hybridize with the chimeric mitochondrial RNA molecules to form a stable duplex, and wherein the individual has been previously treated for cancer with a therapy. In a further embodiment, the method for treating or preventing relapse of cancer in an individual comprises administering the one or more oligonucleotide in combination with at least one therapy disclosed herein. In some embodiments, the at least one therapy is selected from the group consisting of an anti-cancer agent, a radiation therapy, surgery, an allogenic stem cell transplant therapy, and an autologous stem cell transplant therapy. In some of the embodiments herein, the individual has been previously treated for cancer with a therapy comprising chemotherapy, radiation therapy, surgery, or combinations thereof. In some embodiments, the individual has been previously treated with one or more of bortezomib, cyclophosphamide, dexamethasone, doxorubicin, interferon-alpha, lenalidomide, melphalan, pegylated interferon-alpha, prednisone, thalidomide, and vincristine. In any of the embodiments herein, the oligonucleotide and the at least one therapy is administered sequentially. For example, one or more oligonucleotide described herein can be administered to an individual before or after a tumor(s) has been surgically resected from the individual.

In some embodiments, the oligonucleotide and the at least one therapy is administered simulatenously. For example, one or more oligonucleotide described herein can be administered to an individual during surgical resection of a tumor(s) from the individual.

As non-limiting examples, a method for treating or preventing relapse of a cancer according to the present invention may be by administration of one or more oligonucleotide (or a composition thereof) described herein provided as a daily dosage in an amount of about 0.1 to about 100 mg/kg, such as about 0.5, about 0.9, about 1.0, about 1.1, about 1.5, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 40, about 45, about 50, about 60, about 70, about 80, about 90 or about 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses at every 24, 12, 8, 6, 4, or 2 hours, or any combination thereof.

In some embodiments, the one or more oligonucleotide (or a composition thereof) may be administered in combination with at least one therapy (e.g., an anti-cancer agent, a radiation therapy, surgery, an allogenic stem cell transplant therapy, or an autologous stem cell transplant therapy). In some embodiments, the combination is administered sequentially. For example, a one or more oligonucleotide described herein may be administered about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or alternatively, about 1, 2, 3, 4, 5, 6, 7, 8, 9, 10, 11, 12, 13, 14, 15, 16, 17, 18, 19 or 20 weeks apart from the asminstration of the at least one therapy during combination treatment. In some embodiments, the combination is administered simultaneously. For example, a one or more oligonucleotide described herein may be administered about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes, or alternatively, about 1, 2, 3, 4, 5, 6, 7, 8, 9, 10, 11, 12, 13, 14, 15, 16, 17, 18, 19, 20, 21, 22, 23, or 24 hours apart from the administration of the at least one therapy during combination treatment.

In other embodiments, a "maintenance schedule" may be used in which one or more maintenance oligonucleotide-based (such as antisense-based) therapies are administered less frequency than in the original treatment administered prior to remission, such as once per week or once every two weeks. The maintenance schedule can be continued either for a fixed period of time, generally about 1 or about 2 years, or indefinitely as long as the patient is continuing to show no signs of progressive disease and is tolerating the treatment without significant toxicity.

C. Methods for Treating Metastatic Cancer

In yet other aspects, provided herein is one or more oligonucleotide (or compositions thereof) for use in treating metastatic cancer (such as relapsed metastatic cancer) in an individual.

In some aspects, the invention provides a method for the treatment of metastatic cancer (such as relapsed metastatic cancer) in an individual comprising administering to the individual an effective amount of one or more oligonucleotide described herein, wherein the oligonucleotide is able to hybridize with the chimeric mitochondrial RNA molecules to form a stable duplex, and wherein the individual has been previously treated for cancer with a therapy. In a further embodiment, the method for treating metastatic cancer (such as relapsed metastatic cancer) in an individual comprises administering the one or more oligonucleotide in combination with at least one therapy disclosed herein. In some embodiments, the at least one therapy is selected from the group consisting of an anti-cancer agent, a radiation therapy, surgery, an allogenic stem cell transplant therapy, and an autologous stem cell transplant therapy. In some of the embodiments herein, the individual has been previously treated for cancer with a therapy comprising chemotherapy, radiation therapy, surgery, or combinations thereof. In any of the embodiments herein, the oligonucleotide and the at least one therapy is administered sequentially. For example, one or more oligonucleotide described herein can be administered to an individual before or after a tumor(s) has been surgically resected from the individual. In some embodiments, the oligonucleotide and the at least one therapy is administered simultaenously. For example, one or more oligonucleotide described herein can be administered to an individual during surgical resection of a tumor(s) from the individual.

As non-limiting examples, a method for the treatment of metastatic cancer (such as relapsed metastatic cancer) according to the present invention may be by administration of one or more oligonucleotide (or a composition thereof) described herein provided as a daily dosage in an amount of about 0.1 to about 100 mg/kg, such as about 0.5, about 0.9, about 1.0, about 1.1, about 1.5, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 40, about 45, about 50, about 60, about 70, about 80, about 90 or about 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20 after initiation of treatment, or any combination thereof, using single or divided doses at every 24, 12, 8, 6, 4, or 2 hours, or any combination thereof.

In some embodiments, the one or more oligonucleotide (or a composition thereof) may be administered in combination with at least one therapy (e.g., an anti-cancer agent, a radiation therapy, surgery, an allogenic stem cell transplant therapy, or an autologous stem cell transplant therapy). In some embodiments, the combination is administered sequentially. For example, a one or more oligonucleotide described herein may be administered about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 days, or alternatively, about 1, 2, 3, 4, 5, 6, 7, 8, 9, 10, 11, 12, 13, 14, 15, 16, 17, 18, 19 or 20 weeks apart from the administration of the at least one therapy during combination treatment. In some embodiments, the combination is administered simultaneously. For example, a one or more oligonucleotide described herein may be administered about 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, or 59 minutes, or alternatively, about 1, 2, 3, 4, 5, 6, 7, 8, 9, 10, 11, 12, 13, 14, 15, 16, 17, 18, 19, 20, 21, 22, 23, or 24 hours apart from the administration of the at least one therapy during combination treatment.

In another embodiment, the therapeutically effective amount of said one or more oligonucleotide (or compositions thereof) is administered as part of a salvage therapy in treating an individual wherein the cancer has become refractory to other treatment for cancer. In some embodiments, the individual relapsed after treatment with one or more of bortezomib, cyclophosphamide, dexamethasone, doxorubicin, interferon-alpha, lenalidomide, melphalan, pegylated interferon-alpha, prednisone, thalidomide, and vincristine.

Without being bound by theory, it is believed that CSCs give rise to the relapse and/or metastasis of a cancer following treatment of the primary tumor. In some aspects, methods of treatment as described herein (e.g., a method for suppressing or preventing metastasis of a cancer, etc.) eliminates or supresses cancer stem cells. In some embodiments, the oligonucleotides disclosed herein can kill or inhibit cancer stem cells (CSCs) to suppress metastasis, prevent metastasis or prevent relapse of a cancer in an individual. In some embodiments, the individual has been previously treated for cancer with a therapy. In one embodiment, the oligonucleotides disclosed herein can kill or inhibit cancer stem cells (CSCs) that are resistant to treament (e.g., chemotherapy). In one embodiment, treatment of an individual with any one or more oligonucleotide disclosed herein (e.g., an oligonucleotide complementary to an ASncmtRNA molecule) non-selectively inhibits, arrests, kills, or abolishes the CSCs in the individual. In one embodiment, any one or more oligonucleotide disclosed herein (e.g., an oligonucleotide complementary to an ASncmtRNA molecule) reduces the number of CSCs in the individual as compared to an individual not administered the oligonucleotide. In a further embodiment, the individual has been previously treated for cancer with a therapy.

In any embodiments of the methods herein, any one or more oligonucleotide disclosed herein (e.g., an oligonucleotide complementary to an ASncmtRNA molecule) inhibits tumor growth and/or metastasis in the individual as compared to an individual not administered the oligonucleotide.

In any of the embodiments of the methods herein (e.g., a method for suppressing or preventing metastasis of a cancer, a method for treating or preventing relapse of a cancer, a method for treating metaststic cancer, etc.), the cancer may be a solid cancer or a non-solid cancer. In any of the embodiments herein, the cancer is a solid cancer. Examples of solid cancers contemplated herein include, without limitation, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, brain cancer, cervical cancer, ovarian cancer, liver cancer, sarcoma, bladder cancer, hepatoma, breast cancer, colon cancer, colorectal cancer, endometrial or uterine carcinoma, oralpharyngeal cancer, salivary gland carcinoma, renal cancer, liver cancer, prostate cancer, vulval cancer, thyroid cancer, hepatic carcinoma, gastric cancer, melanoma, and various types of head and neck cancer.

In some embodiments, the cancer is associated with a human papilloma virus (HPV) infection, also referred to herein as "HPV-associated cancer", such as in cervical cancer, oralpharyngeal cancer, and head and neck cancer. For example, one of the most important risk factors for development of cervical cancer is an HPV infection. Over 100 strains of HPV have been identified, however, only a subset are classified as high-risk (16, 18, 31, 33, 35, 39, 45, 51, 52, 56, 58, 59, 68, 73, and 82) or probable high-risk (26, 53, and 66) types for the development of cancer (Munoz et al., NEJM, 348:518-527, 2003). Of these HPV types. HPV16 and HPV18 are reported to cause nearly 70% of all cervical cancer cases while HPV 31 and 35 cause another 10% of cervical cancer cases. See Walboomers et al., J Pathol., 189(1):12-9, 1999. HPV-associated cancer can involve one or more of the following steps: (1) initial HPV infection, (2) persistent HPV infection, (3) transforming HPV infection, in the presence or absence of integration of HPV DNA into the host cell genome, (4) development of precancerous lesions, (5) development of at least one primary tumor, and (6) development of invasive cancer (e.g., metastatic cancer).

In some instances, the HPV-associated cancer is resistant to chemotherapeutic agents regularly used for the treatment of cancer. For example, HPV 16-immortalized cervical cells can develop resistance to cisplatin, paclitaxel, actinomycin D, doxrubucin, etoposide, and 5-fluorouracil which presents a major obstacle in cancer treatment. See Ding et al., Int J Cancer, 15:87(6)818-23, 2000. In some embodiments herein, provided herein is one or more oligonucleotide (or compositions thereof) for use in suppressing metastasis of a cancer in an individual wherein the cancer is resistant to a chemotherapeutic agent, and wherein the cancer is an HPV-associated cancer. In some embodiments herein, provided herein is one or more oligonucleotide (or compositions thereof) for use in treating or preventing relapse of a cancer in an individual, wherein the cancer is resistant to a chemotherapeutic agent, and wherein the cancer is an HPV-associated cancer. In some embodiments herein, provided herein is one or more oligonucleotide (or compositions thereof) for use in treating metastatic cancer (such as relapsed metastatic cancer) in an individual, wherein the metastatic cancer is resistant to a chemotherapeutic agent, and wherein the metastatic cancer is an HPV-associated cancer. In some embodiments herein, provided herein is one or more oligonucleotide (or compositions thereof) for use in treating a refractory cancer in an individual. In some embodiments, the refractory cancer is a refractory HPV-associated cancer. In some embodiments, the refractory HPV-associated cancer is resistant to a chemotherapeutic agent. As used herein, the term "refractory cancer" refers to a cancer (e.g., an HPV-associated cancer) that does not respond to treatment, for example, a cancer that is resistant at the beginning of treatment (e.g., treatment with a chemotherapeutic agent) or a cancer that may become resistant during treatment. In some embodiments, the chemotherapeutic agent is selected from the group consisting of cisplatin, paclitaxel, actinomycin D, doxrubucin, etoposide, and 5-fluorouracil. In some embodiments, the chemotherapeutic agent is cisplatin. In some of the embodiments herein, the HPV-associated cancer (e.g., a refractory HPV-associated cancer) is from an infection with one or more HPV strains selected from the group consisting of HPV 16, HPV 18, HPV 31 and HPV 45. In some of the embodiments herein, the HPV-associated cancer (e.g., a refractory HPV-associated cancer) is from an infection with the HPV strain HPV 45. In some embodiments, the one or more oligonucleotide is complementary to the SncmtRNA molecule encoded by a nucleotide sequence selected from the group consisting of SEQ ID NO:1, SEQ ID NO:2, and SEQ ID NO:3. In some embodiments, the one or more oligonucleotide is complementary to the ASncmtRNA molecule encoded by a nucleotide sequence selected from the group consisting of SEQ ID NO:4, SEQ ID NO:5, and SEQ ID NO:6. In some embodiments, the one or more oligonucleotide comprises a nucleotide sequence selected from the group consisting of SEQ ID NOs:7-198. In some embodiments, the one or more oligonucleotide comprises a nucleic acid sequence selected from the group consisting of SEQ ID NOs:36, 197 and 198.

In some embodiments, provided herein is one or more oligonucleotide (or compositions thereof) for use in treating a refractory cancer in an individual. In some embodiments, the refractory cancer is resistant to a chemotherapeutic agent. In some embodiments, the chemotherapeutic agent is cisplatin. In some embodiments, the refractory cancer is a solid cancer disclosed herein. For example, the refractory solid cancer may be one or more of bladder cancer, brain cancer, breast cancer, cervical cancer (e.g., a refractory HPV-associated cervical cancer), colon cancer, endometrial cancer, esophageal cancer, gastric cancer, liver and bile duct cancer, lung cancer, melanoma, oral cancer, ovarian cancer, pancreatic cancer, pharynx cancer, prostate cancer, renal cancer, testicular cancer, or thyroid cancer. In some embodiments, the refractory cancer is a non-solid cancer disclosed herein. For example, the refractory cancer may be one or more of multiple myeloma, leukemia, or lymphoma.

In any of the embodiments herein, the cancer is a non-solid cancer. "Non-solid cancer" refers to a hematological malignancy involving abnormal growth and/or metastasis of a blood cell. Examples of non-solid cancers contemplated herein include, without limitation, multiple myeloma, acute myeloid leukemia, acute lymphoblastic leukemia, chronic myelogenous leukemia, chronic lymphocytic leukemia, acute nonlymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, plasmacytic leukemia, promyelocytic leukemia, Rieder cell leukemia, Schilling's leukemia, stem cell leukemia, subleukemic leukemia, undifferentiated cell leukemia, idiopathic myelofibrosis, lymphoma (such as Non-Hodgkin's lymphoma, and Hodgkin's lymphoma), and myelodysplastic syndrome.

The methods disclosed herein can be practiced in an adjuvant setting. "Adjuvant setting" can refers to a clinical setting in which an individual has had a history of cancer, and generally (but not necessarily) been responsive to therapy, which includes, but is not limited to, surgery (such as surgical resection), radiotherapy, and chemotherapy. However, because of their history of the cancer (such as melanoma or colon cancer), these individuals are considered at risk of development of cancer. Treatment or administration in the "adjuvant setting" refers to a subsequent mode of treatment. The degree of risk (i.e., when an individual in the adjuvant setting is considered as "high risk" or "low risk") depends upon several factors, most usually the extent of disease (cancer) when first treated.

The present invention is accordingly directed to methods for inhibiting the symptoms or conditions (disabilities, impairments) associated with cancer (e.g., metastatic cancer or relapsed cancer) as described in detail below. As such, it is not required that all effects of the condition be entirely prevented or reversed, although the effects of the presently disclosed methods likely extend to a significant therapeutic benefit for the individual. As such, a therapeutic benefit is not necessarily a complete prevention or cure for the condition, but rather, can encompass a result which includes reducing or preventing the symptoms that result from cancer (e.g., metastatic cancer or relapsed cancer), reducing or preventing the occurrence of such symptoms (either quantitatively or qualitatively), reducing the severity of such symptoms or physiological effects thereof, and/or enhancing the recovery of the individual after experiencing cancer (e.g., metastatic cancer or relapsed cancer) symptoms.

Specifically, the therapies (e.g., one or more oligonucleotide) of the present invention, when administered to an individual, can treat or prevent one or more of the symptoms or conditions associated with cancer (e.g., metastatic cancer or relapsed cancer) and/or reduce or alleviate symptoms of or conditions associated with this disorder. As such, protecting an individual from the effects or symptoms resulting from cancer (e.g., metastatic cancer or relapsed cancer) includes both preventing or reducing the occurrence and/or severity of the effects of the disorder and treating a patient in which the effects of the disorder are already occurring or beginning to occur. A beneficial effect can easily be assessed by one of ordinary skill in the art and/or by a trained clinician who is treating the patient. Preferably, there is a positive or beneficial difference in the severity or occurrence of at least one clinical or biological score, value, or measure used to evaluate such individual in those who have been treated with the methods of the present invention as compared to those that have not. For example, the at least one clinical or biological score, value, or measure used to evaluate such an individual is the capability of cells (e.g., cancer stem cells) taken from a primary tumor, a secondary tumor, a biopsy, or ascites fluid of an individual to form spheres in a sphere formation assay. Methods for purifying cells such as cancer stem cells from tumors or other biological samples are well known in the art such as in U.S. Pat. No. 8,614,095, the disclosure of which is incorporated by reference herein in its entirety. In an exemplary sphere formation assay, a tumor is surgically removed from a subject and minced with a scalpel into fragments of approximately 2 to 3 mm3. The fragments are washed with a buffer (e.g., PBS) and then incubated with buffer containing sodium hypochlorite. The tumor tissue fragments are washed with buffer and digested with PBS and digested with a medium containing one or more of collagenase I, collagenase IV, dispase, hyaluronidase and DNAase. The cell suspension is centrifuged and the pellet is suspended in buffer containing βFGF and EGF. The cells are washed to remove serum and suspended in medium supplemented with human EGF, human βFGF, B27 supplement without vitamin A, hydrocortisone, insulin, and N2 supplement. The cells are subsequently cultured in non-adherent plates. After 10 days in culture, spheres of 100 to 200 µm in diameter are obtained and counted. The spheres can be further expanded clonally, or injected into a subject to observe the capability of tumor formation. In some embodiments, an individual that has received an effective amount of one or more oligonucleotide (or compositions thereof) disclosed herein, alone or in combination with at least one therapy disclosed herein, has reduced sphere formation as compared to an individual not treated with the oligonucleotides of the present invention.

VI. Articles of Manufacture or Kits

In another aspect, an article of manufacture or kit is provided which comprises one or more oligonucleotide described herein. The article of manufacture or kit may further comprise instructions for use of the one or more oligonucleotide in the methods of the invention. Accordingly, in certain embodiments, the article of manufacture or kit comprises instructions for use of one or more oligonucleotide complementary to an antisense non-coding chimeric mitochondrial RNA (ASncmtRNA) molecule or a sense non-coding chimeric mitochondrial RNA (SncmtRNA) molecule in methods for suppressing metastasis of a cancer, preventing or treating relapse of a cancer, and/or treating metastatic cancer in an individual comprising administering to the individual an effective amount of the one or more oligonucleotide. In certain embodiments, the individual has been previously treated for cancer with a therapy (e.g., chemotherapy, radiation therapy, surgery, or combinations thereof). In some embodiments, the article of manufacture or kit comprises instructions for use of one or more oligonucleotide complementary to an antisense non-coding chimeric mitochondrial RNA (ASncmtRNA) molecule or a sense non-coding chimeric mitochondrial RNA (SncmtRNA) molecule in methods for treating a refractory cancer (e.g., a refractory HPV-associated cancer) in an individual comprising administering to the individual an effective amount of the one or more oligonucleotide.

The article of manufacture or kit may further comprise a container. Suitable containers include, for example, bottles, vials (e.g., dual chamber vials), syringes (e.g., single or dual chamber syringes), IV bags, and test tubes. The container may be formed from a variety of materials such as glass or plastic. The container holds the composition (e.g., pharmaceutical formulation).

The article of manufacture or kit may further comprise a label or package insert, which is on, or associated with the container and may indicate directions for reconstitution and/or use of the composition (e.g., pharmaceutical formulation). The label may further indicate that the formulation is useful or intended for intravenous, subcutaneous, or other modes of administration for suppressing metastasis of a cancer, preventing or treating relapse of a cancer, and/or treating metastatic cancer in an individual. In other embodiments, the label may further indicate that the formulation is useful or intended for intravenous, subcutaneous, or other modes of administration for treating a refractory cancer (e.g., a refractory HPV-associated cancer) in an individual. The container holding the formulation may be a single-use vial or a multi-use vial which allows for repeat administrations (e.g., from 2-6 administrations) of the reconstituted composition (e.g., pharmaceutical formulation). The article of manufacture or kit may further comprise a second container comprising a suitable diluent. The article of manufacture or kit may further include other materials desirable from a commercial, therapeutic, and user standpoint, including other buffers, diluents, filters, needles, syringes, and package inserts with instructions for use.

The article of manufacture of kit described herein optionally further comprises a container comprising a second therapeutic composition (e.g., an anti-cancer agent). For example, the article of manufacture or kit can comprise one or more oligonucleotide as a first composition (e.g., a first pharmaceutical composition) and an anti-cancer agent as a second composition (e.g., a second pharmaceutical composition). In some embodiments, the kit further comprises instructions for use of the one or more oligonucleotide in combination with the anti-cancer agent in the methods of the invention. An exemplary anti-cancer agents may be remicade, docetaxel, celecoxib, melphalan, dexamethasone, steroids, gemcitabine, cisplatinum, temozolomide, etoposide, cyclophosphamide, temodar, carboplatin, procarbazine, gliadel, tamoxifen, topotecan, methotrexate, gefitinib, taxol, taxotere, fluorouracil, leucovorin, irinotecan, xeloda, CPT-11, interferon alpha, pegylated interferon alpha, capecitabine, cisplatin, thiotepa, fludarabine, carboplatin, liposomal daunorubicin, cytarabine, doxetaxol, pacilitaxel, vinblastine. IL-2, GM-CSF, dacarbazine, vinorelbine, zoledronic acid, palmitronate, biaxin, busulphan, prednisone, bortezomib, bisphosphonate, arsenic trioxide, vincristine, doxorubicin, paclitaxel, ganciclovir, adriamycin, estrainustine sodium phosphate, sulindac, and/or etoposide.

VII. Additional Exemplary Embodiments

The present application in some embodiments provides a method of treatment for a refractory cancer in an individual comprising administering to the individual an effective amount of one or more oligonucleotide complementary to an antisense non-coding chimeric mitochondrial RNA (ASncmtRNA) molecule or a sense non-coding chimeric mitochondrial RNA (SncmtRNA) molecule, wherein the oligonucleotide is able to hybridize with the chimeric mitochondrial RNA molecules to form a stable duplex.

In some embodiments according to (or as applied to) any of the embodiments above, the oligonucleotide is sufficiently complementary to a human non-coding chimeric mitochondrial RNA molecule comprising: a) an antisense 16S mitochondrial ribosomal RNA covalently linked at its 5' end to the 3' end of a polynucleotide with an inverted repeat sequence or b) a sense 16S mitochondrial ribosomal RNA covalently linked at its 5' end to the 3' end of a polynucleotide with an inverted repeat sequence.

In some embodiments according to (or as applied to) any of the embodiments above, the oligonucleotide is complementary to the ASncmtRNA molecule encoded by a nucleotide sequence selected from the group consisting of SEQ ID NO:4, SEQ ID NO:5, and SEQ ID NO:6.

In some embodiments according to (or as applied to) any of the embodiments above, the oligonucleotide is at least 85% complementary to the ASncmtRNA molecule encoded by a nucleotide sequence selected from the group consisting of SEQ ID NO:4, SEQ ID NO:5, and SEQ ID NO:6.

In some embodiments according to (or as applied to) any of the embodiments above, the one or more oligonucleotide comprises a nucleotide sequence selected from the group consisting of SEQ ID NOs:7-198.

In some embodiments according to (or as applied to) any of the embodiments above, the one or more oligonucleotide comprises a nucleic acid sequence selected from the group consisting of SEQ ID NOs:36, 197 and 198.

In some embodiments according to (or as applied to) any of the embodiments above, the oligonucleotide is administered in combination with at least one anti-cancer agent.

In some embodiments according to (or as applied to) any of the embodiments above, the oligonucleotide and the at least one anti-cancer agent is administered sequentially.

In some embodiments according to (or as applied to) any of the embodiments above, the oligonucleotide and the at least one anti-cancer agent is administered simultaneously.

In some embodiments according to (or as applied to) any of the embodiments above, the oligonucleotide is administered in combination with a radiation therapy.

In some embodiments according to (or as applied to) any of the embodiments above, the oligonucleotide is administered in combination with surgery.

In some embodiments according to (or as applied to) any of the embodiments above, the individual has been previously treated for cancer with a therapy comprising chemotherapy, radiation therapy, surgery, or combinations thereof.

In some embodiments according to (or as applied to) any of the embodiments above, the refractory cancer is a refractory HPV-associated cancer.

In some embodiments according to (or as applied to) any of the embodiments above, the refractory HPV-associated cancer is one or more selected from the group consisting of: cervical cancer, oralpharyngeal cancer, and head and neck cancer.

In some embodiments according to (or as applied to) any of the embodiments above, the refractory HPV-associated cancer is resistant to a chemotherapeutic agent.

In some embodiments according to (or as applied to) any of the embodiments above, the chemotherapeutic agent is one or more selected from the group consisting of: cisplatin, paclitaxel, actinomycin D, doxrubucin, etoposide, and 5-fluorouracil.

In some embodiments according to (or as applied to) any of the embodiments above, the refractory HPV-associated cancer is from an infection with one or more HPV strains selected from the group consisting of: HPV 16, HPV 18, HPV 31 and HPV 45.

In some embodiments according to (or as applied to) any of the embodiments above, the oligonucleotide reduces the number of cancer stem cells in the individual as compared to an individual not administered the oligonucleotide.

In some embodiments according to (or as applied to) any of the embodiments above, the oligonucleotide inhibits tumor growth and/or metastasis in the individual as compared to an individual not administered the oligonucleotide.

The invention will be more fully understood by reference to the following examples. The examples, which are intended to be purely exemplary of the invention, should not be construed as limiting the scope of the invention in any way. It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1: Treatment of HCT-116 Colon Cancer Cells and Primary Cultures of Human Colon Cancer Cells with Antisense Oligonucleotides Complementary to Antisense Non-Coding Chimeric Mitochondrial RNA Abolished Sphere Formation In this study, the ability of cells, from both the HCT-116 colon cancer cell line and primary cultures of human colon cancer cells derived from patients, to form spheroid bodies following treatment with antisense oligonucleotides directed to antisense non-coding chimeric mitochondrial RNA (ASncmtRNA) was determined. The assay utilized measured the numbers of spheroid bodies, also referred to herein as spheres, based on the specific ability of cancer stem cells to form these spheroid bodies.

Materials and Methods
Experimental Scheme:

FIG. 1 demonstrates a general scheme of the experimental procedure and the assay utilized herein to measure the effect of antisense oligonucleotides targeted to ASncmtRNA on the number of spheres formed in colon cancer cells, based on the specific ability of cancer stem cells to form these spheroid bodies. Sphere formation was measured in HCT-116 colon cancer cells and primary cultures of human colon cancer cells derived from patients.

Primary Cultures of Human Cancer Cells:

Biopsies of colon cancer were received post-surgery and with corresponding informed consent of each patient. Pieces of tumors of about 500 mm3 were transferred to sterile tubes of 50 ml containing DMEM medium. High-Glucose, GlataMax™ (GIBCO), 10% FCS (Biological Industries), Fungizone® 1×, 2× antibiotic-antimycotic mix and gentamicin 25 µg/ml (Invitrogen). The biopsies were processed within 2 to 3 h post-surgery.

In order to disaggregate the tumor, a piece of colon tumor was minced with a scalpel into fragments of approximately 2 to 3 mm3. The fragments were washed twice with PBS and then incubated for 20 minutes with PBS containing 0.5% sodium hypochlorite. The fragments were washed three times with PBS and digested with RPMI medium (Invitrogen) containing 1 mg/ml collagenase I, 2 mg/ml collagenase IV, 1 mg/ml dispase, 20 µg/ml hyaluronidase and 2000 U/ml DNAase. The mix was incubated at 37° C. for 60 min and with constant stirring. Next, the cell suspension was centrifuged at 200×g for 5 minutes and the pellet was suspended in PBS and centrifuged again a 200×g for 5 minutes. The pellet was resuspended in DMEM/F12 containing 1×N2 supplement, 10 ng/ml βFGF and 20 ng/ml EGF, for the formation of spheres.

Culture of HCT-116 Cells:

HCT-116 cells were cultured according to standard protocols. HCT-116 cells obtained from ATCC were grown in DMEM medium containing penicillin, gentamicin and fungizone, with 10% FCS, at 37° C. and with 5% CO2.

Selection of Tumor Cells by Sphere Formation and Adherence to Coated Plates:

Cells derived from colon cancer tumors or HCT-116 cultures were collected and washed to remove serum and suspended in serum-free DMEM/F12 supplemented with 100 IU/ml penicillin, 100 µg/ml streptomycin, 20 ng/ml human EGF, 20 ng/ml human βFGF, 2% B27 supplement without vitamin A, hydrocortisone, insulin (Lonza) and N2 supplement (Invitrogen, Carlsbad, Calif., USA). The cells were subsequently cultured in non-adherent plates (Corning Inc., Corning, N.Y., USA) at a density of about 5.000 cells/well or 1×105 cells in T25 flasks (Corning Inc. T25 3815). After 10 days in culture, spheres of 100 to 200 µm in diameter were obtained. The medium containing the spheres were filtered using a 70 µm nylon filter to eliminate single cells. The spheres were collected and dissociated with trypsin-EDTA and mechanically disrupted with a pipette. The cells were then centrifuged to remove the enzyme, washed once with DMEM medium containing 105 CFS and plated in adherent plates coated with collagen I (Gibco) and cultured at 37° C. and 5% CO2 as described before.

Cell Transfection and Antisense Oligonucleotides:

Antisense oligonucleotides (ASOs) used in this study were synthesized by IDT (Integrated DNA Technologies, USA), Invitrogen or Biosearch Inc. with 100% phosphorothioate (PS) internucleosidic linkages. For transfection, cells were seeded into 12-well plates (Nunc) at 50,000 cells/well. The next day, cells selected from colon cancer tumors or from HCT-116 cultures (see Selection of tumor cells by sphere formation and adherence to coated plates) were transfected with the antisense oligonucleotides (ASO 1107S: 5'-GTCCTAAACTACCAAACC-3' (SEQ ID NO:197) or ASO 1537S: 5'-CACCCACCCAAGAACAGG-3' (SEQ ID NO:36), depending on the cell type) or a control oligonucleotide (Control Oligo 154: 5'-AGGTGGAGTGGATTGGGG-3' (SEQ ID NO: 199)) at a final concentration of 100 to 200 nM (depending on the cell type) using Lipofectamine 2000 (Invitrogen) according to the manufacturer's directions. In addition, a subset of cells were left untreated or in the presence of only Lipofectamine 2000. Transfection was for 48 hours under normal culture conditions.

Sphere Formation Assay:

At 48 hours post transfection, the cells were harvested, counted and 5,000 to 6,000 cells were cultured in non-adherent 6-well plates (Corning Inc., Corning, N.Y., USA) as described before (described supra). After 10 days in culture, spheres of 100 to 200 µm in diameter were obtained and counted.

Results

Figure 2:
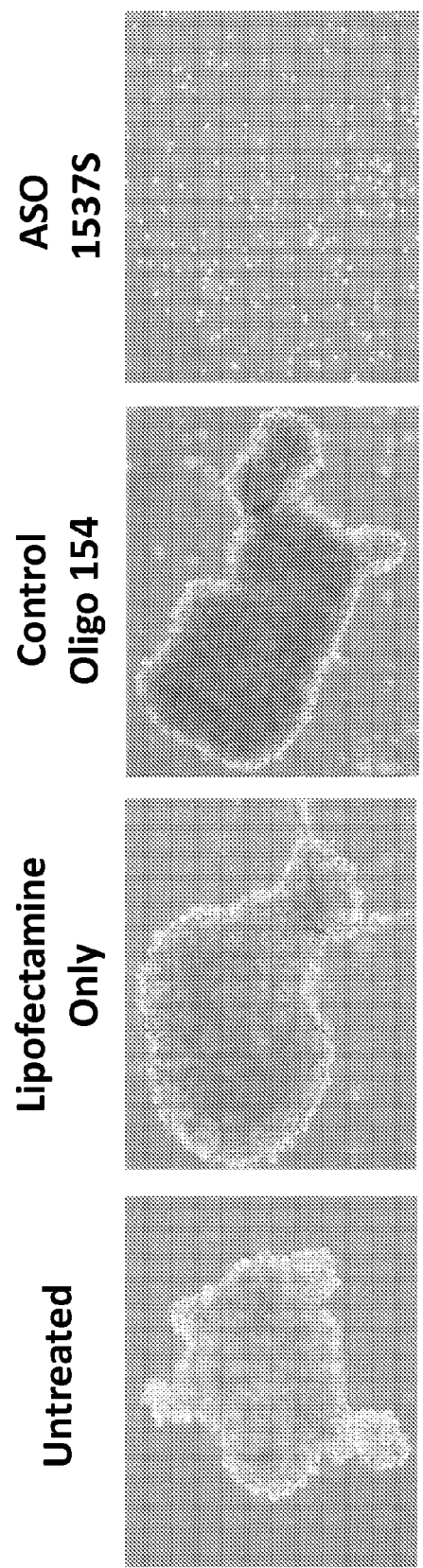
FIG. 2 depicts representative examples of spheres formed in primary colon tumor cancer cells following no treatment, treatment with only Lipofectamine, treatment with a control oligonucleotide (Control Oligo 154), or treatment with an antisense oligonucleotide (ASO) targeted to ASncmtRNA (ASO 1537S). Treatment with the ASO 1537S abolished the formation of spheres.

Sphere formation was unchanged in primary cultures of colon tumor cells following no treatment, treatment with only Lipofectamine, or treatment with Control Oligo 154. But sphere formation was abolished in these primary cells following treatment with ASO 1537S (FIG. 2).

Figure 3:
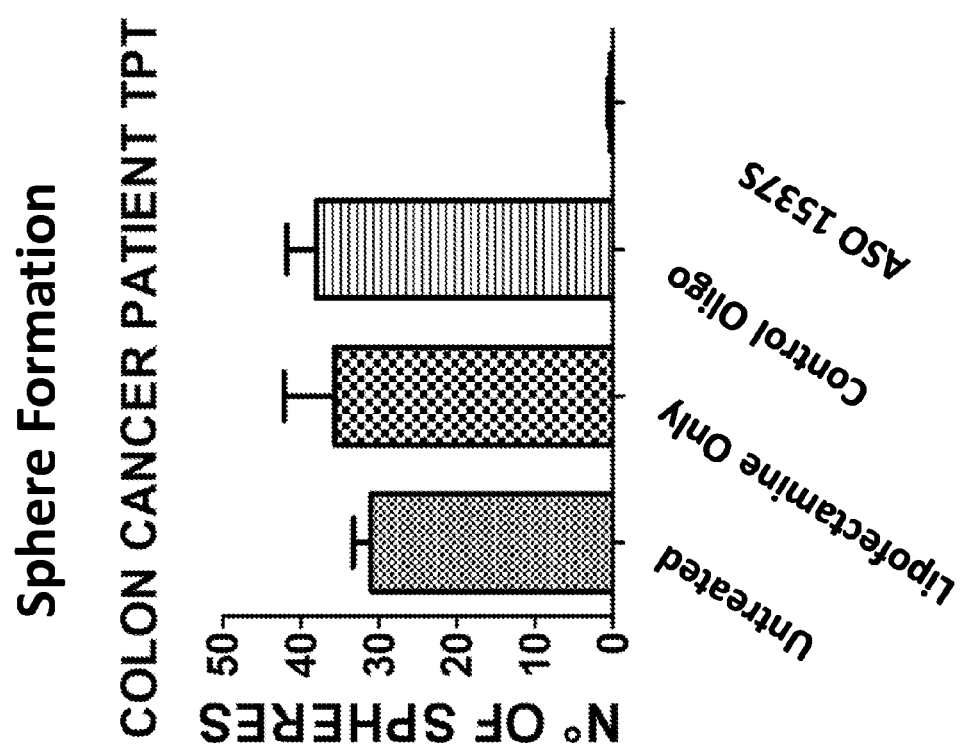
FIG. 3 depicts a quantification of the capacity of primary colon tumor cells to form spheres. Approximately 0.6% of the total number of cells seeded were able to form spheres. Cells transfected with ASO 1537S were unable to form spheres.

A primary culture of a colon tumor (patient TPT; 50,000 cells) was used to quantify sphere formation and evaluate the effect of transfection with ASO 1537S on the capacity of these cells to form spheres. The three groups of control cells (untreated, treated with Lipofectamine only, or treated with Control Oligo 154) formed spheres (30 to 37 spheres) equivalent to approximately 0.6% of the total number of cells seeded. Cells transfected with ASO 1537S were unable to form spheres (FIG. 3).

Figure 4:
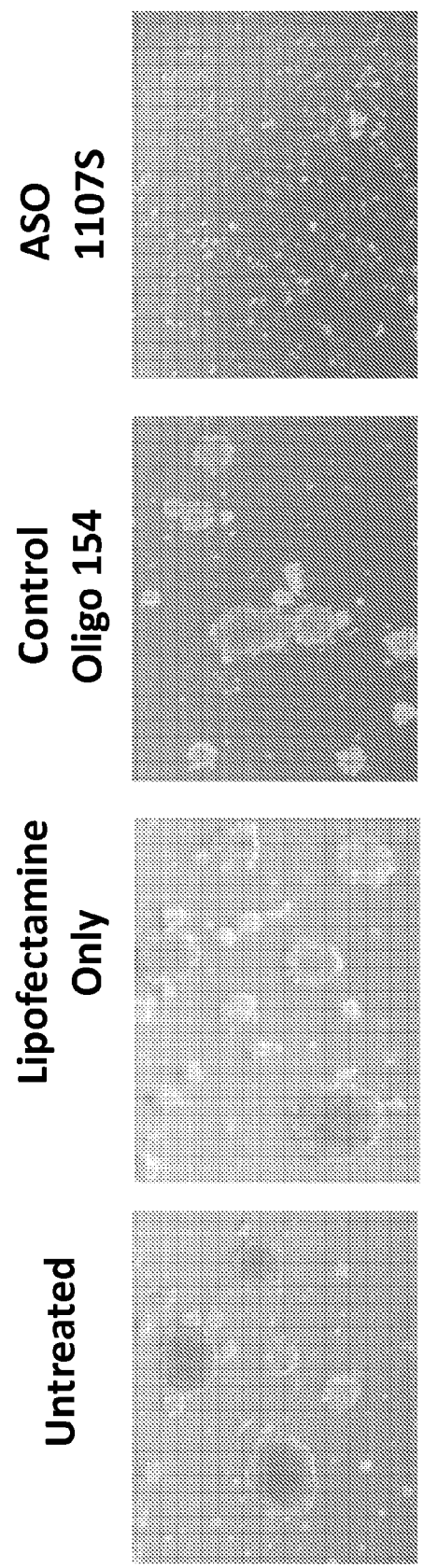
FIG. 4 depicts representative examples of spheres formed in cells from the HCT-116 colon cancer cell line following no treatment, treatment with only Lipofectamine, treatment with a control oligonucleotide (Control Oligo 154), or treatment with an antisense oligonucleotide targeted to ASncmtRNA (ASO 1107S). Treatment with ASO 1107S abolished the formation of spheres.

Sphere formation was unchanged in cells from the HCT-116 colon tumor cell line following no treatment, treatment with only Lipofectamine, or treatment with Control Oligo 154. However, sphere formation was abolished in these cells following treatment with ASO 1107S (FIG. 4).

Figure 5:
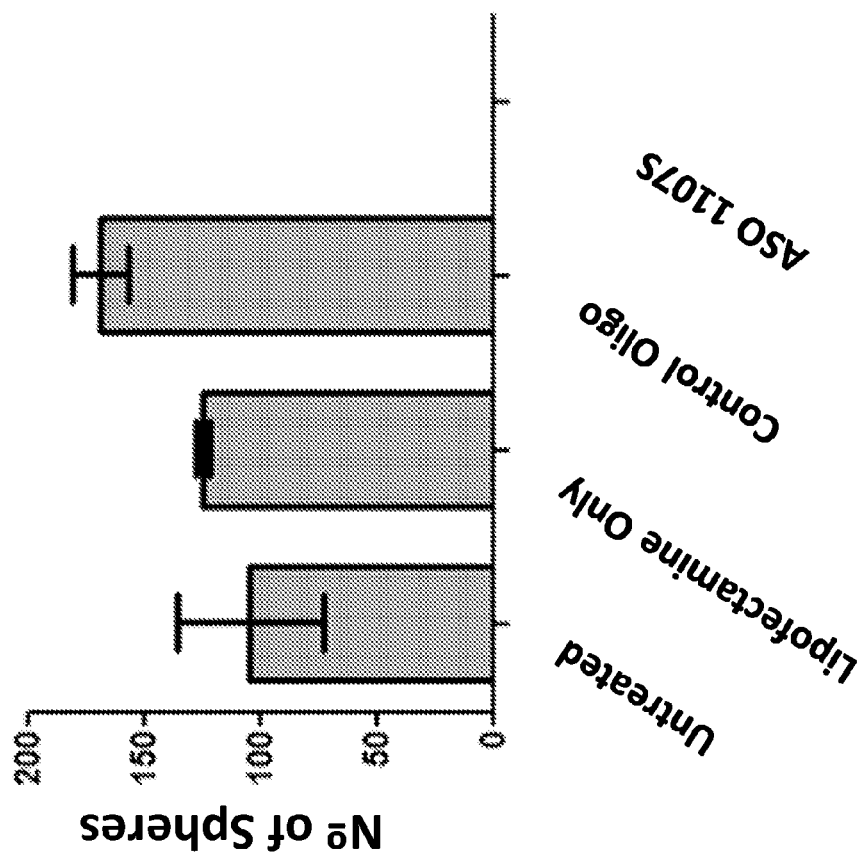
FIG. 5 depicts a quantification of the capacity of HCT-116 colon cancer cells to form spheres. Approximately 0.3% of the total number of cells seeded were able to form spheres. Cells transfected with ASO 1107S were unable to form spheres.

The colon tumor cell line HCT-116 was used to quantify sphere formation and evaluate the effect of transfection with ASO 1107S on sphere formation. The three groups of control cells (untreated, treated with Lipofectamine only, or treated with Control Oligo 154) formed spheres (100 to 160 spheres), equivalent to 0.3% of the total amount of cells seeded (in this representative example 50,000 cells in T25 flasks). However, cells transfected with ASO 1107S were not able to form spheres (FIG. 5).

Taken together, these results show that groups left untreated, treated with only Lipofectamine, or transfected with a control oligonucleotide retained the ability to form spheres. In contrast, primary colon tumor cells or HCT-116 colon cancer cells transfected with antisense oligonucleotides lost their ability to form spheres. These results indicate that the antisense oligonucleotides were able to kill cancer stem cells as indicated by the lack of sephere formation upon treatment. Furthermore, these results also indicate that only a fraction of all cells seeded were able to form spheres.

Example 2: Treatment of a Cervical Cancer Cell Line and Primary Cultures of Human Uterine Cervical Cancer Cells with Antisense Oligonucleotides Complementary to Antisense Non-Coding Chimeric Mitochondrial RNA Abolished Sphere Formation The ability of cervical cells from the SiHa cervical cancer cell line (transformed with Human Papillomavirus 16 or HPV 16) and from primary cultures of human uterine cervical cancer cells derived from patients to form spheroid bodies following treatment with antisense oligonucleotides directed to antisense non-coding chimeric mitochondrial RNA (ASncmtRNA) was determined. The assay utilized measured the numbers of spheroid bodies, also referred to herein as spheres, which are formed by cancer stem cells.

Figure 6:
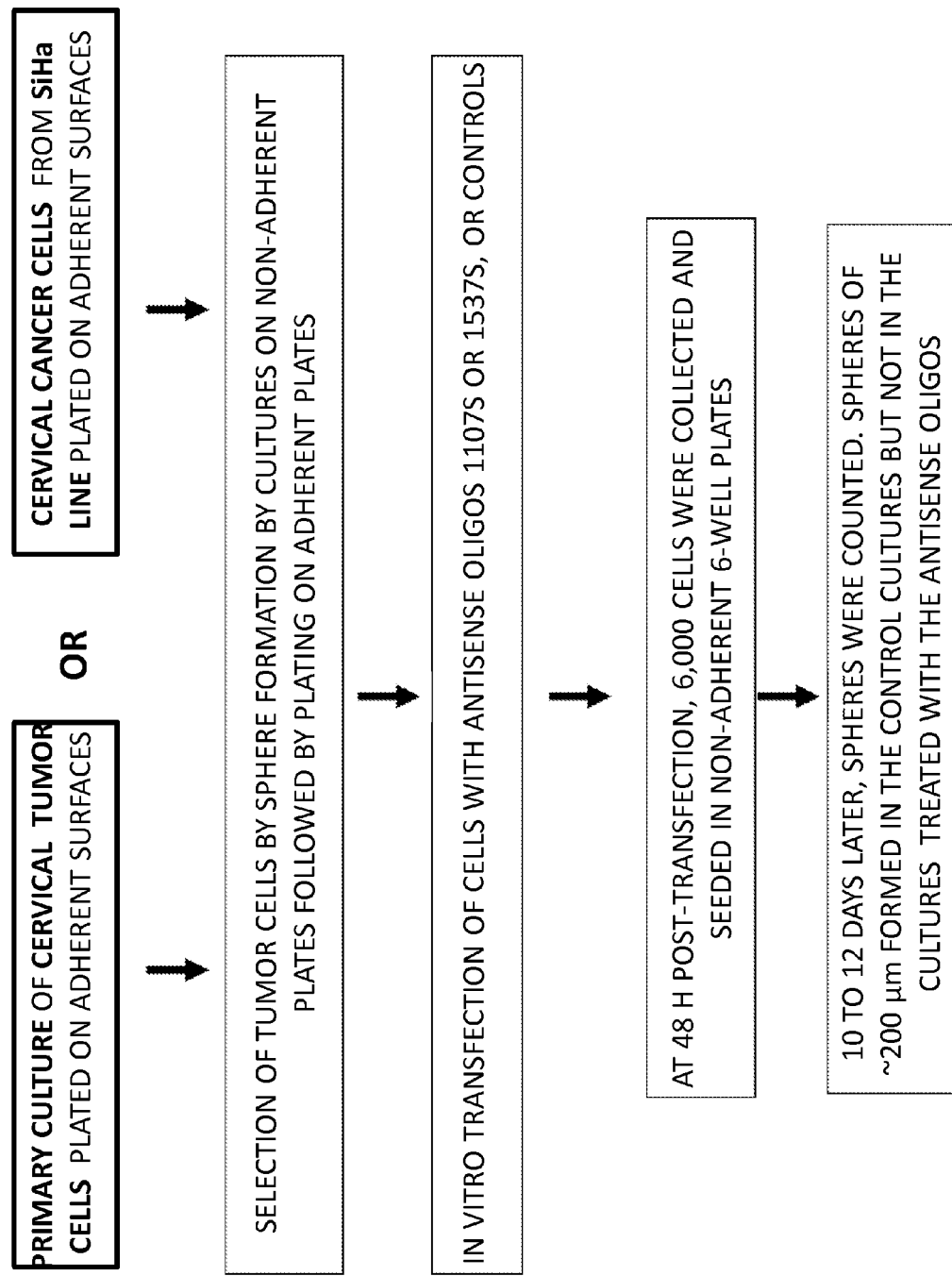
FIG. 6 depicts a general scheme of the experimental procedure and the assay utilized herein to measure the effect of antisense oligonucleotides targeted to ASncmtRNA on the number of spheres formed by the cervical cancer SiHa cell line and primary culture cells of cervical tumors. The assay is based on the ability of cancer stem cells to form spheres, also referred to herein as spheroid bodies.

Materials and Methods
Experimental Scheme:

The experimental procedure and assay utilized herein measured the effect of antisense oligonucleotides that were targeted to ASncmtRNA on the number of spheres formed by cervical cancer cells (FIG. 6). Sphere formation was measured in the SiHa cervical cancer cell line and primary cultures of human cervical cancer cells derived from patients (CerCa). CerCa 1, CerCa 2 and CerCa 3 (transformed with Human Papillomavirus 45) were obtained from patient biopsies.

Culture of SiHa Cells:

SiHa cells were grown in DMEM, "High Glucose", GlutaMAX™, containing penicillin, gentamicin and fungizone, with 10% FCS at 37° C. and with 5% C02.

Primary Cultures of Human Cancer Cells;

Biopsies of uterine cervical cancer were received post-surgery and with the corresponding informed consent of each patient. Pieces of tumors of about 500 mm3 were transferred to 50 mL sterile tubes containing DMEM medium, High-Glucose, GlataMax™ (GIBCO), 10% FCS (Biological Industries), Fungizone® 1×, 2× antibiotic-antimycotic mix and gentamicin 25 µg/ml (Invitrogen). The biopsies were processed within 2 to 3 hours post-surgery.

In order to disaggregate the tumor, the tissue sample was placed on a 10 cm Petri dish with 10 ml of sterile PBS (Gibco) and sliced with a scalpel into small pieces (1-3 mm3). The pieces were transfered to 6 cm dishes together with 2 ml of medium containing 0.5% Colagenase 1, 0.5% Colagenase II, 0.5% Colagenase IV (GIBCO), 0.5% hialorunidase (AppliChem), 0.1% Dispase (GIBCO), 0.05% DNase (AppliChem), 0.1% BSA (Rockland), antibiotic-antimycotic 2× mix (GIBCO) and Fungizone® 2× (GIBCO). The fragments were incubated at 37° C. for 30 min and the cell suspension was centrifuged at 300×g for 5 minutes. The pellet was suspended in 5 ml MEGM™ medium containing 20 ng/ml of hEGF 20, hydrocortisone, insulin, GA-1000 (Lonza), 0.5×B-27 without vitamin A (Invitrogen), 20 ng/ml of FGFb (Invitrogen) and 5% CFB. The cells were cultured in a T25 flask coated with collagen (BD Bioscience) at 37° C. and with 5% CO2. The medium was changed every 48 hours.

Selection of Tumor Cells by Sphere Formation and Adherence to Coated Plates:

About 1×105 cells resuspended in MEGM™ medium supplemented with 20 ng/ml of hEGF, hydrocortisone, insulin, GA-1000 (Lonza), 0.5×B-27 without vitamin A (Invitrogen), 20 ng/ml of FGFb (Invitrogen) without CFS were seeded on ultra-low adherence plates (Corning). Ten days later, the spheres were counted under phase microscopy, collected and filtered using a nylon mesh of 70 µm to discard single cells. The spheres were recovered from the filter and seeded on 6-well plates (Corning) previously coated with collagen type I (Gibco) and cultured as described above. Three human primary cultures of cervical tumors, CerCa 1, CerCa 2 and CerCa 3, were isolated.

Human Papillomavirus (HPV) Genotyping:

The different primary cultures were analyzed with the PGMY09/11 Linear Array (Roche). The presence of HPV 16 was detected in CerCa 1 and CerCa 2 primary cell cultures while HPV 45 was detected in the CerCa 3 primary cell culture.

Cell Transfection and Antisense Oligonucleotides:

Antisense oligonucleotides (ASOs) used in this study were synthesized by IDT (Integrated DNA Technologies, USA), Invitrogen or Biosearch Inc. with 100% phosphorothioate (PS) internucleosidic linkages. For transfection, cells were seeded into 12-well plates (Nunc) at 5000 cells/well. The next day, cells selected from cervical cancer tumors or from SiHa cells (See Selection of Tumor Cells by Sphere Formation and Adherence to Coated Plates) were transfected with an antisense oligonucleotide (ASO 1537S: 5'-CAC-CCACCCAAGAACAGG-3' (SEQ ID NO:36), depending of the cell type) or a control oligonucleotide 154 (ASO-C: 5'-AGGTGGAGTGGATTGGGG-3'(SEQ ID NO: 199)) at a final concentration of 100 nM (SiHa cells) or 200 nM (CerCa cells) using Lipofectamine 2000 (Invitrogen) according to the manufacturer's directions. In addition, a subset of cells were left untreated (NT), transfected in the presence of Lipofectamine 2000 (LIPO) only, or incubated with 45 uM cisplatin (CISP). Transfection was conducted for 72 hours under normal culture conditions.

Sphere Formation Assay:

At 72 hours post transfection, the cells were harvested, counted and 5,000 to 6,000 cells were cultured in non-adherent 6-well plates (Corning Inc., Corning, N.Y., USA) as described above. After 10 days in culture, spheres of 100 to 200 µm in diameter were obtained and counted.

Results

Figure 7:
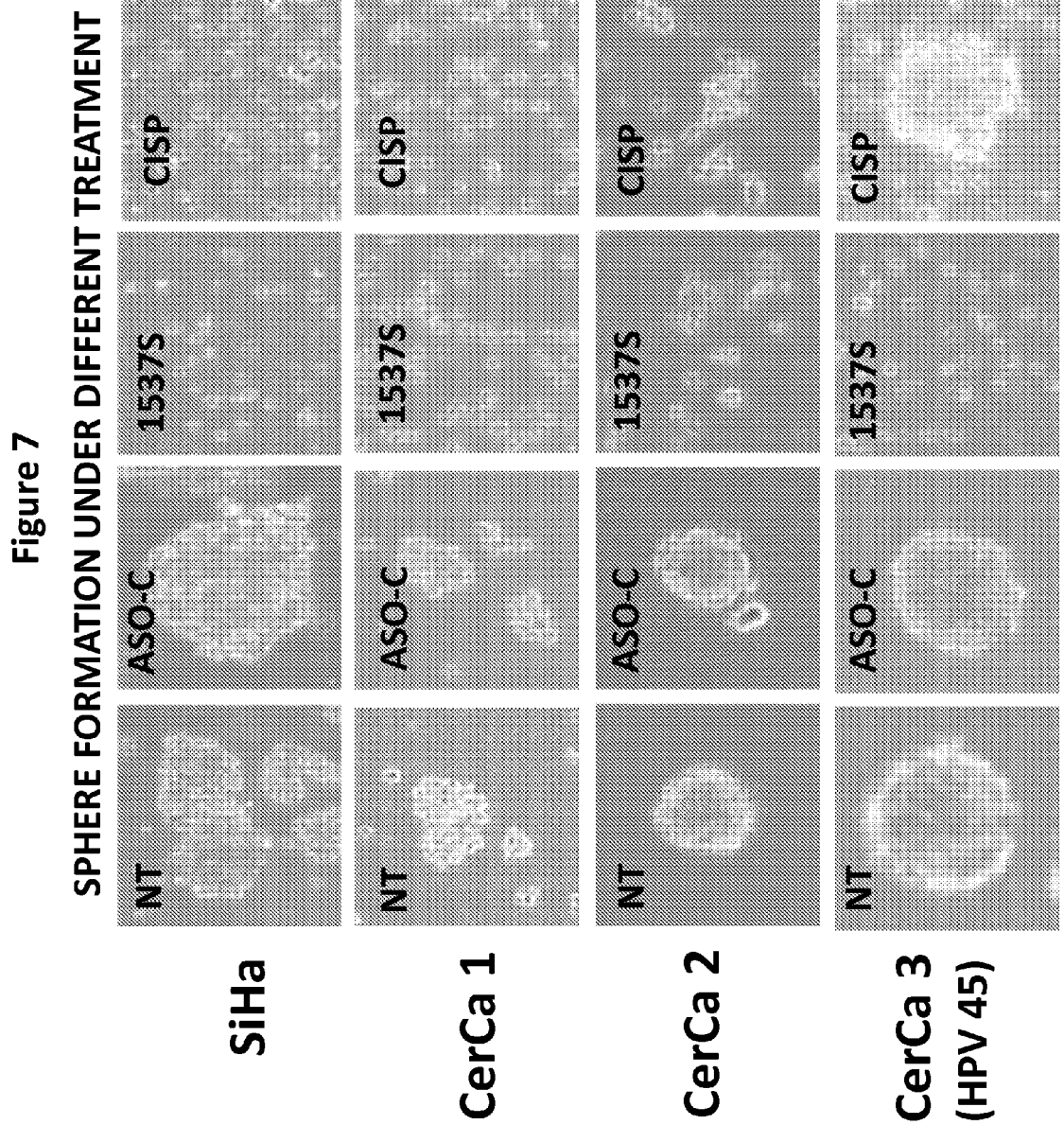
FIG. 7 depicts representative examples of spheres formed by the cervical cancer SiHa cell line and primary culture cells of cervical tumors following no treatment (NT), treatment with a control oligonucleotide (Control Oligo 154: ASO-C), or treatment with an antisense oligonucleotide targeted to ASncmtRNA (ASO 1537S) or treatment with 45 µM cisplatin (CISP). Treatment with the ASO 1537S abolished the formation of spheres. The CerCa 3 cells obtained from primary culture, which is infected with HPV 45, is resistant to treatment with cisplatin as compared to two other cells obtained from primary culture, which are infected with HPV 16.
Figure 8:
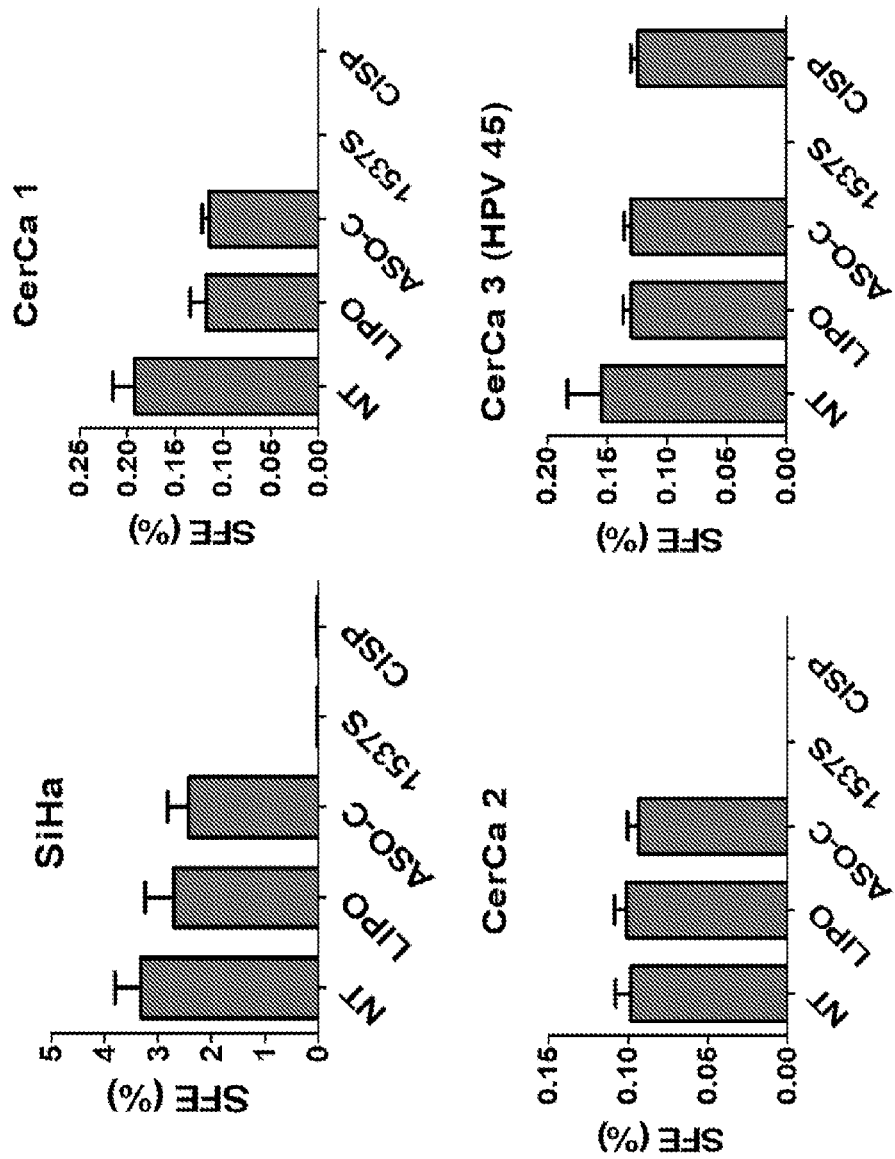
FIG. 8 depicts quantification of sphere formation by the SiHa cell cell line and primary cervical tumor cells (CerCa 1, CerCa 2 and CerCa 3) with or without treatment. Cells transfected with ASO 1537S wer unable to form spheres. The CerCa 3 primary culture infected with HPV 45 was resistant to treatment with cisplatin but not to treatment with ASO 1537S.

Sphere formation was unchanged in primary cultures of cervical tumor cells following no treatment (NT), treatment with only Lipofectamine (LIPO), or treatment with control oligonucleotide 154 (ASO-C). In contrast, sphere formation was abolished in SiHa, CerCa 1, CerCa 2 and CerCa 3 primary cultures following treatment with ASO 1537S (FIG. 7 and FIG. 8). Sphere formation of SiHa, CerCa 1 and CerCa 2 cells (all infected with HPV 16) was also abolished when cells were treated with the drug cisplatin (CISP) (45 µM) (FIG. 7 and FIG. 8) while no effect was observed in CerCa 3 cells (infected with HPV 45) treated with cisplatin.

Taken together, these results show that cervical cancer primary cultures (CerCa 1, CerCa 2 and CerCa 3 cells) and the cell line SiHa left untreated, treated with only Lipofectamine, or transfected with a control oligonucleotide retained the ability to form spheres. In contrast, primary cervical tumor cells or SiHa cells transfected with antisense oligonucleotides targeted to the antisense non-coding chimeric mitochondrial RNA (ASncmtRNA) molecules or sense non-coding chimeric mitochondrial RNA (SncmtRNA) molecule, lost their ability to form spheres whether HPV 16 or HPV 45 positive. These results indicate that the antisense oligonucleotides were able to kill cervical cancer stem cells as indicated by the lack of sphere formation upon treatment. Moreover, treatment with the anti-cancer drug cisplatin abolished sphere formation of SiHa, CerCa 1 and CerCa 2 cells (all HPV 16 positive) but not CerCa 3 that is infected with HPV 45 (FIG. 7 and FIG. 8). Therefore, these results indicate that the antisense oligonuleotides are able to kill cervical cancer stem (CerCa 3 cells) resistant to cisplatin treatment. See Tjalme et al., *Am. J. Clin. Pathol.*, 137:161, 2012; de Sanjosé et al., *Eur J Cancer.*, 49(16): 3450, 2013; Tjalma et al., *Int J Cancer.*, 132(4):854, 2013.

Example 3: Treatment of Mice with Antisense Oligonucleotides Complementary to the Antisense Non-Coding Chimeric Mitochondrial RNA Following Surgery to Remove Intradermal Melanoma Tumors Prevented Relapse of Tumor Growth and Metastasis in the Lungs and Liver One common clinical protocol for melanoma includes surgical resection follow by systemic administration of drugs. Similar protocols are used in the practice of other tumors. In the melanoma model presented in this representative example, B16F10 melanoma cells (100,000 cells in 200 µl of saline) were injected subcutaneously on the back of C57BL/6 mice. About 11 to 12 days post-cell injection, tumors between 700 to 1.000 mm3 developed (a 1,000 mm3 tumor in mice is considered equivalent to a 3,000 cc3 tumor in humans). At this time, mice were randomly divided in two groups (Control Oligo ASO 154 and ASO 1560S (SEQ ID NO:198)) with similar tumor volume. Tumors were surgically resected under anesthesia and the wound washed once with 250 µl containing 100 µg of ASO 1560S or ASO 154. After surgical suture, a bolus of 200 µl saline containing 100 µg of ASO 154 or ASO 1560S was applied into the cavity left by the tumor. Three days post-surgery, mice received on alternative days, 3 intravenous (FIG. 9; 1st, 3rd, 5th arrows on timeline) or 3 intraperitoneal (FIG. 9; 2nd, 4th, 6th arrows on timeline) injections of 250 µl saline containing 100 µg of either ASO 1560S or ASO 154. Tumor growth was measured twice a week with a caliper.

Figure 9:
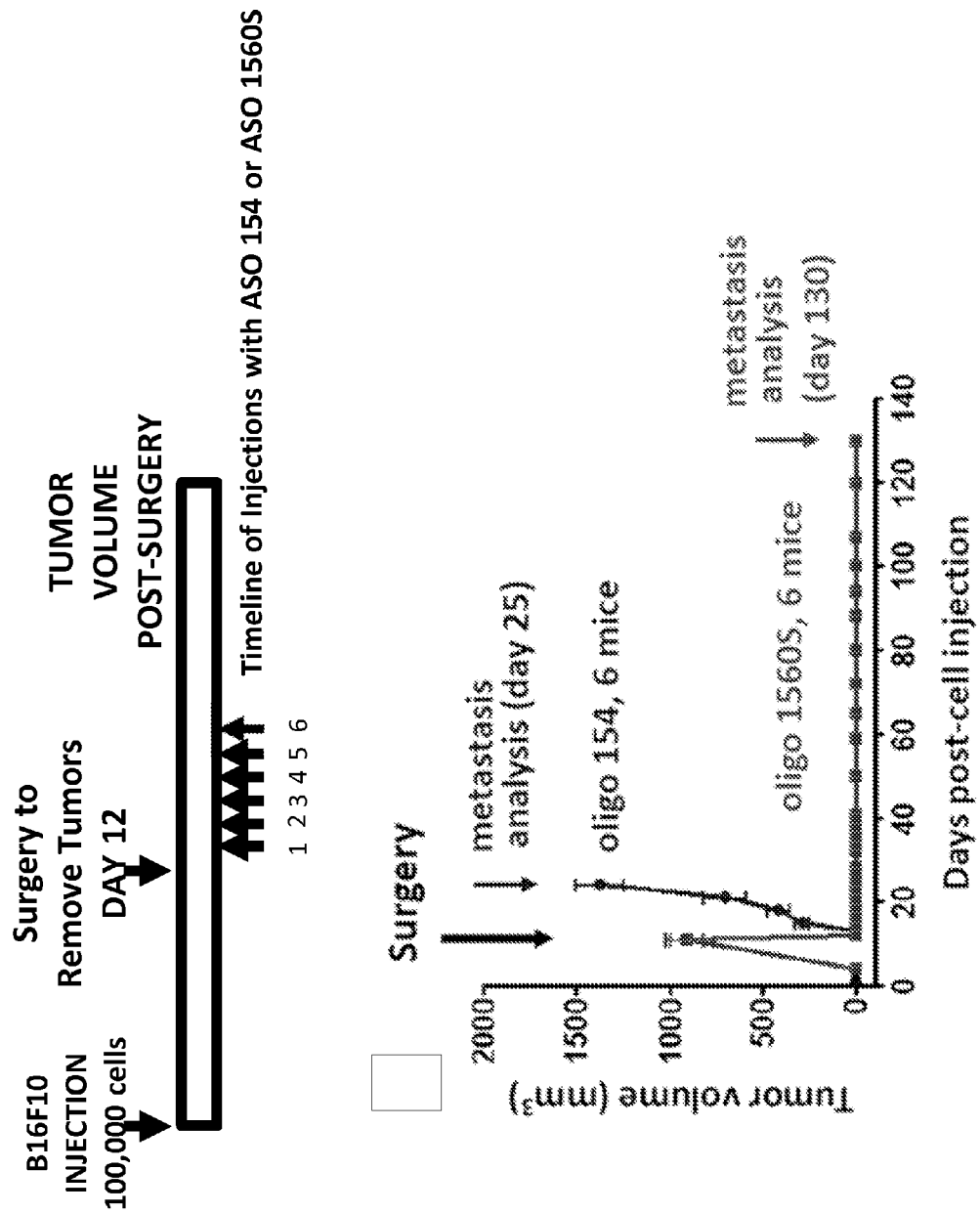
FIG. 9 depicts the absence of tumor relapse and the absence of metastatic nodules in the lungs and liver of mice treated with ASO 1560S (squares) but not Control Oligo 154 (circles) following the surgical removal of intradermal melanoma tumors.

Relapse of tumor growth in mice treated with ASO 154 was observed about 3 days post-surgery and tumor volume of about 1,500 mm3 was reached on about the 25th day post-cell injection (FIG. 9). These mice were euthanized under anesthesia, and the tumor and other organs were fixed and saved for further studies. No relapse was observed in mice treated with ASO 1560S targeted to the mouse AsncmtRNAs. At 130 days post-cell injection, mice appeared healthy without the presence of detectable tumors and were euthanized to collect organs. Livers and lungs were analyzed for the presence of metastatic nodules.

Figure 10:
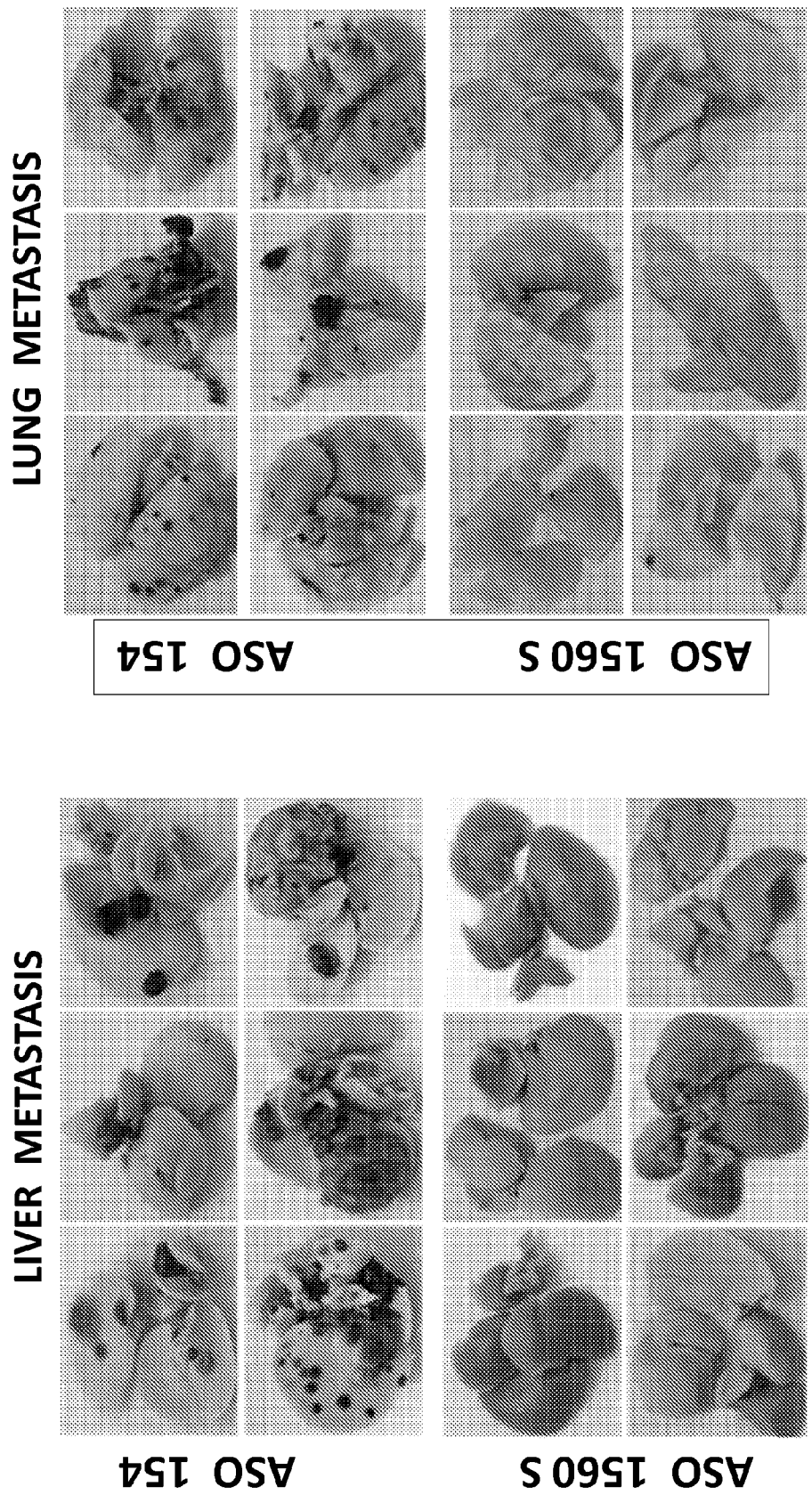
FIG. 10 depicts the presence of tumor relapse metastatic black nodules in the lung and livers of the mice treated with Control Oligo 154 but not in the lungs and livers mice treated with ASO 1560S.

Control mice (treated with Control Oligo ASO 154) showed the presence of cancer relapse and metastatic black nodules in the lung and liver. In contrast, the lungs and livers of the mice treated with ASO 1560S lacked the presence of metastatic nodules demonstrating that ASO 1560S prevented or suppressed cancer relapse (FIG. 10).

Figure 11:
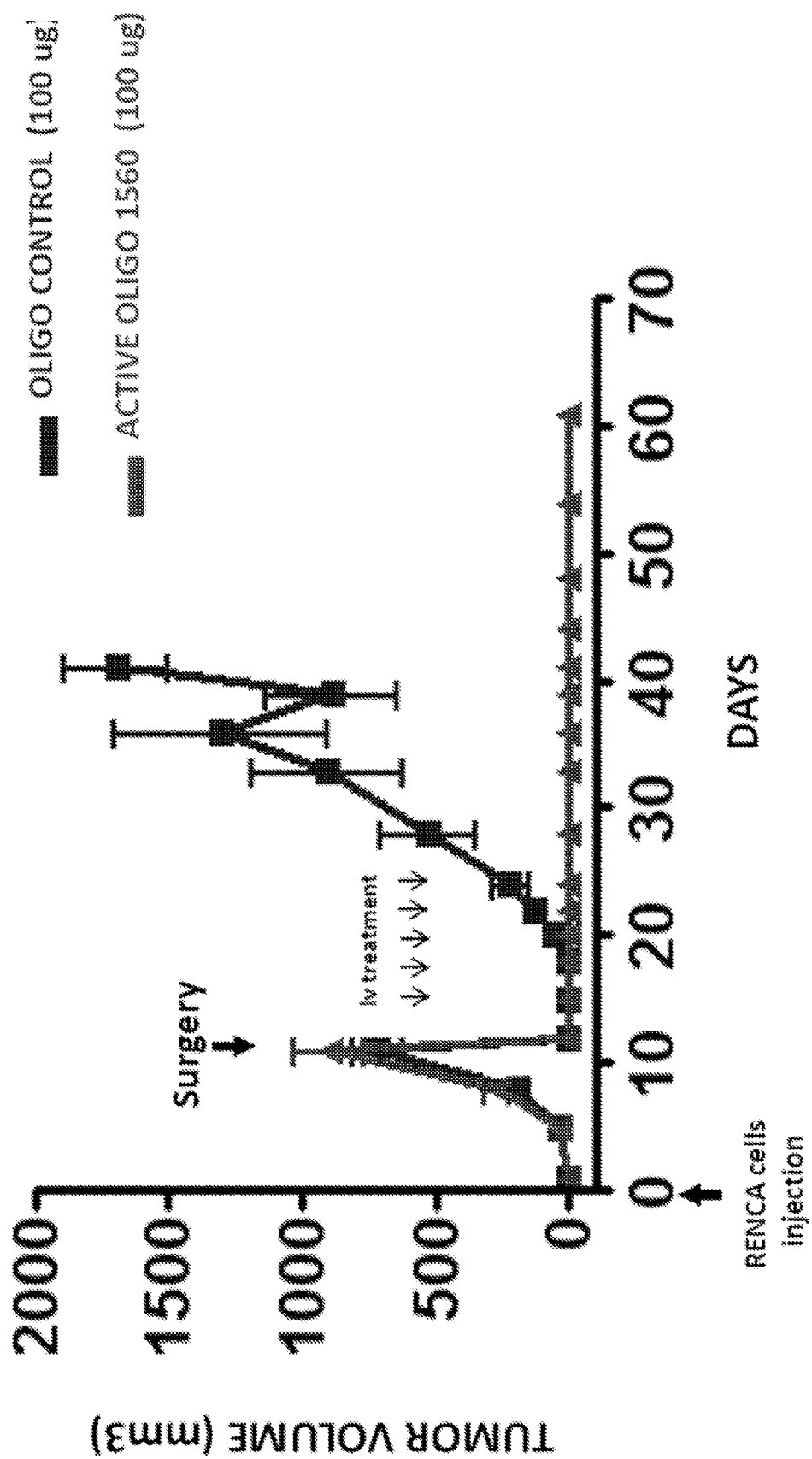
FIG. 11 depicts the absence of tumor relapse and complete survival of mice treated with ASO 1560S (triangles) but not Control ASO 154 (squares) following surgical removal of intradermal kidney carcinoma tumors.

Example 4: Intravenous Treatment of Mice with Antisense Oligonucleotides Complementary to the Antisense Non-Coding Chimeric Mitochondrial RNA Following Surgery to Remove Intradermal Kidney Tumors Resulted in Absence of Tumor Relapse and Complete Survival 100,000 RENCA cells (ATCC® CRL-2947™ mus musculus kidney renal adenocarcina) were injected subcutaneously at day 0. At day 12, tumors of an average size of 800 mm3 were removed and the site of the tumor was washed with 100 µg of Control Oligo ASO 154 (4 animals) or ASO1560S (5 animals) in 200 µl, both formulated in liposomes. The animals were sutured and intravenously injected at the site of the removed tumor with 100 µg of ASO 154 (FIG. 11, squares) or ASO 1560S (FIG. 11, triangles), both formulated in liposomes, in 250 µl. No further treatment was given. At day 40, (30 days post-surgery), all the control animals had died with tumors of an average size of 1,200 mm3 and extensive metastasis, while all animals treated with ASO 1560S had no tumors and were still alive at day 61 (FIG. 11).

Figure 12:
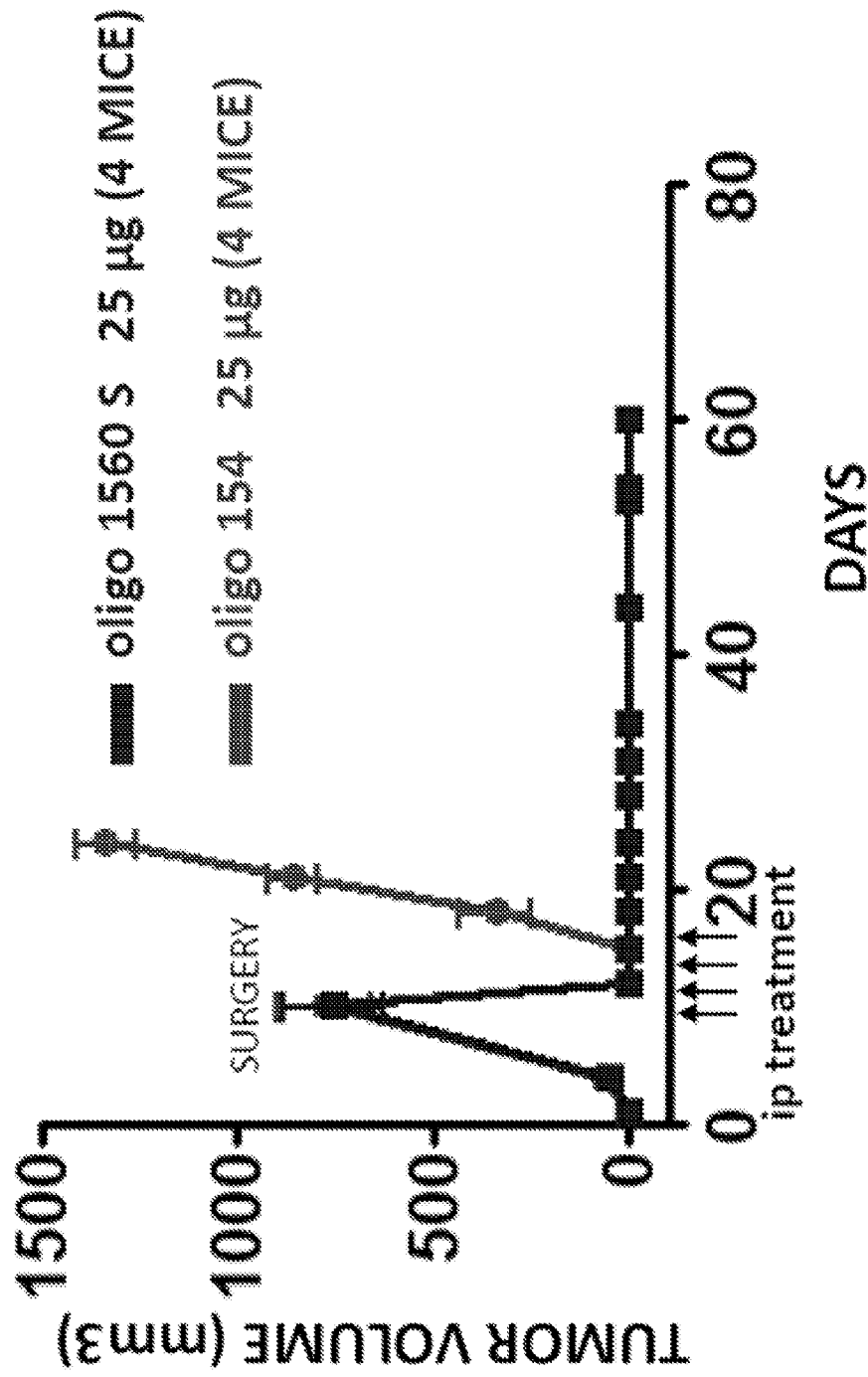
FIG. 12 depicts the absence of relapse in and survival of mice treated with ASO 1560S (squares) but not Control ASO 154 (circles) following surgical removal of intradermal kidney carcinoma tumors.

Example 5: Intraperitoneal Treatment of Mice with Antisense Oligonucleotides Complementary to the Antisense Non-Coding Chimeric Mitochondrial RNA Following Surgery to Remove Intradermal Kidney Tumors Resulted in Absence of Tumor Relapse and Complete Survival 100,000 RENCA cells (ATCC® CRL-2947™ mus musculus kidney renal adenocarcina) were injected subcutaneously on day 0 in 8 mice. On day 11, tumors had an average size of 800 mm3. Tumors of all animals were removed by surgery and divided in 2 groups. The wound of the control group was washed once with Control Oligo ASO 154 before suturing and the wound of the treated group was washed with ASO 1560S before suturing. Post-suture, a bolus of 250 µl was intraperiotoneally injected in the place of where tumor had grown: the control group was injected with ASO 154 and the treated group with ASO 1560S. On days 13, 15, 17 and 19, intraperitoneal injections of 25 µg ASO 154 (FIG. 12, circles) or 25 µg ASO 1560S (FIG. 12, squares) formulated in liposomes were injected in a volume of 250 µl. On days 14, 16 and 18, the mice were injected intravenously with the same protocol. On day 22, all control animals had tumors larger than 1,200 mm3 and were sacrificed. On day 60, all animals treated with ASO 1560S had no tumors and were still alive (FIG. 12).

Example 6: Treatment of Mice with Antisense Oligonucleotides Complementary to the Antisense Non-Coding Chimeric Mitochondrial RNA Following Surgery to Remove Intradermal Melanoma Tumors Resulted in Absence of Tumor Relapse and Complete Survival B16F10 melanoma cells (100.000 cells in 200 μl of RPMI medium) were injected into mice subcutaneously on day 0. On day 11, surgery was carried out to remove tumors. The tumor volumes varied from approximately 800 to 1200 mm3. The wound was washed once. Post-suture one bolus of 250 μl of oligo in liposomes was injected in the tumor site. On days 13, 15, 17, 19 and 21, a dose of 25 μg control ASO 154 naked (FIG. 13, squares), 25 μg of control ASO 154 in liposomes (FIG. 13, circles), or 50 μg of ASO 154 in liposomes (FIG. 13, triangles), each in a volume of 250 μl, was intraperitoneally injected in the mice. Other groups of mice (6 mice per group) were injected in a similar manner as described above with 50 μg of ASO 1560 naked, 25 μg of ASO 1560S in liposomes or 50 μg of ASO 1560S in liposomes (FIG. 13, diamonds).

Figure 13:
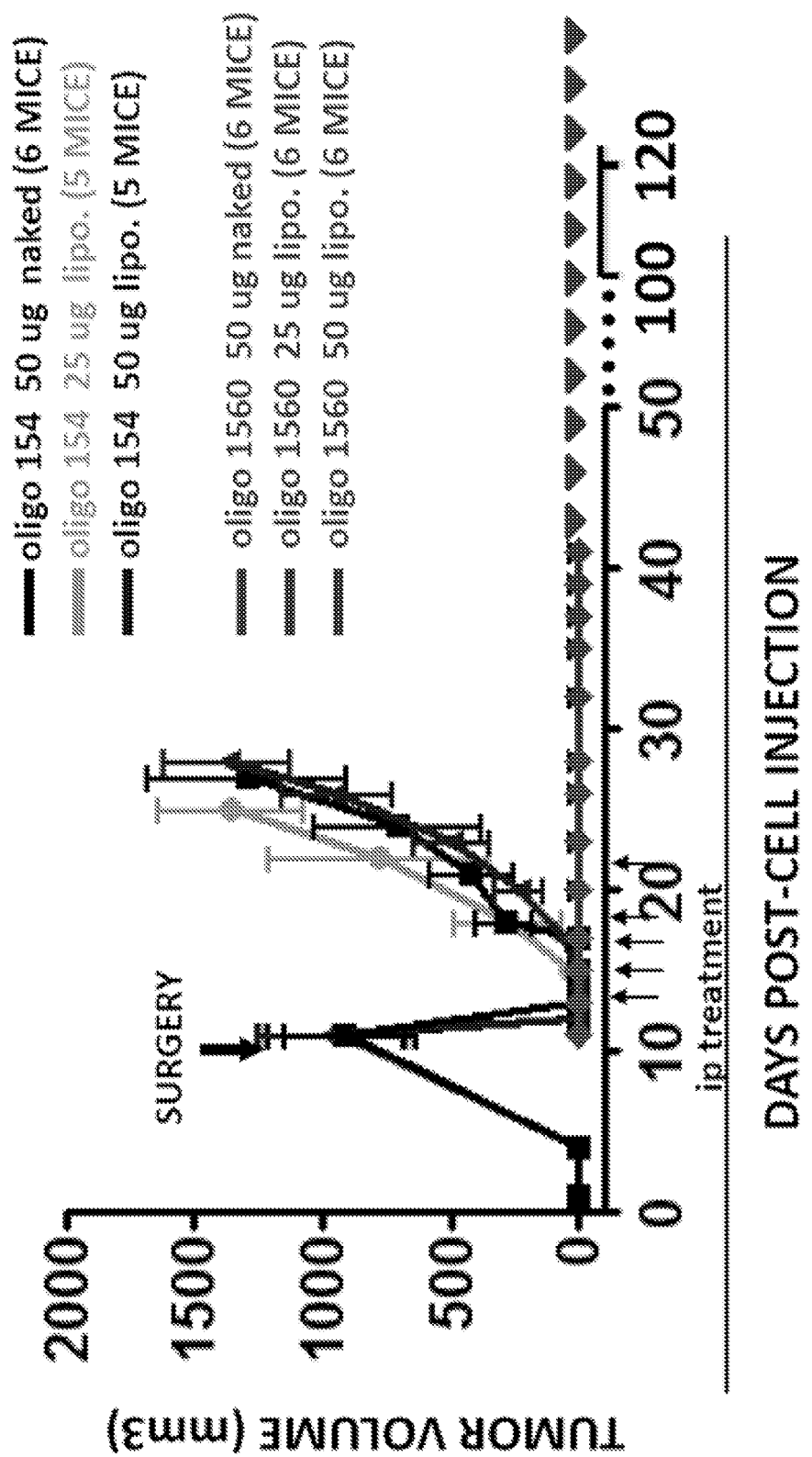
FIG. 13 depicts the absence of tumor relapse and complete survival of mice treated with ASO 1560S but not Control ASO 154 following surgical removal of intradermal melanoma carcinoma tumors.

Compared to mice treated with a control oligonucleotide, post-surgery treatment with 25 and 50 μg intraperitoneal injections of ASO 1560S resulted in the absence of the intradermal melanoma tumor relapse and complete survival (FIG. 13).

Figure 14:
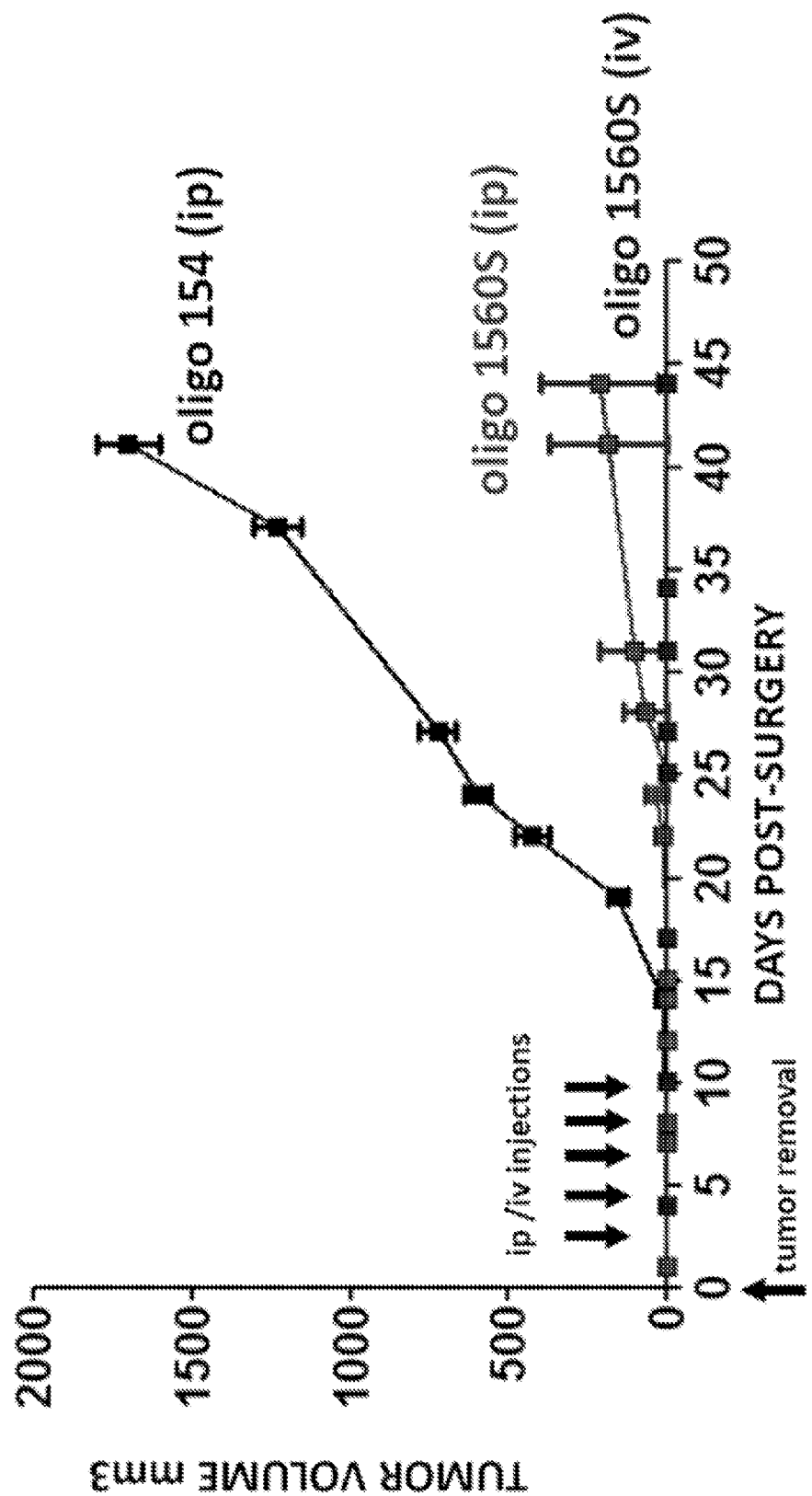
FIG. 14 depicts the absence of tumors and complete survival of mice treated with ASO 1560S but not Control ASO 154 following surgical removal of subcutaneous bladder carcinoma tumors. ip indicates intraperitoneal administration and iv indicates intravenous administration.

Example 7: Intraperitoneal or Intravenous Treatment of Mice with Antisense Oligonucleotides Complementary to the Antisense Non-Coding Chimeric Mitochondrial RNA Following Surgery to Remove Subcutaneous Bladder Carcinoma Tumors Resulted in Absence of Tumor and Complete Survival Twelve mice were injected subcutaneously with a 100,000 MB49 cells (mouse bladder cancer cells). After 15 days mice had tumors of an average diameter of 800 mm3. Tumors were surgically removed (day 0) and a bolus of 200 μl containing 100 μg of ASO 154 (control) or ASO 1560S (active drug) was injected at the site of the surgery. Three days post-surgery mice were divided in 2 groups and treated intraperitoneally or intravenously with 100 μl injections containing ASO 154 (control group) or ASO 1560S (treated group) as indicated in FIG. 14. Only one mouse treated intraperitoneally with ASO 1560S developed a tumor. All the mice treated intravenously with ASO 1560S remained without tumors and experienced full survival. Control animals treated with Control Oligo ASO 154 were sacrificed at day 41 (FIG. 14).

Example 8: Treatment of Rag −/− Mice with Antisense Oligonucleotides Complementary to the Antisense Non-Coding Chimeric Mitochondrial RNA Following Tumor Removal of a Human Melanoma Resulted in Significant Elimination of Tumor Relapse and a Large Increase in Survival Rag −/− mice were injected with 5 million human A375 melanoma cells. Approximately at 34 days post cell-injection, all mice developed tumors of about 700 mm3. Mice were subjected to tumor removal surgery and divided randomly in two groups.

Group 1 (control): the wound was washed with 50 μg of Control Oligo 154 (6 mice in group) in a volume of 200 μl. Group 2 (therapy): the wound was washed with 50 μg of ASO 1537S (8 mice in group) (Sequence of the oligonucleotide provided in Example 1) in 200 μl. After suturing, a bolus of 250 μl containing 50 μg of Control Oligo 154 (6 control mice) or 250 μl containing 50 μg of ASO Oligo 1537S was applied (8 therapy mice). Two days later mice received 6 injections with Control Oligo 154 or ASO Oligo 1537S every other day. The first injection was intraperitoneal and the second injection was in the tail vein.

Figure 15:
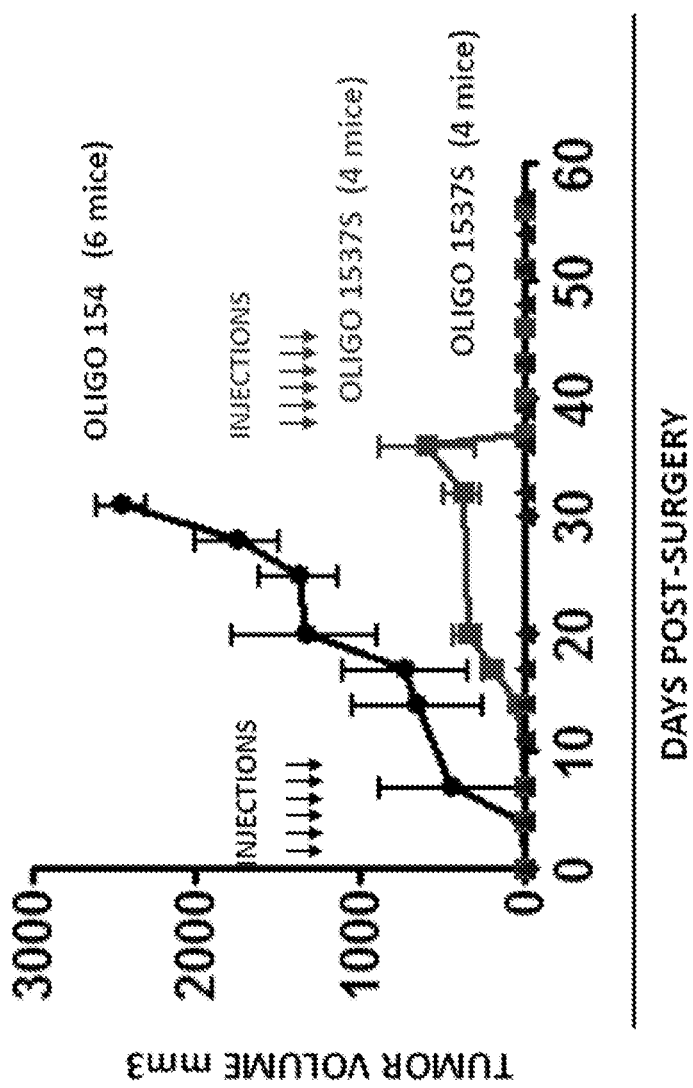
FIG. 15 depicts the reduction in tumors and increase in survival of Rag −/− mice treated with ASO 1537S but not Control ASO 154 following the removal of a human A375 melanoma tumor.

On day 30 after surgery, the 6 mice treated with Control Oligo 154 had tumors on the order of 2000 mm3 and were sacrificed (FIG. 15, circles). On day 57 after surgery, 4 out of the 8 mice receiving ASO Oligo 1537S were without tumors (FIG. 15, triangles). On day 17 post surgery, 4 out of the 8 mice receiving ASO Oligo 1537S began to show small tumors that grew slowly which at day 36 reached a size of about 500 mm3 (FIG. 15, squares). These mice were again subjected to surgery to remove the tumors, and subsequently 2 mice died. The other 2 mice were subjected to the same therapeutic protocol (alternating 3 injections intraperitoneal and 3 injections intravenous) with 50 μg of ASO Oligo 1537S in 250 μl (FIG. 15).

What is claimed is:

1. A method for treating or suppressing metastatic cancer in an individual comprising administering to the individual an effective amount of one or more oligonucleotide complementary to a human non-coding chimeric mitochondrial RNA molecule comprising:
   a. an antisense 16S mitochondrial ribosomal RNA covalently linked at its 5' end to the 3' end of a polynucleotide with an inverted repeat sequence or
   b. a sense 16S mitochondrial ribosomal RNA covalently linked at its 5' end to the 3' end of a polynucleotide with an inverted repeat sequence,
   wherein the one or more oligonucleotide is able to hybridize with the chimeric mitochondrial RNA molecules to form a stable duplex, and
   wherein the individual has been previously treated for cancer with a therapy.

2. The method of claim 1, wherein the one or more oligonucleotide is complementary to the antisense 16S mitochondrial ribosomal RNA molecule encoded by a nucleotide sequence selected from the group consisting of SEQ ID NO:4, SEQ ID NO:5, and SEQ ID NO:6.

3. The method of claim 1, wherein the one or more oligonucleotide comprises a nucleotide sequence selected from the group consisting of SEQ ID NOs:7-198.

4. The method of claim 1, wherein the oligonucleotide is administered in combination with:
   (a) a radiation therapy;
   (b) surgery;
   (c) an allogenic stem cell transplant therapy;
   (d) an autologous stem cell transplant therapy; and/or
   (e) at least one anti-cancer agent.

5. The method of claim 1, wherein the metastatic cancer is a solid cancer.

6. The method of claim 1, wherein the metastatic cancer is a non-solid cancer.

7. The method of claim 1, wherein the oligonucleotide reduces the number of cancer stem cells in the individual as compared to an individual not administered the oligonucleotide.

8. The method of claim 1, wherein the metastatic cancer is selected from the group consisting of colon cancer, cervical cancer, bladder cancer, melanoma, prostate cancer, ovarian cancer, and gastric cancer.

9. The method of claim 1, wherein the metastatic cancer is selected from the group consisting of colon cancer, cervical cancer, bladder cancer, and melanoma.

10. The method of claim 2, wherein the one or more oligonucleotide is 10-50 nucleobases in length.

11. The method of claim 2, wherein the one or more oligonucleotide is 10-30 nucleobases in length.

* * * * *